(12) United States Patent
Li et al.

(10) Patent No.: US 9,499,591 B2
(45) Date of Patent: Nov. 22, 2016

(54) TRUNCATED L1 PROTEIN OF HUMAN PAPILLOMAVIRUS TYPE 52

(75) Inventors: Shaowei Li, Xiamen (CN); Xiaobing Mo, Xiamen (CN); Minxi Wei, Xiamen (CN); Huirong Pan, Xiamen (CN); Jun Zhang, Xiamen (CN); Ningshao Xia, Xiamen (CN)

(73) Assignees: XIAMEN UNIVERSITY, Xiamen, Fujian Province (CN); XIAMEN INNOVAX BIOTECH CO., LTD., Haicang, Xiamen, Fujian (CN)

(*) Notice: Subject to any disclaimer, the term of this patent is extended or adjusted under 35 U.S.C. 154(b) by 4 days.

(21) Appl. No.: 13/807,858

(22) PCT Filed: Jul. 1, 2011

(86) PCT No.: PCT/CN2011/076763
§ 371 (c)(1),
(2), (4) Date: Mar. 15, 2013

(87) PCT Pub. No.: WO2012/000454
PCT Pub. Date: Jan. 5, 2012

(65) Prior Publication Data
US 2013/0230548 A1 Sep. 5, 2013

(30) Foreign Application Priority Data
Jul. 2, 2010 (CN) .......................... 2010 1 0216189

(51) Int. Cl.
| A61K 39/12 | (2006.01) |
| C07K 14/025 | (2006.01) |
| C07K 14/005 | (2006.01) |
| A61K 39/00 | (2006.01) |
| C12P 21/02 | (2006.01) |

(52) U.S. Cl.
CPC ......... *C07K 14/025* (2013.01); *A61K 39/0011* (2013.01); *A61K 39/12* (2013.01); *C07K 14/005* (2013.01); *C12P 21/02* (2013.01); *A61K 2039/5258* (2013.01); *A61K 2039/585* (2013.01); *C12N 2710/20022* (2013.01); *C12N 2710/20023* (2013.01); *C12N 2710/20034* (2013.01); *C12N 2710/20051* (2013.01)

(58) Field of Classification Search
None
See application file for complete search history.

(56) References Cited

U.S. PATENT DOCUMENTS

| 6,551,597 B1 | 4/2003 | Harrison et al. | |
| 7,744,892 B2 * | 6/2010 | Bryan et al. | ............... 424/184.1 |

FOREIGN PATENT DOCUMENTS

| CN | 1478790 | 3/2004 |
| CN | 1934131 A | 3/2007 |
| CN | 101153280 A | 4/2008 |
| CN | 101293918 | 10/2008 |
| CN | 101343314 | 1/2009 |
| CN | 101343315 | 1/2009 |
| CN | 101570571 | 11/2009 |
| EP | 2 147 926 A1 | 1/2010 |
| EP | 2 154 147 A1 | 2/2010 |
| WO | WO 00/54730 | 9/2000 |

OTHER PUBLICATIONS

GenBank: ADR90828.1, Sequence 2 from U.S. Pat. No. 7,744,892, http://www.ncbi.nlm.nih.gov/protein/ADR90828.1, dated Dec. 12, 2010.*
Ma et al. Increasing the expression levels of papillomavirus major capsid protein in *Escherichia coli* by N-terminal deletion. Protein Expr Purif. Nov. 2007;56(1):72-9. Epub May 29, 2007.*
GenBank: CAA52590.1. late protein [Human papillomavirus type 52]. http://www.ncbi.nlm.nih.gov/protein/397045. Apr. 18, 2005.*
GenBank: ACV84004.1. major capsid protein L1 [Human papillomavirus type 16]. http://www.ncbi.nlm.nih.gov/protein/ACV84004.1. Dated Sep. 22, 2009.*
Fey et al. Demonstration of in vitro synthesis of human papilloma viral proteins from hand and foot warts. J Invest Dermatol. Jun. 1989;92(6):817-24.*
Machine English translation of CN 101153280 A.*
Kozak. Point Mutations Define a Sequence Flanking the AUG Initiator Codon That Modulates Translation by Eukaryotic Ribosomes. Cell, vol. 44, 283-292, Jan. 31, 1986.*
Zemskovaa et al. Transient expression of deletion mutants of the herpes simplex virus thymidine kinase-encoding gene in mouse fibroblast cells. Gene. vol. 106, Issue 2, Oct. 15, 1991, pp. 249-253.*
Chen et al. J. Mol. Biol. (2001) 307, 173-182.*
Huhti et al. A comparison of methods for purification and concentration of norovirus GII-4 capsid virus-like particles. Arch Virol (2010) 155:1855-1858.*
GenBank: AEI61597.1. late protein L1 [Human papillomavirus type 52]. Dated Jun. 27, 2011. http://www.ncbi.nlm.nih.gov/protein/AEI61597.1.*
Needleman et al.; "A General Method Applicable to the Search for Similarities in the Amino Acid Sequence of Two Proteins"; J. Mol. Bio, 1970; 48; pp. 443-453.
Buck et al.; "Arrangement of L2 within the Papillomavirus Capsid"; Journal of Virology, Jun. 2008; vol. 82; No. 11; pp. 5190-5197.
Banks et al.; "Expression of Human Papillomavirus Type 6 and Type 16 Capsid Proteins in Bacteria and Their Antigenice Characterization", J. gen. Vivol., 1987; 68; pp. 3081-3089.
Kelsall et al.; "Expression of the major capsid protein of human papillomavirus type 16 in *Escherichia coli*", Journal of Virological Methods, 53; 1995; pp. 75-90.

(Continued)

*Primary Examiner* — Nick Zou
(74) *Attorney, Agent, or Firm* — Pillsbury Winthrop Shaw Pittman, LLP

(57) ABSTRACT

Provided is a truncated L1 protein of Human Papillomavirus (HPV) Type 52 which, compared to a wild type HPV52 L1 protein, is truncated by 27-42 amino acids at the N-terminal. Also provided are a coding sequence of the truncated HPV52 L1 protein, a virus-like particle (VLP) comprising the protein, and a method of preparing the protein and the VLP using an *E. coli* expression system. The truncated HPV52 L1 protein and an assembled VLP can be used to prevent an HPV52 infection and a disease caused by HPV52 infection, such as cervical cancer.

16 Claims, 12 Drawing Sheets

(56) References Cited

OTHER PUBLICATIONS

Li et al.; " Expressions of Human Papillomavirus Type 11 L1 Capsid Protein in *Escherichia coli*: Characterizaiton of Protein Domains Involved in DNA Binding and Capsid Assembly"; Journal of Virology, Apr. 1997;vol. 71; No. 4; pp. 2988-2995.

Burks et al.; "In Vitro Scanning saturation mutagenesis of an antibody binding pocket"; Proc. Natl. Acad. Sci, USA, Jan. 1997; vol. 94, pp. 412-417.

Kirnbauer et al.; "Papillomavirus L1 major capsid protein self-assembles into virus-like particesl that are highly immunogenic"; Pro. Natl. Acad. Sci. USA; vol. 89; Dec. 1992; pp. 12180-12184.

Myers et al.; "Optimal alignments in linear space"; Comput Appl Bioscience; Mar. 1988;4(1):11-7; pp. 1-13.

Hagensee et al.; "Three-Dimensional Structure of Vaccinia Virus-Produced Human Papillomavirus Type 1 Capsids"; Journal of Virology, Jul. 1994; vol. 68; No. 7; pp. 4503-4505.

Baker et al.; "Structures of bovine and human papillomaviruses"; Analysis by cryoelectron microscopy and three-dimensional image recontruction; Biophys. J.; vol. 60; Dec. 1994; pp. 1445-1456.

Brummell et al.; "Probing the Combining Site of an Anti-Carbohydrate Antibody by Saturation-Mutagenesis: Role of the Heavy-Chain CDR3 Residues"; Biochemistry 1993; 32; pp. 1180-1187.

Wolf et al.; "Subunit interactions in bovine papillomavirus"; Apr. 6, 2010; vol. 107; No. 14; pp. 6298-6303.

Kobayashi et al.; "Tryptophan H33 plays an important role in pyrimidine (6-4) pyrimidone photoproduct binding by a high-affinity antibody"; Protein Engineering; 1994; vol. 12; No. 10; pp. 879-884.

International Search Report for PCT/CN2011/076763.

European Search Reported dated Nov. 15, 2013 for Appln No. 11800199.9.

Ma et al.; "Increasing the expression levels of papillomavirus major capsid protein in *Escherichia coli* by N-terminal deletion", Protein Expression and Purification, Academic Press, Sand Diego, CA, vol. 56, No. 1, Oct. 3, 2007, pp. 72-79.

Chen et al.; "Papillomavirus capsid protein expression in *Escherichia coli* purification and assembly of HPV11 and HPV16 L1", Journal of Molecular Biology, Academic Press, United Kingdom, vol. 307, No. 1, Mar. 16, 2001, pp. 173-182.

* cited by examiner

SEQUENCE LISTING

<160> NUMBER OF SEQ ID NOS: 32

<210> SEQ ID NO 1
<211> LENGTH: 503
<212> TYPE: PRT
<213> ORGANISM: Artificial sequence
<220> FEATURE:
<223> OTHER INFORMATION: Truncated HPV52 L1 protein

<400> SEQUENCE: 1

```
Met Ser Val Trp Arg Pro Ser Glu Ala Thr Val Tyr Leu Pro Pro Val
1               5                   10                  15

Pro Val Ser Lys Val Val Ser Thr Asp Glu Tyr Val Ser Arg Thr Ser
            20                  25                  30

Ile Tyr Tyr Tyr Ala Gly Ser Ser Arg Leu Leu Thr Val Gly His Pro
        35                  40                  45

Tyr Phe Ser Ile Lys Asn Thr Ser Ser Gly Asn Gly Lys Lys Val Leu
    50                  55                  60

Val Pro Lys Val Ser Gly Leu Gln Tyr Arg Val Phe Arg Ile Lys Leu
65                  70                  75                  80

Pro Asp Pro Asn Lys Phe Gly Phe Pro Asp Thr Ser Phe Tyr Asn Pro
                85                  90                  95
```

```
Glu Thr Gln Arg Leu Val Trp Ala Cys Thr Gly Leu Glu Ile Gly Arg
                100                 105                 110

Gly Gln Pro Leu Gly Val Gly Ile Ser Gly His Pro Leu Leu Asn Lys
            115                 120                 125

Phe Asp Asp Thr Glu Thr Ser Asn Lys Tyr Ala Gly Lys Pro Gly Ile
            130                 135                 140

Asp Asn Arg Glu Cys Leu Ser Met Asp Tyr Lys Gln Thr Gln Leu Cys
145                 150                 155                 160

Ile Leu Gly Cys Lys Pro Pro Ile Gly Glu His Trp Gly Lys Gly Thr
                165                 170                 175

Pro Cys Asn Asn Asn Ser Gly Asn Pro Gly Asp Cys Pro Pro Leu Gln
                180                 185                 190

Leu Ile Asn Ser Val Ile Gln Asp Gly Asp Met Val Asp Thr Gly Phe
            195                 200                 205

Gly Cys Met Asp Phe Asn Thr Leu Gln Ala Ser Lys Ser Asp Val Pro
            210                 215                 220

Ile Asp Ile Cys Ser Ser Val Cys Lys Tyr Pro Asp Tyr Leu Gln Met
225                 230                 235                 240

Ala Ser Glu Pro Tyr Gly Asp Ser Leu Phe Phe Phe Leu Arg Arg Glu
                245                 250                 255

Gln Met Phe Val Arg His Phe Phe Asn Arg Ala Gly Thr Leu Gly Asp
            260                 265                 270

Pro Val Pro Gly Asp Leu Tyr Ile Gln Gly Ser Asn Ser Gly Asn Thr
            275                 280                 285

Ala Thr Val Gln Ser Ser Ala Phe Phe Pro Thr Pro Ser Gly Ser Met
            290                 295                 300

Val Thr Ser Glu Ser Gln Leu Phe Asn Lys Pro Tyr Trp Leu Gln Arg
305                 310                 315                 320

Ala Gln Gly His Asn Asn Gly Ile Cys Trp Gly Asn Gln Leu Phe Val
                325                 330                 335

Thr Val Val Asp Thr Thr Arg Ser Thr Asn Met Thr Leu Cys Ala Glu
            340                 345                 350

Val Lys Lys Glu Ser Thr Tyr Lys Asn Glu Asn Phe Lys Glu Tyr Leu
            355                 360                 365

Arg His Gly Glu Glu Phe Asp Leu Gln Phe Ile Phe Gln Leu Cys Lys
            370                 375                 380

Ile Thr Leu Thr Ala Asp Val Met Thr Tyr Ile His Lys Met Asp Ala
385                 390                 395                 400

Thr Ile Leu Glu Asp Trp Gln Phe Gly Leu Thr Pro Pro Pro Ser Ala
                405                 410                 415

Ser Leu Glu Asp Thr Tyr Arg Phe Val Thr Ser Thr Ala Ile Thr Cys
            420                 425                 430

Gln Lys Asn Thr Pro Pro Lys Gly Lys Glu Asp Pro Leu Lys Asp Tyr
            435                 440                 445

Met Phe Trp Glu Val Asp Leu Lys Glu Lys Phe Ser Ala Asp Leu Asp
            450                 455                 460

Gln Phe Pro Leu Gly Arg Lys Phe Leu Leu Gln Ala Gly Leu Gln Ala
465                 470                 475                 480

Arg Pro Lys Leu Lys Arg Pro Ala Ser Ser Ala Pro Arg Thr Ser Thr
                485                 490                 495

Lys Lys Lys Lys Val Lys Arg
            500
```

<210> SEQ ID NO 2
<211> LENGTH: 500
<212> TYPE: PRT
<213> ORGANISM: Artificial sequence
<220> FEATURE:
<223> OTHER INFORMATION: Truncated HPV52 L1 protein

<400> SEQUENCE: 2

```
Met Arg Pro Ser Glu Ala Thr Val Tyr Leu Pro Pro Val Pro Val Ser
1               5                   10                  15

Lys Val Val Ser Thr Asp Glu Tyr Val Ser Arg Thr Ser Ile Tyr Tyr
                20                  25                  30

Tyr Ala Gly Ser Ser Arg Leu Leu Thr Val Gly His Pro Tyr Phe Ser
            35                  40                  45

Ile Lys Asn Thr Ser Ser Gly Asn Gly Lys Lys Val Leu Val Pro Lys
        50                  55                  60

Val Ser Gly Leu Gln Tyr Arg Val Phe Arg Ile Lys Leu Pro Asp Pro
65                  70                  75                  80

Asn Lys Phe Gly Phe Pro Asp Thr Ser Phe Tyr Asn Pro Glu Thr Gln
                85                  90                  95

Arg Leu Val Trp Ala Cys Thr Gly Leu Glu Ile Gly Arg Gly Gln Pro
            100                 105                 110

Leu Gly Val Gly Ile Ser Gly His Pro Leu Leu Asn Lys Phe Asp Asp
        115                 120                 125

Thr Glu Thr Ser Asn Lys Tyr Ala Gly Lys Pro Gly Ile Asp Asn Arg
130                 135                 140

Glu Cys Leu Ser Met Asp Tyr Lys Gln Thr Gln Leu Cys Ile Leu Gly
145                 150                 155                 160

Cys Lys Pro Pro Ile Gly Glu His Trp Gly Lys Gly Thr Pro Cys Asn
                165                 170                 175

Asn Asn Ser Gly Asn Pro Gly Asp Cys Pro Pro Leu Gln Leu Ile Asn
            180                 185                 190

Ser Val Ile Gln Asp Gly Asp Met Val Asp Thr Gly Phe Gly Cys Met
        195                 200                 205

Asp Phe Asn Thr Leu Gln Ala Ser Lys Ser Asp Val Pro Ile Asp Ile
210                 215                 220

Cys Ser Ser Val Cys Lys Tyr Pro Asp Tyr Leu Gln Met Ala Ser Glu
225                 230                 235                 240

Pro Tyr Gly Asp Ser Leu Phe Phe Phe Leu Arg Arg Glu Gln Met Phe
                245                 250                 255

Val Arg His Phe Phe Asn Arg Ala Gly Thr Leu Gly Asp Pro Val Pro
            260                 265                 270

Gly Asp Leu Tyr Ile Gln Gly Ser Asn Ser Gly Asn Thr Ala Thr Val
        275                 280                 285

Gln Ser Ser Ala Phe Phe Pro Thr Pro Ser Gly Ser Met Val Thr Ser
290                 295                 300

Glu Ser Gln Leu Phe Asn Lys Pro Tyr Trp Leu Gln Arg Ala Gln Gly
305                 310                 315                 320

His Asn Asn Gly Ile Cys Trp Gly Asn Gln Leu Phe Val Thr Val Val
                325                 330                 335

Asp Thr Thr Arg Ser Thr Asn Met Thr Leu Cys Ala Glu Val Lys Lys
            340                 345                 350

Glu Ser Thr Tyr Lys Asn Glu Asn Phe Lys Glu Tyr Leu Arg His Gly
        355                 360                 365
```

```
Glu Glu Phe Asp Leu Gln Phe Ile Phe Gln Leu Cys Lys Ile Thr Leu
370                 375                 380

Thr Ala Asp Val Met Thr Tyr Ile His Lys Met Asp Ala Thr Ile Leu
385                 390                 395                 400

Glu Asp Trp Gln Phe Gly Leu Thr Pro Pro Ser Ala Ser Leu Glu
            405                 410                 415

Asp Thr Tyr Arg Phe Val Thr Ser Thr Ala Ile Thr Cys Gln Lys Asn
            420                 425                 430

Thr Pro Pro Lys Gly Lys Glu Asp Pro Leu Lys Asp Tyr Met Phe Trp
            435                 440                 445

Glu Val Asp Leu Lys Glu Lys Phe Ser Ala Asp Leu Asp Gln Phe Pro
450                 455                 460

Leu Gly Arg Lys Phe Leu Leu Gln Ala Gly Leu Gln Ala Arg Pro Lys
465                 470                 475                 480

Leu Lys Arg Pro Ala Ser Ser Ala Pro Arg Thr Ser Thr Lys Lys Lys
                485                 490                 495

Lys Val Lys Arg
            500

<210> SEQ ID NO 3
<211> LENGTH: 499
<212> TYPE: PRT
<213> ORGANISM: Artificial sequence
<220> FEATURE:
<223> OTHER INFORMATION: Truncated HPV52 L1 protein

<400> SEQUENCE: 3

Met Pro Ser Glu Ala Thr Val Tyr Leu Pro Pro Val Pro Val Ser Lys
1               5                   10                  15

Val Val Ser Thr Asp Glu Tyr Val Ser Arg Thr Ser Ile Tyr Tyr Tyr
                20                  25                  30

Ala Gly Ser Ser Arg Leu Leu Thr Val Gly His Pro Tyr Phe Ser Ile
            35                  40                  45

Lys Asn Thr Ser Ser Gly Asn Gly Lys Lys Val Leu Val Pro Lys Val
50                  55                  60

Ser Gly Leu Gln Tyr Arg Val Phe Arg Ile Lys Leu Pro Asp Pro Asn
65                  70                  75                  80

Lys Phe Gly Phe Pro Asp Thr Ser Phe Tyr Asn Pro Glu Thr Gln Arg
                85                  90                  95

Leu Val Trp Ala Cys Thr Gly Leu Glu Ile Gly Arg Gly Gln Pro Leu
            100                 105                 110

Gly Val Gly Ile Ser Gly His Pro Leu Leu Asn Lys Phe Asp Asp Thr
            115                 120                 125

Glu Thr Ser Asn Lys Tyr Ala Gly Lys Pro Gly Ile Asp Asn Arg Glu
130                 135                 140

Cys Leu Ser Met Asp Tyr Lys Gln Thr Gln Leu Cys Ile Leu Gly Cys
145                 150                 155                 160

Lys Pro Pro Ile Gly Glu His Trp Gly Lys Gly Thr Pro Cys Asn Asn
                165                 170                 175

Asn Ser Gly Asn Pro Gly Asp Cys Pro Pro Leu Gln Leu Ile Asn Ser
            180                 185                 190

Val Ile Gln Asp Gly Asp Met Val Asp Thr Gly Phe Gly Cys Met Asp
            195                 200                 205

Phe Asn Thr Leu Gln Ala Ser Lys Ser Asp Val Pro Ile Asp Ile Cys
210                 215                 220
```

```
Ser Ser Val Cys Lys Tyr Pro Asp Tyr Leu Gln Met Ala Ser Glu Pro
225                 230                 235                 240

Tyr Gly Asp Ser Leu Phe Phe Leu Arg Arg Glu Gln Met Phe Val
            245                 250                 255

Arg His Phe Phe Asn Arg Ala Gly Thr Leu Gly Asp Pro Val Pro Gly
            260                 265                 270

Asp Leu Tyr Ile Gln Gly Ser Asn Ser Gly Asn Thr Ala Thr Val Gln
            275                 280                 285

Ser Ser Ala Phe Phe Pro Thr Pro Ser Gly Ser Met Val Thr Ser Glu
        290                 295                 300

Ser Gln Leu Phe Asn Lys Pro Tyr Trp Leu Gln Arg Ala Gln Gly His
305                 310                 315                 320

Asn Asn Gly Ile Cys Trp Gly Asn Gln Leu Phe Val Thr Val Val Asp
            325                 330                 335

Thr Thr Arg Ser Thr Asn Met Thr Leu Cys Ala Glu Val Lys Lys Glu
            340                 345                 350

Ser Thr Tyr Lys Asn Glu Asn Phe Lys Glu Tyr Leu Arg His Gly Glu
        355                 360                 365

Glu Phe Asp Leu Gln Phe Ile Phe Gln Leu Cys Lys Ile Thr Leu Thr
370                 375                 380

Ala Asp Val Met Thr Tyr Ile His Lys Met Asp Ala Thr Ile Leu Glu
385                 390                 395                 400

Asp Trp Gln Phe Gly Leu Thr Pro Pro Ser Ala Ser Leu Glu Asp
            405                 410                 415

Thr Tyr Arg Phe Val Thr Ser Thr Ala Ile Thr Cys Gln Lys Asn Thr
            420                 425                 430

Pro Pro Lys Gly Lys Glu Asp Pro Leu Lys Asp Tyr Met Phe Trp Glu
            435                 440                 445

Val Asp Leu Lys Glu Lys Phe Ser Ala Asp Leu Asp Gln Phe Pro Leu
        450                 455                 460

Gly Arg Lys Phe Leu Leu Gln Ala Gly Leu Gln Ala Arg Pro Lys Leu
465                 470                 475                 480

Lys Arg Pro Ala Ser Ser Ala Pro Arg Thr Ser Thr Lys Lys Lys Lys
            485                 490                 495

Val Lys Arg

<210> SEQ ID NO 4
<211> LENGTH: 498
<212> TYPE: PRT
<213> ORGANISM: Artificial sequence
<220> FEATURE:
<223> OTHER INFORMATION: Truncated HPV52 L1 protein

<400> SEQUENCE: 4

Met Ser Glu Ala Thr Val Tyr Leu Pro Pro Val Pro Val Ser Lys Val
1               5                   10                  15

Val Ser Thr Asp Glu Tyr Val Ser Arg Thr Ser Ile Tyr Tyr Tyr Ala
            20                  25                  30

Gly Ser Ser Arg Leu Leu Thr Val Gly His Pro Tyr Phe Ser Ile Lys
        35                  40                  45

Asn Thr Ser Ser Gly Asn Gly Lys Lys Val Leu Val Pro Lys Val Ser
    50                  55                  60

Gly Leu Gln Tyr Arg Val Phe Arg Ile Lys Leu Pro Asp Pro Asn Lys
65                  70                  75                  80

Phe Gly Phe Pro Asp Thr Ser Phe Tyr Asn Pro Glu Thr Gln Arg Leu
```

```
                        85                  90                  95
Val Trp Ala Cys Thr Gly Leu Glu Ile Gly Arg Gly Gln Pro Leu Gly
                100                 105                 110

Val Gly Ile Ser Gly His Pro Leu Leu Asn Lys Phe Asp Asp Thr Glu
            115                 120                 125

Thr Ser Asn Lys Tyr Ala Gly Lys Pro Gly Ile Asp Asn Arg Glu Cys
        130                 135                 140

Leu Ser Met Asp Tyr Lys Gln Thr Gln Leu Cys Ile Leu Gly Cys Lys
145                 150                 155                 160

Pro Pro Ile Gly Glu His Trp Gly Lys Gly Thr Pro Cys Asn Asn Asn
                165                 170                 175

Ser Gly Asn Pro Gly Asp Cys Pro Pro Leu Gln Leu Ile Asn Ser Val
                180                 185                 190

Ile Gln Asp Gly Asp Met Val Asp Thr Gly Phe Gly Cys Met Asp Phe
                195                 200                 205

Asn Thr Leu Gln Ala Ser Lys Ser Asp Val Pro Ile Asp Ile Cys Ser
        210                 215                 220

Ser Val Cys Lys Tyr Pro Asp Tyr Leu Gln Met Ala Ser Glu Pro Tyr
225                 230                 235                 240

Gly Asp Ser Leu Phe Phe Leu Arg Arg Glu Gln Met Phe Val Arg
                245                 250                 255

His Phe Phe Asn Arg Ala Gly Thr Leu Gly Asp Pro Val Pro Gly Asp
                260                 265                 270

Leu Tyr Ile Gln Gly Ser Asn Ser Gly Asn Thr Ala Thr Val Gln Ser
            275                 280                 285

Ser Ala Phe Phe Pro Thr Pro Ser Gly Ser Met Val Thr Ser Glu Ser
        290                 295                 300

Gln Leu Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Thr Leu Cys Ala Glu Val Lys Lys Glu Ser
                340                 345                 350

Thr Tyr Lys Asn Glu Asn Phe Lys Glu Tyr Leu Arg His Gly Glu Glu
            355                 360                 365

Phe Asp Leu Gln Phe Ile Phe Gln Leu Cys Lys Ile Thr Leu Thr Ala
        370                 375                 380

Asp Val Met Thr Tyr Ile His Lys Met Asp Ala Thr Ile Leu Glu Asp
385                 390                 395                 400

Trp Gln Phe Gly Leu Thr Pro Pro Ser Ala Ser Leu Glu Asp Thr
                405                 410                 415

Tyr Arg Phe Val Thr Ser Thr Ala Ile Thr Cys Gln Lys Asn Thr Pro
                420                 425                 430

Pro Lys Gly Lys Glu Asp Pro Leu Lys Asp Tyr Met Phe Trp Glu Val
            435                 440                 445

Asp Leu Lys Glu Lys Phe Ser Ala Asp Leu Asp Gln Phe Pro Leu Gly
        450                 455                 460

Arg Lys Phe Leu Leu Gln Ala Gly Leu Gln Ala Arg Pro Lys Leu Lys
465                 470                 475                 480

Arg Pro Ala Ser Ser Ala Pro Arg Thr Ser Thr Lys Lys Lys Lys Val
                485                 490                 495

Lys Arg
```

<210> SEQ ID NO 5
<211> LENGTH: 497
<212> TYPE: PRT
<213> ORGANISM: Artificial sequence
<220> FEATURE:
<223> OTHER INFORMATION: Truncated HPV52 L1 protein

<400> SEQUENCE: 5

```
Met Glu Ala Thr Val Tyr Leu Pro Pro Val Pro Val Ser Lys Val Val
1               5                   10                  15

Ser Thr Asp Glu Tyr Val Ser Arg Thr Ser Ile Tyr Tyr Ala Gly
            20                  25                  30

Ser Ser Arg Leu Leu Thr Val Gly His Pro Tyr Phe Ser Ile Lys Asn
        35                  40                  45

Thr Ser Ser Gly Asn Gly Lys Lys Val Leu Val Pro Lys Val Ser Gly
    50                  55                  60

Leu Gln Tyr Arg Val Phe Arg Ile Lys Leu Pro Asp Pro Asn Lys Phe
65                  70                  75                  80

Gly Phe Pro Asp Thr Ser Phe Tyr Asn Pro Glu Thr Gln Arg Leu Val
                85                  90                  95

Trp Ala Cys Thr Gly Leu Glu Ile Gly Arg Gly Gln Pro Leu Gly Val
            100                 105                 110

Gly Ile Ser Gly His Pro Leu Leu Asn Lys Phe Asp Asp Thr Glu Thr
        115                 120                 125

Ser Asn Lys Tyr Ala Gly Lys Pro Gly Ile Asp Asn Arg Glu Cys Leu
    130                 135                 140

Ser Met Asp Tyr Lys Gln Thr Gln Leu Cys Ile Leu Gly Cys Lys Pro
145                 150                 155                 160

Pro Ile Gly Glu His Trp Gly Lys Gly Thr Pro Cys Asn Asn Asn Ser
                165                 170                 175

Gly Asn Pro Gly Asp Cys Pro Pro Leu Gln Leu Ile Asn Ser Val Ile
            180                 185                 190

Gln Asp Gly Asp Met Val Asp Thr Gly Phe Gly Cys Met Asp Phe Asn
        195                 200                 205

Thr Leu Gln Ala Ser Lys Ser Asp Val Pro Ile Asp Ile Cys Ser Ser
    210                 215                 220

Val Cys Lys Tyr Pro Asp Tyr Leu Gln Met Ala Ser Glu Pro Tyr Gly
225                 230                 235                 240

Asp Ser Leu Phe Phe Phe Leu Arg Arg Glu Gln Met Phe Val Arg His
                245                 250                 255

Phe Phe Asn Arg Ala Gly Thr Leu Gly Asp Pro Val Pro Gly Asp Leu
            260                 265                 270

Tyr Ile Gln Gly Ser Asn Ser Gly Asn Thr Ala Thr Val Gln Ser Ser
        275                 280                 285

Ala Phe Phe Pro Thr Pro Ser Gly Ser Met Val Thr Ser Glu Ser Gln
    290                 295                 300

Leu Phe Asn Lys Pro Tyr Trp Leu Gln Arg Ala Gln Gly His Asn Asn
305                 310                 315                 320

Gly Ile Cys Trp Gly Asn Gln Leu Phe Val Thr Val Val Asp Thr Thr
                325                 330                 335

Arg Ser Thr Asn Met Thr Leu Cys Ala Glu Val Lys Lys Glu Ser Thr
            340                 345                 350

Tyr Lys Asn Glu Asn Phe Lys Glu Tyr Leu Arg His Gly Glu Glu Phe
        355                 360                 365
```

```
Asp Leu Gln Phe Ile Phe Gln Leu Cys Lys Ile Thr Leu Thr Ala Asp
    370                 375                 380

Val Met Thr Tyr Ile His Lys Met Asp Ala Thr Ile Leu Glu Asp Trp
385                 390                 395                 400

Gln Phe Gly Leu Thr Pro Pro Ser Ala Ser Leu Glu Asp Thr Tyr
                    405                 410                 415

Arg Phe Val Thr Ser Thr Ala Ile Thr Cys Gln Lys Asn Thr Pro Pro
            420                 425                 430

Lys Gly Lys Glu Asp Pro Leu Lys Asp Tyr Met Phe Trp Glu Val Asp
        435                 440                 445

Leu Lys Glu Lys Phe Ser Ala Asp Leu Asp Gln Phe Pro Leu Gly Arg
450                 455                 460

Lys Phe Leu Leu Gln Ala Gly Leu Gln Ala Arg Pro Lys Leu Lys Arg
465                 470                 475                 480

Pro Ala Ser Ser Ala Pro Arg Thr Ser Thr Lys Lys Lys Val Lys
                    485                 490                 495

Arg

<210> SEQ ID NO 6
<211> LENGTH: 496
<212> TYPE: PRT
<213> ORGANISM: Artificial sequence
<220> FEATURE:
<223> OTHER INFORMATION: Truncated HPV52 L1 protein

<400> SEQUENCE: 6

Met Ala Thr Val Tyr Leu Pro Pro Val Pro Val Ser Lys Val Val Ser
1               5                   10                  15

Thr Asp Glu Tyr Val Ser Arg Thr Ser Ile Tyr Tyr Tyr Ala Gly Ser
            20                  25                  30

Ser Arg Leu Leu Thr Val Gly His Pro Tyr Phe Ser Ile Lys Asn Thr
        35                  40                  45

Ser Ser Gly Asn Gly Lys Lys Val Leu Val Pro Lys Val Ser Gly Leu
    50                  55                  60

Gln Tyr Arg Val Phe Arg Ile Lys Leu Pro Asp Pro Asn Lys Phe Gly
65                  70                  75                  80

Phe Pro Asp Thr Ser Phe Tyr Asn Pro Glu Thr Gln Arg Leu Val Trp
                85                  90                  95

Ala Cys Thr Gly Leu Glu Ile Gly Arg Gly Gln Pro Leu Gly Val Gly
            100                 105                 110

Ile Ser Gly His Pro Leu Leu Asn Lys Phe Asp Asp Thr Glu Thr Ser
        115                 120                 125

Asn Lys Tyr Ala Gly Lys Pro Gly Ile Asp Asn Arg Glu Cys Leu Ser
    130                 135                 140

Met Asp Tyr Lys Gln Thr Gln Leu Cys Ile Leu Gly Cys Lys Pro Pro
145                 150                 155                 160

Ile Gly Glu His Trp Gly Lys Gly Thr Pro Cys Asn Asn Asn Ser Gly
                165                 170                 175

Asn Pro Gly Asp Cys Pro Pro Leu Gln Leu Ile Asn Ser Val Ile Gln
            180                 185                 190

Asp Gly Asp Met Val Asp Thr Gly Phe Gly Cys Met Asp Phe Asn Thr
        195                 200                 205

Leu Gln Ala Ser Lys Ser Asp Val Pro Ile Asp Ile Cys Ser Ser Val
    210                 215                 220

Cys Lys Tyr Pro Asp Tyr Leu Gln Met Ala Ser Glu Pro Tyr Gly Asp
```

```
                    225                 230                 235                 240

Ser Leu Phe Phe Phe Leu Arg Arg Glu Gln Met Phe Val Arg His Phe
                245                 250                 255

Phe Asn Arg Ala Gly Thr Leu Gly Asp Pro Val Pro Gly Asp Leu Tyr
                260                 265                 270

Ile Gln Gly Ser Asn Ser Gly Asn Thr Ala Thr Val Gln Ser Ser Ala
                275                 280                 285

Phe Phe Pro Thr Pro Ser Gly Ser Met Val Thr Ser Glu Ser Gln Leu
290                 295                 300

Phe Asn Lys Pro Tyr Trp Leu Gln Arg Ala Gln Gly His Asn Asn Gly
305                 310                 315                 320

Ile Cys Trp Gly Asn Gln Leu Phe Val Thr Val Val Asp Thr Thr Arg
                325                 330                 335

Ser Thr Asn Met Thr Leu Cys Ala Glu Val Lys Lys Glu Ser Thr Tyr
                340                 345                 350

Lys Asn Glu Asn Phe Lys Glu Tyr Leu Arg His Gly Glu Glu Phe Asp
                355                 360                 365

Leu Gln Phe Ile Phe Gln Leu Cys Lys Ile Thr Leu Thr Ala Asp Val
                370                 375                 380

Met Thr Tyr Ile His Lys Met Asp Ala Thr Ile Leu Glu Asp Trp Gln
385                 390                 395                 400

Phe Gly Leu Thr Pro Pro Ser Ala Ser Leu Glu Asp Thr Tyr Arg
                405                 410                 415

Phe Val Thr Ser Thr Ala Ile Thr Cys Gln Lys Asn Thr Pro Pro Lys
                420                 425                 430

Gly Lys Glu Asp Pro Leu Lys Asp Tyr Met Phe Trp Glu Val Asp Leu
                435                 440                 445

Lys Glu Lys Phe Ser Ala Asp Leu Asp Gln Phe Pro Leu Gly Arg Lys
                450                 455                 460

Phe Leu Leu Gln Ala Gly Leu Gln Ala Arg Pro Lys Leu Lys Arg Pro
465                 470                 475                 480

Ala Ser Ser Ala Pro Arg Thr Ser Thr Lys Lys Lys Val Lys Arg
                485                 490                 495

<210> SEQ ID NO 7
<211> LENGTH: 495
<212> TYPE: PRT
<213> ORGANISM: Artificial sequence
<220> FEATURE:
<223> OTHER INFORMATION: Truncated HPV52 L1 protein

<400> SEQUENCE: 7

Met Thr Val Tyr Leu Pro Pro Val Pro Val Ser Lys Val Val Ser Thr
1               5                   10                  15

Asp Glu Tyr Val Ser Arg Thr Ser Ile Tyr Tyr Ala Gly Ser Ser
                20                  25                  30

Arg Leu Leu Thr Val Gly His Pro Tyr Phe Ser Ile Lys Asn Thr Ser
                35                  40                  45

Ser Gly Asn Gly Lys Lys Val Leu Val Pro Lys Val Ser Gly Leu Gln
                50                  55                  60

Tyr Arg Val Phe Arg Ile Lys Leu Pro Asp Pro Asn Lys Phe Gly Phe
65                  70                  75                  80

Pro Asp Thr Ser Phe Tyr Asn Pro Glu Thr Gln Arg Leu Val Trp Ala
                85                  90                  95

Cys Thr Gly Leu Glu Ile Gly Arg Gly Gln Pro Leu Gly Val Gly Ile
```

```
            100                 105                 110
Ser Gly His Pro Leu Leu Asn Lys Phe Asp Asp Thr Glu Thr Ser Asn
                115                 120                 125

Lys Tyr Ala Gly Lys Pro Gly Ile Asp Asn Arg Glu Cys Leu Ser Met
130                 135                 140

Asp Tyr Lys Gln Thr Gln Leu Cys Ile Leu Gly Cys Lys Pro Pro Ile
145                 150                 155                 160

Gly Glu His Trp Gly Lys Gly Thr Pro Cys Asn Asn Asn Ser Gly Asn
                165                 170                 175

Pro Gly Asp Cys Pro Pro Leu Gln Leu Ile Asn Ser Val Ile Gln Asp
            180                 185                 190

Gly Asp Met Val Asp Thr Gly Phe Gly Cys Met Asp Phe Asn Thr Leu
            195                 200                 205

Gln Ala Ser Lys Ser Asp Val Pro Ile Asp Ile Cys Ser Ser Val Cys
        210                 215                 220

Lys Tyr Pro Asp Tyr Leu Gln Met Ala Ser Glu Pro Tyr Gly Asp Ser
225                 230                 235                 240

Leu Phe Phe Phe Leu Arg Arg Glu Gln Met Phe Val Arg His Phe Phe
                245                 250                 255

Asn Arg Ala Gly Thr Leu Gly Asp Pro Val Pro Gly Asp Leu Tyr Ile
                260                 265                 270

Gln Gly Ser Asn Ser Gly Asn Thr Ala Thr Val Gln Ser Ser Ala Phe
            275                 280                 285

Phe Pro Thr Pro Ser Gly Ser Met Val Thr Ser Glu Ser Gln Leu Phe
            290                 295                 300

Asn Lys Pro Tyr Trp Leu Gln Arg Ala Gln Gly His Asn Asn Gly Ile
305                 310                 315                 320

Cys Trp Gly Asn Gln Leu Phe Val Thr Val Val Asp Thr Thr Arg Ser
                325                 330                 335

Thr Asn Met Thr Leu Cys Ala Glu Val Lys Lys Glu Ser Thr Tyr Lys
                340                 345                 350

Asn Glu Asn Phe Lys Glu Tyr Leu Arg His Gly Glu Glu Phe Asp Leu
                355                 360                 365

Gln Phe Ile Phe Gln Leu Cys Lys Ile Thr Leu Thr Ala Asp Val Met
        370                 375                 380

Thr Tyr Ile His Lys Met Asp Ala Thr Ile Leu Glu Asp Trp Gln Phe
385                 390                 395                 400

Gly Leu Thr Pro Pro Ser Ala Ser Leu Glu Asp Thr Tyr Arg Phe
                405                 410                 415

Val Thr Ser Thr Ala Ile Thr Cys Gln Lys Asn Thr Pro Pro Lys Gly
                420                 425                 430

Lys Glu Asp Pro Leu Lys Asp Tyr Met Phe Trp Glu Val Asp Leu Lys
            435                 440                 445

Glu Lys Phe Ser Ala Asp Leu Asp Gln Phe Pro Leu Gly Arg Lys Phe
        450                 455                 460

Leu Leu Gln Ala Gly Leu Gln Ala Arg Pro Lys Leu Lys Arg Pro Ala
465                 470                 475                 480

Ser Ser Ala Pro Arg Thr Ser Thr Lys Lys Lys Val Lys Arg
                485                 490                 495

<210> SEQ ID NO 8
<211> LENGTH: 494
<212> TYPE: PRT
<213> ORGANISM: Artificial sequence
```

<220> FEATURE:
<223> OTHER INFORMATION: Truncated HPV52 L1 protein

<400> SEQUENCE: 8

```
Met Val Tyr Leu Pro Pro Val Pro Val Ser Lys Val Val Ser Thr Asp
1               5                   10                  15

Glu Tyr Val Ser Arg Thr Ser Ile Tyr Tyr Ala Gly Ser Ser Arg
            20                  25                  30

Leu Leu Thr Val Gly His Pro Tyr Phe Ser Ile Lys Asn Thr Ser Ser
            35                  40                  45

Gly Asn Gly Lys Lys Val Leu Val Pro Lys Val Ser Gly Leu Gln Tyr
        50                  55                  60

Arg Val Phe Arg Ile Lys Leu Pro Asp Pro Asn Lys Phe Gly Phe Pro
65                  70                  75                  80

Asp Thr Ser Phe Tyr Asn Pro Glu Thr Gln Arg Leu Val Trp Ala Cys
                85                  90                  95

Thr Gly Leu Glu Ile Gly Arg Gly Gln Pro Leu Gly Val Gly Ile Ser
            100                 105                 110

Gly His Pro Leu Leu Asn Lys Phe Asp Asp Thr Glu Thr Ser Asn Lys
        115                 120                 125

Tyr Ala Gly Lys Pro Gly Ile Asp Asn Arg Glu Cys Leu Ser Met Asp
130                 135                 140

Tyr Lys Gln Thr Gln Leu Cys Ile Leu Gly Cys Lys Pro Pro Ile Gly
145                 150                 155                 160

Glu His Trp Gly Lys Gly Thr Pro Cys Asn Asn Asn Ser Gly Asn Pro
                165                 170                 175

Gly Asp Cys Pro Pro Leu Gln Leu Ile Asn Ser Val Ile Gln Asp Gly
            180                 185                 190

Asp Met Val Asp Thr Gly Phe Gly Cys Met Asp Phe Asn Thr Leu Gln
        195                 200                 205

Ala Ser Lys Ser Asp Val Pro Ile Asp Ile Cys Ser Ser Val Cys Lys
210                 215                 220

Tyr Pro Asp Tyr Leu Gln Met Ala Ser Glu Pro Tyr Gly Asp Ser Leu
225                 230                 235                 240

Phe Phe Phe Leu Arg Arg Glu Gln Met Phe Val Arg His Phe Phe Asn
                245                 250                 255

Arg Ala Gly Thr Leu Gly Asp Pro Val Pro Gly Asp Leu Tyr Ile Gln
            260                 265                 270

Gly Ser Asn Ser Gly Asn Thr Ala Thr Val Gln Ser Ser Ala Phe Phe
        275                 280                 285

Pro Thr Pro Ser Gly Ser Met Val Thr Ser Glu Ser Gln Leu Phe Asn
290                 295                 300

Lys Pro Tyr Trp Leu Gln Arg Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Glu Val Lys Lys Glu Ser Thr Tyr Lys Asn
            340                 345                 350

Glu Asn Phe Lys Glu Tyr Leu Arg His Gly Glu Glu Phe Asp Leu Gln
        355                 360                 365

Phe Ile Phe Gln Leu Cys Lys Ile Thr Leu Thr Ala Asp Val Met Thr
370                 375                 380

Tyr Ile His Lys Met Asp Ala Thr Ile Leu Glu Asp Trp Gln Phe Gly
385                 390                 395                 400
```

```
Leu Thr Pro Pro Ser Ala Ser Leu Glu Asp Thr Tyr Arg Phe Val
            405                 410                 415

Thr Ser Thr Ala Ile Thr Cys Gln Lys Asn Thr Pro Lys Gly Lys
            420                 425                 430

Glu Asp Pro Leu Lys Asp Tyr Met Phe Trp Glu Val Asp Leu Lys Glu
            435                 440                 445

Lys Phe Ser Ala Asp Leu Asp Gln Phe Pro Leu Gly Arg Lys Phe Leu
450                 455                 460

Leu Gln Ala Gly Leu Gln Ala Arg Pro Lys Leu Lys Arg Pro Ala Ser
465                 470                 475                 480

Ser Ala Pro Arg Thr Ser Thr Lys Lys Lys Val Lys Arg
                485                 490

<210> SEQ ID NO 9
<211> LENGTH: 493
<212> TYPE: PRT
<213> ORGANISM: Artificial sequence
<220> FEATURE:
<223> OTHER INFORMATION: Truncated HPV52 L1 protein

<400> SEQUENCE: 9

Met Tyr Leu Pro Pro Val Pro Val Ser Lys Val Val Ser Thr Asp Glu
1               5                   10                  15

Tyr Val Ser Arg Thr Ser Ile Tyr Tyr Tyr Ala Gly Ser Ser Arg Leu
            20                  25                  30

Leu Thr Val Gly His Pro Tyr Phe Ser Ile Lys Asn Thr Ser Ser Gly
        35                  40                  45

Asn Gly Lys Lys Val Leu Val Pro Lys Val Ser Gly Leu Gln Tyr Arg
50                  55                  60

Val Phe Arg Ile Lys Leu Pro Asp Pro Asn Lys Phe Gly Phe Pro Asp
65                  70                  75                  80

Thr Ser Phe Tyr Asn Pro Glu Thr Gln Arg Leu Val Trp Ala Cys Thr
                85                  90                  95

Gly Leu Glu Ile Gly Arg Gly Gln Pro Leu Gly Val Gly Ile Ser Gly
            100                 105                 110

His Pro Leu Leu Asn Lys Phe Asp Asp Thr Glu Thr Ser Asn Lys Tyr
        115                 120                 125

Ala Gly Lys Pro Gly Ile Asp Asn Arg Glu Cys Leu Ser Met Asp Tyr
    130                 135                 140

Lys Gln Thr Gln Leu Cys Ile Leu Gly Cys Lys Pro Pro Ile Gly Glu
145                 150                 155                 160

His Trp Gly Lys Gly Thr Pro Cys Asn Asn Asn Ser Gly Asn Pro Gly
                165                 170                 175

Asp Cys Pro Pro Leu Gln Leu Ile Asn Ser Val Ile Gln Asp Gly Asp
            180                 185                 190

Met Val Asp Thr Gly Phe Gly Cys Met Asp Phe Asn Thr Leu Gln Ala
        195                 200                 205

Ser Lys Ser Asp Val Pro Ile Asp Ile Cys Ser Ser Val Cys Lys Tyr
    210                 215                 220

Pro Asp Tyr Leu Gln Met Ala Ser Glu Pro Tyr Gly Asp Ser Leu Phe
225                 230                 235                 240

Phe Phe Leu Arg Arg Glu Gln Met Phe Val Arg His Phe Phe Asn Arg
                245                 250                 255

Ala Gly Thr Leu Gly Asp Pro Val Pro Gly Asp Leu Tyr Ile Gln Gly
            260                 265                 270
```

Ser Asn Ser Gly Asn Thr Ala Thr Val Gln Ser Ser Ala Phe Phe Pro
            275                 280                 285

Thr Pro Ser Gly Ser Met Val Thr Ser Glu Ser Gln Leu Phe Asn Lys
            290                 295                 300

Pro Tyr Trp Leu Gln Arg Ala Gln Gly His Asn Asn Gly Ile Cys Trp
305                 310                 315                 320

Gly Asn Gln Leu Phe Val Thr Val Val Asp Thr Thr Arg Ser Thr Asn
            325                 330                 335

Met Thr Leu Cys Ala Glu Val Lys Lys Glu Ser Thr Tyr Lys Asn Glu
            340                 345                 350

Asn Phe Lys Glu Tyr Leu Arg His Gly Glu Glu Phe Asp Leu Gln Phe
            355                 360                 365

Ile Phe Gln Leu Cys Lys Ile Thr Leu Thr Ala Asp Val Met Thr Tyr
            370                 375                 380

Ile His Lys Met Asp Ala Thr Ile Leu Glu Asp Trp Gln Phe Gly Leu
385                 390                 395                 400

Thr Pro Pro Pro Ser Ala Ser Leu Glu Asp Thr Tyr Arg Phe Val Thr
            405                 410                 415

Ser Thr Ala Ile Thr Cys Gln Lys Asn Thr Pro Pro Lys Gly Lys Glu
            420                 425                 430

Asp Pro Leu Lys Asp Tyr Met Phe Trp Glu Val Asp Leu Lys Glu Lys
            435                 440                 445

Phe Ser Ala Asp Leu Asp Gln Phe Pro Leu Gly Arg Lys Phe Leu Leu
450                 455                 460

Gln Ala Gly Leu Gln Ala Arg Pro Lys Leu Lys Arg Pro Ala Ser Ser
465                 470                 475                 480

Ala Pro Arg Thr Ser Thr Lys Lys Lys Val Lys Arg
            485                 490

<210> SEQ ID NO 10
<211> LENGTH: 492
<212> TYPE: PRT
<213> ORGANISM: Artificial sequence
<220> FEATURE:
<223> OTHER INFORMATION: Truncated HPV52 L1 protein

<400> SEQUENCE: 10

Met Leu Pro Pro Val Pro Val Ser Lys Val Val Ser Thr Asp Glu Tyr
1               5                   10                  15

Val Ser Arg Thr Ser Ile Tyr Tyr Ala Gly Ser Ser Arg Leu Leu
            20                  25                  30

Thr Val Gly His Pro Tyr Phe Ser Ile Lys Asn Thr Ser Ser Gly Asn
            35                  40                  45

Gly Lys Lys Val Leu Val Pro Lys Val Ser Gly Leu Gln Tyr Arg Val
        50                  55                  60

Phe Arg Ile Lys Leu Pro Asp Pro Asn Lys Phe Gly Phe Pro Asp Thr
65                  70                  75                  80

Ser Phe Tyr Asn Pro Glu Thr Gln Arg Leu Val Trp Ala Cys Thr Gly
            85                  90                  95

Leu Glu Ile Gly Arg Gly Gln Pro Leu Gly Val Gly Ile Ser Gly His
            100                 105                 110

Pro Leu Leu Asn Lys Phe Asp Asp Thr Glu Thr Ser Asn Lys Tyr Ala
        115                 120                 125

Gly Lys Pro Gly Ile Asp Asn Arg Glu Cys Leu Ser Met Asp Tyr Lys
        130                 135                 140

Gln Thr Gln Leu Cys Ile Leu Gly Cys Lys Pro Ile Gly Glu His
145                 150                 155                 160

Trp Gly Lys Gly Thr Pro Cys Asn Asn Asn Ser Gly Asn Pro Gly Asp
                165                 170                 175

Cys Pro Pro Leu Gln Leu Ile Asn Ser Val Ile Gln Asp Gly Asp Met
            180                 185                 190

Val Asp Thr Gly Phe Gly Cys Met Asp Phe Asn Thr Leu Gln Ala Ser
        195                 200                 205

Lys Ser Asp Val Pro Ile Asp Ile Cys Ser Ser Val Cys Lys Tyr Pro
    210                 215                 220

Asp Tyr Leu Gln Met Ala Ser Glu Pro Tyr Gly Asp Ser Leu Phe Phe
225                 230                 235                 240

Phe Leu Arg Arg Glu Gln Met Phe Val Arg His Phe Phe Asn Arg Ala
                245                 250                 255

Gly Thr Leu Gly Asp Pro Val Pro Gly Asp Leu Tyr Ile Gln Gly Ser
            260                 265                 270

Asn Ser Gly Asn Thr Ala Thr Val Gln Ser Ser Ala Phe Phe Pro Thr
        275                 280                 285

Pro Ser Gly Ser Met Val Thr Ser Glu Ser Gln Leu Phe Asn Lys Pro
    290                 295                 300

Tyr Trp Leu Gln Arg Ala Gln Gly His Asn Asn Gly Ile Cys Trp Gly
305                 310                 315                 320

Asn Gln Leu Phe Val Thr Val Val Asp Thr Thr Arg Ser Thr Asn Met
                325                 330                 335

Thr Leu Cys Ala Glu Val Lys Lys Glu Ser Thr Tyr Lys Asn Glu Asn
            340                 345                 350

Phe Lys Glu Tyr Leu Arg His Gly Glu Glu Phe Asp Leu Gln Phe Ile
        355                 360                 365

Phe Gln Leu Cys Lys Ile Thr Leu Thr Ala Asp Val Met Thr Tyr Ile
    370                 375                 380

His Lys Met Asp Ala Thr Ile Leu Glu Asp Trp Gln Phe Gly Leu Thr
385                 390                 395                 400

Pro Pro Pro Ser Ala Ser Leu Glu Asp Thr Tyr Arg Phe Val Thr Ser
                405                 410                 415

Thr Ala Ile Thr Cys Gln Lys Asn Thr Pro Pro Lys Gly Lys Glu Asp
            420                 425                 430

Pro Leu Lys Asp Tyr Met Phe Trp Glu Val Asp Leu Lys Glu Lys Phe
        435                 440                 445

Ser Ala Asp Leu Asp Gln Phe Pro Leu Gly Arg Lys Phe Leu Leu Gln
    450                 455                 460

Ala Gly Leu Gln Ala Arg Pro Lys Leu Lys Arg Pro Ala Ser Ser Ala
465                 470                 475                 480

Pro Arg Thr Ser Thr Lys Lys Lys Val Lys Arg
                485                 490

<210> SEQ ID NO 11
<211> LENGTH: 491
<212> TYPE: PRT
<213> ORGANISM: Artificial sequence
<220> FEATURE:
<223> OTHER INFORMATION: Truncated HPV52 L1 protein

<400> SEQUENCE: 11

Met Pro Pro Val Pro Val Ser Lys Val Val Ser Thr Asp Glu Tyr Val
1               5                   10                  15

Ser Arg Thr Ser Ile Tyr Tyr Ala Gly Ser Ser Arg Leu Leu Thr
            20                  25                  30

Val Gly His Pro Tyr Phe Ser Ile Lys Asn Thr Ser Ser Gly Asn Gly
        35                  40                  45

Lys Lys Val Leu Val Pro Lys Val Ser Gly Leu Gln Tyr Arg Val Phe
 50                  55                  60

Arg Ile Lys Leu Pro Asp Pro Asn Lys Phe Gly Phe Pro Asp Thr Ser
 65                  70                  75                  80

Phe Tyr Asn Pro Glu Thr Gln Arg Leu Val Trp Ala Cys Thr Gly Leu
                85                  90                  95

Glu Ile Gly Arg Gly Gln Pro Leu Gly Val Gly Ile Ser Gly His Pro
            100                 105                 110

Leu Leu Asn Lys Phe Asp Asp Thr Glu Thr Ser Asn Lys Tyr Ala Gly
        115                 120                 125

Lys Pro Gly Ile Asp Asn Arg Glu Cys Leu Ser Met Asp Tyr Lys Gln
130                 135                 140

Thr Gln Leu Cys Ile Leu Gly Cys Lys Pro Pro Ile Gly Glu His Trp
145                 150                 155                 160

Gly Lys Gly Thr Pro Cys Asn Asn Asn Ser Gly Asn Pro Gly Asp Cys
                165                 170                 175

Pro Pro Leu Gln Leu Ile Asn Ser Val Ile Gln Asp Gly Asp Met Val
            180                 185                 190

Asp Thr Gly Phe Gly Cys Met Asp Phe Asn Thr Leu Gln Ala Ser Lys
        195                 200                 205

Ser Asp Val Pro Ile Asp Ile Cys Ser Ser Val Cys Lys Tyr Pro Asp
        210                 215                 220

Tyr Leu Gln Met Ala Ser Glu Pro Tyr Gly Asp Ser Leu Phe Phe Phe
225                 230                 235                 240

Leu Arg Arg Glu Gln Met Phe Val Arg His Phe Phe Asn Arg Ala Gly
            245                 250                 255

Thr Leu Gly Asp Pro Val Pro Gly Asp Leu Tyr Ile Gln Gly Ser Asn
        260                 265                 270

Ser Gly Asn Thr Ala Thr Val Gln Ser Ser Ala Phe Phe Pro Thr Pro
    275                 280                 285

Ser Gly Ser Met Val Thr Ser Glu Ser Gln Leu Phe Asn Lys Pro Tyr
290                 295                 300

Trp Leu Gln Arg Ala Gln Gly His Asn Asn Gly Ile Cys Trp Gly Asn
305                 310                 315                 320

Gln Leu Phe Val Thr Val Val Asp Thr Thr Arg Ser Thr Asn Met Thr
            325                 330                 335

Leu Cys Ala Glu Val Lys Lys Glu Ser Thr Tyr Lys Asn Glu Asn Phe
        340                 345                 350

Lys Glu Tyr Leu Arg His Gly Glu Glu Phe Asp Leu Gln Phe Ile Phe
        355                 360                 365

Gln Leu Cys Lys Ile Thr Leu Thr Ala Asp Val Met Thr Tyr Ile His
        370                 375                 380

Lys Met Asp Ala Thr Ile Leu Glu Asp Trp Gln Phe Gly Leu Thr Pro
385                 390                 395                 400

Pro Pro Ser Ala Ser Leu Glu Asp Thr Tyr Arg Phe Val Thr Ser Thr
            405                 410                 415

Ala Ile Thr Cys Gln Lys Asn Thr Pro Pro Lys Gly Lys Glu Asp Pro
        420                 425                 430

```
Leu Lys Asp Tyr Met Phe Trp Glu Val Asp Leu Lys Glu Lys Phe Ser
            435                 440                 445

Ala Asp Leu Asp Gln Phe Pro Leu Gly Arg Lys Phe Leu Leu Gln Ala
450                 455                 460

Gly Leu Gln Ala Arg Pro Lys Leu Lys Arg Pro Ala Ser Ser Ala Pro
465                 470                 475                 480

Arg Thr Ser Thr Lys Lys Lys Val Lys Arg
                485                 490

<210> SEQ ID NO 12
<211> LENGTH: 490
<212> TYPE: PRT
<213> ORGANISM: Artificial sequence
<220> FEATURE:
<223> OTHER INFORMATION: Truncated HPV52 L1 protein

<400> SEQUENCE: 12

Met Pro Val Pro Val Ser Lys Val Val Ser Thr Asp Glu Tyr Val Ser
1               5                   10                  15

Arg Thr Ser Ile Tyr Tyr Ala Gly Ser Ser Arg Leu Leu Thr Val
            20                  25                  30

Gly His Pro Tyr Phe Ser Ile Lys Asn Thr Ser Ser Gly Asn Gly Lys
            35                  40                  45

Lys Val Leu Val Pro Lys Val Ser Gly Leu Gln Tyr Arg Val Phe Arg
50                  55                  60

Ile Lys Leu Pro Asp Pro Asn Lys Phe Gly Phe Pro Asp Thr Ser Phe
65                  70                  75                  80

Tyr Asn Pro Glu Thr Gln Arg Leu Val Trp Ala Cys Thr Gly Leu Glu
                85                  90                  95

Ile Gly Arg Gly Gln Pro Leu Gly Val Gly Ile Ser Gly His Pro Leu
            100                 105                 110

Leu Asn Lys Phe Asp Asp Thr Glu Thr Ser Asn Lys Tyr Ala Gly Lys
            115                 120                 125

Pro Gly Ile Asp Asn Arg Glu Cys Leu Ser Met Asp Tyr Lys Gln Thr
130                 135                 140

Gln Leu Cys Ile Leu Gly Cys Lys Pro Pro Ile Gly Glu His Trp Gly
145                 150                 155                 160

Lys Gly Thr Pro Cys Asn Asn Asn Ser Gly Asn Pro Gly Asp Cys Pro
                165                 170                 175

Pro Leu Gln Leu Ile Asn Ser Val Ile Gln Asp Gly Asp Met Val Asp
            180                 185                 190

Thr Gly Phe Gly Cys Met Asp Phe Asn Thr Leu Gln Ala Ser Lys Ser
            195                 200                 205

Asp Val Pro Ile Asp Ile Cys Ser Ser Val Cys Lys Tyr Pro Asp Tyr
210                 215                 220

Leu Gln Met Ala Ser Glu Pro Tyr Gly Asp Ser Leu Phe Phe Phe Leu
225                 230                 235                 240

Arg Arg Glu Gln Met Phe Val Arg His Phe Phe Asn Arg Ala Gly Thr
                245                 250                 255

Leu Gly Asp Pro Val Pro Gly Asp Leu Tyr Ile Gln Gly Ser Asn Ser
            260                 265                 270

Gly Asn Thr Ala Thr Val Gln Ser Ser Ala Phe Phe Pro Thr Pro Ser
            275                 280                 285

Gly Ser Met Val Thr Ser Glu Ser Gln Leu Phe Asn Lys Pro Tyr Trp
290                 295                 300
```

```
Leu Gln Arg Ala Gln Gly His Asn Asn Gly Ile Cys Trp Gly Asn Gln
305                 310                 315                 320

Leu Phe Val Thr Val Val Asp Thr Thr Arg Ser Thr Asn Met Thr Leu
            325                 330                 335

Cys Ala Glu Val Lys Lys Glu Ser Thr Tyr Lys Asn Glu Asn Phe Lys
            340                 345                 350

Glu Tyr Leu Arg His Gly Glu Glu Phe Asp Leu Gln Phe Ile Phe Gln
        355                 360                 365

Leu Cys Lys Ile Thr Leu Thr Ala Asp Val Met Thr Tyr Ile His Lys
370                 375                 380

Met Asp Ala Thr Ile Leu Glu Asp Trp Gln Phe Gly Leu Thr Pro Pro
385                 390                 395                 400

Pro Ser Ala Ser Leu Glu Asp Thr Tyr Arg Phe Val Thr Ser Thr Ala
            405                 410                 415

Ile Thr Cys Gln Lys Asn Thr Pro Pro Lys Gly Lys Glu Asp Pro Leu
            420                 425                 430

Lys Asp Tyr Met Phe Trp Glu Val Asp Leu Lys Glu Lys Phe Ser Ala
        435                 440                 445

Asp Leu Asp Gln Phe Pro Leu Gly Arg Lys Phe Leu Leu Gln Ala Gly
450                 455                 460

Leu Gln Ala Arg Pro Lys Leu Lys Arg Pro Ala Ser Ser Ala Pro Arg
465                 470                 475                 480

Thr Ser Thr Lys Lys Lys Lys Val Lys Arg
            485                 490

<210> SEQ ID NO 13
<211> LENGTH: 488
<212> TYPE: PRT
<213> ORGANISM: Artificial sequence
<220> FEATURE:
<223> OTHER INFORMATION: Truncated HPV52 L1 protein

<400> SEQUENCE: 13

Met Pro Val Ser Lys Val Val Ser Thr Asp Glu Tyr Val Ser Arg Thr
1               5                   10                  15

Ser Ile Tyr Tyr Tyr Ala Gly Ser Ser Arg Leu Leu Thr Val Gly His
            20                  25                  30

Pro Tyr Phe Ser Ile Lys Asn Thr Ser Ser Gly Asn Gly Lys Lys Val
        35                  40                  45

Leu Val Pro Lys Val Ser Gly Leu Gln Tyr Arg Val Phe Arg Ile Lys
    50                  55                  60

Leu Pro Asp Pro Asn Lys Phe Gly Phe Pro Asp Thr Ser Phe Tyr Asn
65                  70                  75                  80

Pro Glu Thr Gln Arg Leu Val Trp Ala Cys Thr Gly Leu Glu Ile Gly
                85                  90                  95

Arg Gly Gln Pro Leu Gly Val Gly Ile Ser Gly His Pro Leu Leu Asn
            100                 105                 110

Lys Phe Asp Asp Thr Glu Thr Ser Asn Lys Tyr Ala Gly Lys Pro Gly
        115                 120                 125

Ile Asp Asn Arg Glu Cys Leu Ser Met Asp Tyr Lys Gln Thr Gln Leu
    130                 135                 140

Cys Ile Leu Gly Cys Lys Pro Pro Ile Gly Glu His Trp Gly Lys Gly
145                 150                 155                 160

Thr Pro Cys Asn Asn Asn Ser Gly Asn Pro Gly Asp Cys Pro Pro Leu
                165                 170                 175
```

```
Gln Leu Ile Asn Ser Val Ile Gln Asp Gly Asp Met Val Asp Thr Gly
                180                 185                 190

Phe Gly Cys Met Asp Phe Asn Thr Leu Gln Ala Ser Lys Ser Asp Val
            195                 200                 205

Pro Ile Asp Ile Cys Ser Ser Val Cys Lys Tyr Pro Asp Tyr Leu Gln
        210                 215                 220

Met Ala Ser Glu Pro Tyr Gly Asp Ser Leu Phe Phe Leu Arg Arg
225                 230                 235                 240

Glu Gln Met Phe Val Arg His Phe Asn Arg Ala Gly Thr Leu Gly
                245                 250                 255

Asp Pro Val Pro Gly Asp Leu Tyr Ile Gln Gly Ser Asn Ser Gly Asn
            260                 265                 270

Thr Ala Thr Val Gln Ser Ser Ala Phe Phe Pro Thr Pro Ser Gly Ser
        275                 280                 285

Met Val Thr Ser Glu Ser Gln Leu Phe Asn Lys Pro Tyr Trp Leu Gln
290                 295                 300

Arg Ala Gln Gly His Asn Asn Gly Ile Cys Trp Gly Asn Gln Leu Phe
305                 310                 315                 320

Val Thr Val Val Asp Thr Thr Arg Ser Thr Asn Met Thr Leu Cys Ala
                325                 330                 335

Glu Val Lys Lys Glu Ser Thr Tyr Lys Asn Glu Asn Phe Lys Glu Tyr
            340                 345                 350

Leu Arg His Gly Glu Glu Phe Asp Leu Gln Phe Ile Phe Gln Leu Cys
        355                 360                 365

Lys Ile Thr Leu Thr Ala Asp Val Met Thr Tyr Ile His Lys Met Asp
370                 375                 380

Ala Thr Ile Leu Glu Asp Trp Gln Phe Gly Leu Thr Pro Pro Pro Ser
385                 390                 395                 400

Ala Ser Leu Glu Asp Thr Tyr Arg Phe Val Thr Ser Thr Ala Ile Thr
                405                 410                 415

Cys Gln Lys Asn Thr Pro Pro Lys Gly Lys Glu Asp Pro Leu Lys Asp
            420                 425                 430

Tyr Met Phe Trp Glu Val Asp Leu Lys Glu Lys Phe Ser Ala Asp Leu
        435                 440                 445

Asp Gln Phe Pro Leu Gly Arg Lys Phe Leu Leu Gln Ala Gly Leu Gln
450                 455                 460

Ala Arg Pro Lys Leu Lys Arg Pro Ala Ser Ser Ala Pro Arg Thr Ser
465                 470                 475                 480

Thr Lys Lys Lys Lys Val Lys Arg
                485

<210> SEQ ID NO 14
<211> LENGTH: 1512
<212> TYPE: DNA
<213> ORGANISM: Artificial sequence
<220> FEATURE:
<223> OTHER INFORMATION: Truncated HPV52 L1 gene

<400> SEQUENCE: 14
atgagcgtgt ggaggcccag cgaggccacc gtgtacctgc ccccgtgcc cgtgagcaag      60 gtggtgagca ccgacgagta cgtgagcagg accagcatct actactacgc cggcagcagc     120
aggctgctga ccgtgggcca ccctacttc agcatcaaga acaccagcag cggcaacggc     180
aagaaggtgc tggtgcccaa ggtgagcggc ctgcagtaca gggtgttcag gatcaagctg     240
cccgacccca acaagttcgg cttccccgac accagcttct acaaccccga gacccagagg     300
```

| | |
|---|---|
| ctggtgtggg cctgcaccgg cctggagatc ggcaggggcc agcccctggg cgtgggcatc | 360 |
| agcggccacc ccctgctgaa caagttcgac gacaccgaga ccagcaacaa gtacgccggc | 420 |
| aagcccggca tcgacaacag ggagtgcctg agcatggact acaagcagac ccagctgtgc | 480 |
| atcctgggct gcaagccccc catcggcgag cactggggca agggcacccc ctgcaacaac | 540 |
| aacagcggca accccggcga ctgcccccc ctgcagctga tcaacagcgt gatccaggac | 600 |
| ggcgacatgg tggacaccgg cttcggctgc atggacttca acaccctgca ggccagcaag | 660 |
| agcgacgtgc ccatcgacat ctgcagcagc gtgtgcaagt accccgacta cctgcagatg | 720 |
| gccagcgagc cctacggcga cagcctgttc ttcttcctga gggaggagca gatgttcgtg | 780 |
| aggcacttct tcaacagggc cggcacccct ggcgaccccg tgcccggcga cctgtacatc | 840 |
| cagggcagca cagcggcaa caccgccacc gtgcagagca gcgccttctt ccccacccc | 900 |
| agcggcagca tggtgaccag cgagagccag ctgttcaaca gccctactg gctgcagagg | 960 |
| gcccaggggcc acaacaacgg catctgctgg ggcaaccagc tgttcgtgac cgtggtggac | 1020 |
| accaccagga gcaccaacat gaccctgtgc gccgaggtga agaaggagag cacctacaag | 1080 |
| aacgagaact tcaaggagta cctgaggcac ggcgaggagt tcgacctgca gttcatcttc | 1140 |
| cagctgtgca agatcaccct gaccgccgac gtgatgacct acatccacaa gatggacgcc | 1200 |
| accatcctgg aggactggca gttcggcctg accccccccc ccagcgccag cctggaggac | 1260 |
| acctacaggt tcgtgaccag caccgccatc acctgccaga gaacacccc cccaagggc | 1320 |
| aaggaggacc ccctgaagga ctacatgttc tgggaggtgg acctgaagga aagttcagc | 1380 |
| gccgacctgg accagttccc cctgggcagg aagttcctgc tgcaggccgg cctgcaggcc | 1440 |
| aggcccaagc tgaagaggcc cgccagcagc gcccccagga ccagcaccaa gaagaagaag | 1500 |
| gtgaagaggt ga | 1512 |

<210> SEQ ID NO 15
<211> LENGTH: 1503
<212> TYPE: DNA
<213> ORGANISM: Artificial sequence
<220> FEATURE:
<223> OTHER INFORMATION: Truncated HPV52 L1 gene

<400> SEQUENCE: 15

| | |
|---|---|
| atgaggccca gcgaggccac cgtgtacctg cccccgtgc ccgtgagcaa ggtggtgagc | 60 |
| accgacgagt acgtgagcag gaccagcatc tactactacg ccggcagcag caggctgctg | 120 |
| accgtgggcc acccctactt cagcatcaag aacaccagca gcggcaacgg caagaaggtg | 180 |
| ctggtgccca aggtgagcgg cctgcagtac agggtgttca ggatcaagct gcccgacccc | 240 |
| aacaagttcg gcttccccga caccagcttc tacaaccccg agacccagag gctggtgtgg | 300 |
| gcctgcaccg gcctggagat cggcaggggc cagcccctgg gcgtgggcat cagcggccac | 360 |
| cccctgctga caagttcga cgacaccgag accagcaaca gtacgccgg caagcccggc | 420 |
| atcgacaaca gggagtgcct gagcatggac tacaagcaga cccagctgtg catcctgggc | 480 |
| tgcaagcccc ccatcggcga gcactggggc aagggcaccc cctgcaacaa caacagcggc | 540 |
| aaccccggcg actgccccc cctgcagctg atcaacagc tgatccagga cggcgacatg | 600 |
| gtggacaccg gcttcggctg catggacttc aacaccctgc aggccagcaa gagcgacgtg | 660 |
| cccatcgaca tctgcagcag cgtgtgcaag taccccgact acctgcagat ggccagcgag | 720 |
| ccctacggcg acagcctgtt cttcttcctg aggagggagc agatgttcgt gaggcacttc | 780 |

| | |
|---|---|
| ttcaacaggg ccggcaccct gggcgacccc gtgcccggcg acctgtacat ccagggcagc | 840 |
| aacagcggca acaccgccac cgtgcagagc agcgccttct tccccacccc cagcggcagc | 900 |
| atggtgacca gcgagagcca gctgttcaac aagcccctact ggctgcagag ggcccagggc | 960 |
| cacaacaacg gcatctgctg gggcaaccag ctgttcgtga ccgtggtgga caccaccagg | 1020 |
| agcaccaaca tgaccctgtg cgccgaggtg aagaaggaga gcacctacaa gaacgagaac | 1080 |
| ttcaaggagt acctgaggca cggcgaggag ttcgacctgc agttcatctt ccagctgtgc | 1140 |
| aagatcaccc tgaccgccga cgtgatgacc tacatccaca gatggacgc caccatcctg | 1200 |
| gaggactggc agttcggcct gacccccccc cccagcgcca gcctggagga cacctacagg | 1260 |
| ttcgtgacca gcaccgccat cacctgccag aagaacaccc ccccaagggg caaggaggac | 1320 |
| cccctgaagg actacatgtt ctgggaggtg gacctgaagg agaagttcag cgccgacctg | 1380 |
| gaccagttcc ccctgggcag gaagttcctg ctgcaggccg cctgcaggc caggcccaag | 1440 |
| ctgaagaggc ccgccagcag cgcccccagg accagcacca gaagaagaa ggtgaagagg | 1500 |
| tga | 1503 |

<210> SEQ ID NO 16
<211> LENGTH: 1500
<212> TYPE: DNA
<213> ORGANISM: Artificial sequence
<220> FEATURE:
<223> OTHER INFORMATION: Truncated HPV52 L1 gene

<400> SEQUENCE: 16

| | |
|---|---|
| atgcccagcg aggccaccgt gtacctgccc ccgtgcccg tgagcaaggt ggtgagcacc | 60 |
| gacgagtacg tgagcaggac cagcatctac tactacgccg gcagcagcag gctgctgacc | 120 |
| gtgggccacc cctacttcag catcaagaac accagcagcg gcaacggcaa gaaggtgctg | 180 |
| gtgcccaagg tgagcggcct gcagtacagg gtgttcagga tcaagctgcc cgaccccaac | 240 |
| aagttcggct tccccgacac cagcttctac aaccccgaga cccagaggct ggtgtgggcc | 300 |
| tgcaccggcc tggagatcgg caggggccag cccctgggcg tgggcatcag cggccacccc | 360 |
| ctgctgaaca gttcgacga caccgagacc agcaacaagt acgccggcaa gcccggcatc | 420 |
| gacaacaggg agtgcctgag catggactac aagcagaccc agctgtgcat cctgggctgc | 480 |
| aagcccccca tcggcgagca ctggggcaag ggcacccct gcaacaacaa cagcggcaac | 540 |
| cccgcgact gccccccct gcagctgatc aacagcgtga tccaggacgg cgacatggtg | 600 |
| gacaccggct cggctgcat ggacttcaac accctgcagg ccagcaagag cgacgtgccc | 660 |
| atcgacatct gcagcagcgt gtgcaagtac cccgactacc tgcagatggc cagcgagccc | 720 |
| tacgccgaca gcctgttctt cttcctgagg agggagcaga tgttcgtgag gcacttcttc | 780 |
| aacagggccg gcacctgggg cgaccccgtg cccggcgacc tgtacatcca gggcagcaac | 840 |
| agcggcaaca ccgccaccgt gcagagcagc gccttcttcc caccccag cggcagcatg | 900 |
| gtgaccagcg agagccagct gttcaacaag ccctactggc tgcagagggc cagggccac | 960 |
| aacaacggca tctgctgggg caaccagctg ttcgtgaccg tggtggacac caccaggagc | 1020 |
| accaacatga ccctgtgcgc cgaggtgaag aaggagagca cctacaagaa cgagaacttc | 1080 |
| aaggagtacc tgaggcacgg cgaggagttc gacctgcagt tcatcttcca gctgtgcaag | 1140 |
| atcaccctga ccgccgacgt gatgacctac atccacaaga tggacgccac catcctggag | 1200 |
| gactggcagt tcggcctgac cccccccc agcgccagcc tggaggacac ctacaggttc | 1260 |
| gtgaccagca ccgccatcac ctgccagaag aacacccccc caagggcaa ggaggacccc | 1320 |

```
ctgaaggact acatgttctg ggaggtggac ctgaaggaga agttcagcgc cgacctggac      1380
cagttccccc tgggcaggaa gttcctgctg caggccggcc tgcaggccag cccaagctg       1440 aagaggcccg ccagcagcgc ccccaggacc agcaccaaga agaagaaggt gaagaggtga      1500
```

<210> SEQ ID NO 17
<211> LENGTH: 1497
<212> TYPE: DNA
<213> ORGANISM: Artificial sequence
<220> FEATURE:
<223> OTHER INFORMATION: Truncated HPV52 L1 gene

<400> SEQUENCE: 17

```
atgagcgagg ccaccgtgta cctgcccccc gtgcccgtga gcaaggtggt gagcaccgac        60
gagtacgtga gcaggaccag catctactac tacgccggca gcagcaggct gctgaccgtg       120
ggccacccct acttcagcat caagaacacc agcagcggca cggcaagaa ggtgctggtg        180 cccaaggtga gcggcctgca gtacagggtg ttcaggatca agctgcccga ccccaacaag       240
ttcggcttcc ccgacaccag cttctacaac cccgagaccc agaggctggt gtgggcctgc       300
accggcctgg agatcggcag gggccagccc tgggcgtgg gcatcagcgg ccacccctg        360 ctgaacaagt tcgacgacac cgagaccagc aacaagtacg ccggcaagcc cggcatcgac       420
aacagggagt gcctgagcat ggactacaag cagacccagc tgtgcatcct gggctgcaag       480
ccccccatcg gcgagcactg gggcaagggc acccctgca caacaacag cggcaaccc        540 ggcgactgcc cccccctgca gctgatcaac agcgtgatcc aggacggcga catggtggac       600
accggcttcg gctgcatgga cttcaacacc ctgcaggcca gcaagagcga cgtgcccatc       660
gacatctgca gcagcgtgtg caagtacccc gactacctgc agatggccag cgagcctac       720 ggcgacagcc tgttcttctt cctgaggagg gagcagatgt tcgtgaggca cttcttcaac       780
agggccggca cctgggcga ccccgtgccc ggcgacctgt acatccaggg cagcaacagc       840
ggcaacaccg ccaccgtgca gagcagcgcc ttcttcccca cccccagcgg cagcatggtg       900
accagcgaga gccagctgtt caacaagccc tactggctgc agagggccca gggccacaac       960
aacggcatct gctgggcaa ccagctgttc gtgaccgtgg tggacaccac caggagcacc       1020
aacatgaccc tgtgcgccga ggtgaagaag gagagcacct acaagaacga gaacttcaag       1080
gagtacctga gcacggcga ggagttcgac ctgcagttca tcttccagct gtgcaagatc       1140 acccctgaccg ccgacgtgat gacctacatc cacaagatgg acgccaccat cctggaggac       1200
tggcagttcg gcctgacccc cccccccagc gccagcctgg aggacaccta caggttcgtg       1260
accagcaccg ccatcacctg ccagaagaac cccccccca agggcaagga ggacccctg        1320 aaggactaca tgttctggga ggtggacctg aaggagaagt tcagcgccga cctggaccag       1380 ttcccctgg gcaggaagtt cctgctgcag gccggcctgc aggccaggcc caagctgaag       1440
aggcccgcca gcagcgcccc caggaccagc accaagaaga gaaggtgaa gaggtga           1497
```

<210> SEQ ID NO 18
<211> LENGTH: 1494
<212> TYPE: DNA
<213> ORGANISM: Artificial sequence
<220> FEATURE:
<223> OTHER INFORMATION: Truncated HPV52 L1 gene

<400> SEQUENCE: 18

```
atggaggcca ccgtgtacct gccccccgtg cccgtgagca aggtggtgag caccgacgag        60
```

| | |
|---|---|
| tacgtgagca ggaccagcat ctactactac gccggcagca gcaggctgct gaccgtgggc | 120 |
| caccccctact tcagcatcaa gaacaccagc agcggcaacg caagaaggt gctggtgccc | 180 |
| aaggtgagcg gcctgcagta cagggtgttc aggatcaagc tgcccgaccc caacaagttc | 240 |
| ggcttccccg acaccagctt ctacaacccc gagacccaga ggctggtgtg gcctgcacc | 300 |
| ggcctggaga tcggcagggg ccagcccctg gcgtgggca tcagcggcca ccccctgctg | 360 |
| aacaagttcg acgacaccga gaccagcaac aagtacgccg gcaagcccgg catcgacaac | 420 |
| agggagtgcc tgagcatgga ctacaagcag acccagctgt gcatcctggg ctgcaagccc | 480 |
| cccatcggcg agcactgggg caagggcacc ccctgcaaca caacagcgg caaccccggc | 540 |
| gactgccccc ccctgcagct gatcaacagc gtgatccagg acggcgacat ggtggacacc | 600 |
| ggcttcggct gcatggactt caacaccctg caggccagca gagcgacgt gcccatcgac | 660 |
| atctgcagca gcgtgtgcaa gtaccccgac tacctgcaga tggccagcga gccctacggc | 720 |
| gacagcctgt tcttcttcct gaggagggag cagatgttcg tgaggcactt cttcaacagg | 780 |
| gccggcaccc tgggcgaccc cgtgcccggc gacctgtaca tccagggcag caacagcggc | 840 |
| aacaccgcca ccgtgcagag cagcgccttc ttccccaccc ccagcggcag catggtgacc | 900 |
| agcgagagcc agctgttcaa caagcccac tggctgcaga gggcccaggg ccacaacaac | 960 |
| ggcatctgct ggggcaacca gctgttcgtg accgtggtgg acaccaccag gagcaccaac | 1020 |
| atgaccctgt gcgccgaggt gaagaaggag agcacctaca gaacgagaa cttcaaggag | 1080 |
| tacctgaggc acggcgagga gttcgacctg cagttcatct tccagctgtg caagatcacc | 1140 |
| ctgaccgccg acgtgatgac ctacatccac aagatggacg ccaccatcct ggaggactgg | 1200 |
| cagttcggcc tgacccccc cccagcgcc agcctggagg acctacag gttcgtgacc | 1260 |
| agcaccgcca tcacctgcca gaagaacacc cccccaagg gcaaggagga cccctgaag | 1320 |
| gactacatgt tctgggaggt ggacctgaag gagaagttca gcgccgacct ggaccagttc | 1380 |
| cccctgggca ggaagttcct gctgcaggcc ggcctgcagg ccaggcccaa gctgaagagg | 1440 |
| cccgccagca gcgcccccag gaccagcacc aagaagaaga aggtgaagag gtga | 1494 |

<210> SEQ ID NO 19
<211> LENGTH: 1491
<212> TYPE: DNA
<213> ORGANISM: Artificial sequence
<220> FEATURE:
<223> OTHER INFORMATION: Truncated HPV52 L1 gene

<400> SEQUENCE: 19

| | |
|---|---|
| atggccaccg tgtacctgcc ccccgtgccc gtgagcaagg tggtgagcac cgacgagtac | 60 |
| gtgagcagga ccagcatcta ctactacgcc ggcagcagca ggctgctgac cgtgggccac | 120 |
| ccctacttca gcatcaagaa caccagcagc ggcaacggca agaaggtgct ggtgcccaag | 180 |
| gtgagcggcc tgcagtacag ggtgttcagg atcaagctgc cgaccccaa caagttcggc | 240 |
| ttccccgaca ccagcttcta caaccccgag cccagaggc tggtgtgggc ctgcaccggc | 300 |
| ctggagatcg gcaggggcca gcccctgggc gtgggcatca gcggccaccc cctgctgaac | 360 |
| aagttcgacg acaccgagac cagcaacaag tacgccggca agcccggcat cgacaacagg | 420 |
| gagtgcctga gcatggacta caagcagacc cagctgtgca tcctgggctg caagccccc | 480 |
| atcggcgagc actggggcaa gggcacccc tgcaacaaca cagcggcaa ccccggcgac | 540 |
| tgccccccc tgcagctgat caacagcgtg atccaggacg gcgacatggt ggacaccggc | 600 |
| ttcggctgca tggacttcaa caccctgcag gccagcaaga gcgacgtgcc catcgacatc | 660 |

```
tgcagcagcg tgtgcaagta ccccgactac ctgcagatgg ccagcgagcc ctacggcgac      720
agcctgttct tcttcctgag gagggagcag atgttcgtga ggcacttctt caacagggcc      780
ggcaccctgg gcgaccccgt gcccggcgac ctgtacatcc agggcagcaa cagcggcaac      840
accgccaccg tgcagagcag cgccttcttc cccaccccca gcggcagcat ggtgaccagc      900
gagagccagc tgttcaacaa gccctactgg ctgcagaggg cccagggcca caacaacggc      960
atctgctggg gcaaccagct gttcgtgacc gtggtggaca ccaccaggag caccaacatg     1020
accctgtgcg ccgaggtgaa gaaggagagc acctacaaga cgagaacttt caaggagtac     1080
ctgaggcacg gcgaggagtt cgacctgcag ttcatcttcc agctgtgcaa gatcaccctg     1140
accgccgacg tgatgaccta catccacaag atggacgcca ccatcctgga ggactggcag     1200
ttcggcctga cccccccccc cagcgccagc ctggaggaca cctacaggtt cgtgaccagc     1260
accgccatca cctgccagaa gaacaccccc ccaagggca aggaggaccc cctgaaggac     1320
tacatgttct gggaggtgga cctgaaggag aagttcagcg ccgacctgga ccagttcccc     1380
ctgggcagga agttcctgct gcaggccggc ctgcaggcca ggcccaagct gaagaggccc     1440
gccagcagcg cccccaggac cagcaccaag aagaagaagg tgaagaggtg a              1491
```

<210> SEQ ID NO 20
<211> LENGTH: 1488
<212> TYPE: DNA
<213> ORGANISM: Artificial sequence
<220> FEATURE:
<223> OTHER INFORMATION: Truncated HPV52 L1 gene

<400> SEQUENCE: 20

```
atgaccgtgt acctgccccc cgtgcccgtg agcaaggtgg tgagcaccga cgagtacgtg       60
agcaggacca gcatctacta ctacgccggc agcagcaggc tgctgaccgt gggccacccc      120
tacttcagca tcaagaacac cagcagcggc aacggcaaga aggtgctggt gcccaaggtg      180
agcggcctgc agtacagggt gttcaggatc aagctgcccg accccaacaa gttcggcttc      240
cccgacacca gcttctacaa ccccgagacc cagaggctgg tgtgggcctg caccggcctg      300
gagatcggca ggggccagcc cctgggcgtg ggcatcagcg gccaccccct gctgaacaag      360
ttcgacgaca ccgagaccag caacaagtac gccggcaagc ccggcatcga caacagggag      420
tgcctgagca tggactacaa gcagacccag ctgtgcatcc tgggctgcaa gccccccatc      480
ggcgagcact ggggcaaggg caccccctgc aacaacaaca gcggcaaccc cggcgactgc      540 cccccctgc agctgatcaa cagcgtgatc caggacggca catggtgga caccggcttc      600 ggctgcatgg acttcaacac cctgcaggcc agcaagagcg acgtgcccat cgacatctgc      660
agcagcgtgt gcaagtaccc cgactacctg cagatggcca gcgagcccta cggcgacagc      720
ctgttcttct tcctgaggag ggagcagatg ttcgtgaggc acttcttcaa cagggccggc      780
accctgggcg accccgtgcc cggcgacctg tacatccagg gcagcaacag cggcaacacc      840
gccaccgtgc agagcagcgc cttcttcccc acccccagcg gcagcatggt gaccagcgag      900
agccagctgt tcaacaagcc ctactggctg cagagggccc agggccacaa caacggcatc      960 tgctgggca accagctgtt cgtgaccgtg gtggacacca ccaggagcac caacatgacc     1020
ctgtgcgccg aggtgaagaa ggagagcacc tacaagaacg agaacttcaa ggagtacctg     1080
aggcacggcg aggagttcga cctgcagttc atcttccagc tgtgcaagat cacccctgacc     1140 gccgacgtga tgacctacat ccacaagatg gacgccacca tcctggagga ctggcagttc     1200
```

```
ggcctgaccc cccccccag cgccagcctg gaggacacct acaggttcgt gaccagcacc    1260
gccatcacct gccagaagaa caccccccc aagggcaagg aggacccct gaaggactac     1320 atgttctggg aggtggacct gaaggagaag ttcagcgccg acctggacca gttcccctg    1380 ggcaggaagt tcctgctgca ggccggcctg caggccaggc ccaagctgaa gaggcccgcc   1440
agcagcgccc ccaggaccag caccaagaag aagaaggtga agaggtga                1488
```

<210> SEQ ID NO 21
<211> LENGTH: 1485
<212> TYPE: DNA
<213> ORGANISM: Artificial sequence
<220> FEATURE:
<223> OTHER INFORMATION: Truncated HPV52 L1 gene

<400> SEQUENCE: 21

```
atggtgtacc tgccccccgt gccgtgagc aaggtggtga gcaccgacga gtacgtgagc     60
aggaccagca tctactacta cgccggcagc agcaggctgc tgaccgtggg ccaccctac    120 ttcagcatca agaacaccag cagcggcaac ggcaagaagg tgctggtgcc aaggtgagc    180 ggcctgcagt acagggtgtt caggatcaag ctgcccgacc caacaagtt cggcttcccc    240 gacaccagct tctacaaccc cgagaccag aggctggtgt gggcctgcac cggcctggag    300
atcggcaggg ccagccct gggcgtgggc atcagcggcc accccctgct gaacaagttc     360
gacgacaccg agaccagcaa caagtacgcc ggcaagcccg catcgacaa cagggagtgc    420 ctgagcatgg actacaagca gacccagctg tgcatcctgg gctgcaagcc cccatcggc     480 gagcactggg gcaagggcac ccctgcaac aacaacagcg gcaaccccgg cgactgcccc    540
cccctgcagc tgatcaacag cgtgatccag gacggcgaca tggtggacac cggcttcggc    600
tgcatggact tcaacaccct gcaggccagc aagagcgacg tgcccatcga catctgcagc    660
agcgtgtgca gtaccccga ctacctgcag atggccagcg agccctacgg cgacagcctg    720
ttcttcttcc tgaggaggga gcagatgttc gtgaggcact tcttcaacag ggccggcacc    780
ctgggcgacc ccgtgcccgg cgacctgtac atccagggca gcaacagcgg caacaccgcc    840
accgtgcaga gcagcgcctt cttccccacc cccagcggca gcatggtgac cagcgagagc    900
cagctgttca acaagcccta ctggctgcag agggcccagg ccacaacaa cggcatctgc    960 tggggcaacc agctgttcgt gaccgtggtg gacaccacca ggagcaccaa catgaccctg   1020
tgcgccgagg tgaagaagga gagcacctac aagaacgaga acttcaagga gtacctgagg   1080
cacggcgagg agttcgacct gcagttcatc ttccagctgt gcaagatcac cctgaccgcc   1140
gacgtgatga cctacatcca agatggacg ccaccatcc tggaggactg cagttcggc     1200 ctgaccccc ccccagcgc cagcctggag gacacctaca ggttcgtgac cagcaccgcc    1260
atcacctgcc agaagaacac ccccccaag ggcaaggagg accccctgaa ggactacatg    1320
ttctgggagg tggacctgaa ggagaagttc agcgccgacc tggaccagtt ccccctgggc    1380
aggaagttcc tgctgcaggc cggcctgcag gccaggccca agctgaagag gcccgccagc    1440
agcgccccca ggaccagcac caagaagaag aaggtgaaga ggtga                  1485
```

<210> SEQ ID NO 22
<211> LENGTH: 1482
<212> TYPE: DNA
<213> ORGANISM: Artificial sequence
<220> FEATURE:
<223> OTHER INFORMATION: Truncated HPV52 L1 gene

<400> SEQUENCE: 22

| | |
|---|---|
| atgtacctgc cccccgtgcc cgtgagcaag gtggtgagca ccgacgagta cgtgagcagg | 60 |
| accagcatct actactacgc cggcagcagc aggctgctga ccgtgggcca cccctacttc | 120 |
| agcatcaaga acaccagcag cggcaacggc aagaaggtgc tggtgcccaa ggtgagcggc | 180 |
| ctgcagtaca gggtgttcag gatcaagctg cccgacccca acaagttcgg cttccccgac | 240 |
| accagcttct acaaccccga cccagagg ctggtgtggg cctgcaccgg cctggagatc | 300 |
| ggcaggggcc agcccctggg cgtgggcatc agcggccacc ccctgctgaa caagttcgac | 360 |
| gacaccgaga ccagcaacaa gtacgccggc aagcccggca tcgacaacag ggagtgcctg | 420 |
| agcatggact acaagcagac ccagctgtgc atcctgggct gcaagccccc catcggcgag | 480 |
| cactggggca agggcacccc ctgcaacaac aacagcggca accccggcga ctgccccccc | 540 |
| ctgcagctga tcaacagcgt gatccaggac ggcgacatgg tggacaccgg cttcggctgc | 600 |
| atggacttca cacccctgca ggccagcaag agcgacgtgc ccatcgacat ctgcagcagc | 660 |
| gtgtgcaagt accccgacta cctgcagatg gccagcgagc cctacggcga cagcctgttc | 720 |
| ttcttcctga ggagggagca gatgttcgtg aggcacttct tcaacagggc cggcacccctg | 780 |
| ggcgaccccg tgcccggcga cctgtacatc cagggcagca cagcggcaa caccgccacc | 840 |
| gtgcagagca gcgccttctt ccccacccc agcggcagca tggtgaccag cgagagccag | 900 |
| ctgttcaaca gccctactg gctgcagagg gcccagggcc acaacaacgg catctgctgg | 960 |
| ggcaaccagc tgttcgtgac cgtggtggac accaccagga gcaccaacat gaccctgtgc | 1020 |
| gccgaggtga agaaggagag cacctacaag aacgagaact tcaaggagta cctgaggcac | 1080 |
| ggcgaggagt tcgacctgca gttcatcttc cagctgtgca gatcaccct gaccgccgac | 1140 |
| gtgatgacct acatccacaa gatggacgcc accatcctgg aggactgca gttcggcctg | 1200 |
| acccccccc ccagcgccag cctggaggac acctacaggt tcgtgaccag caccgccatc | 1260 |
| acctgccaga gaacaccccc ccccaagggc aaggaggacc ccctgaagga ctacatgttc | 1320 |
| tgggaggtgg acctgaagga agagttcagc gccgacctgg accagttccc cctgggcagg | 1380 |
| aagttcctgc tgcaggccgg cctgcaggcc aggcccaagc tgaagaggcc cgccagcagc | 1440 |
| gcccccagga ccagcaccaa gaagaagaag gtgaagaggt ga | 1482 |

<210> SEQ ID NO 23
<211> LENGTH: 1479
<212> TYPE: DNA
<213> ORGANISM: Artificial sequence
<220> FEATURE:
<223> OTHER INFORMATION: Truncated HPV52 L1 gene

<400> SEQUENCE: 23

| | |
|---|---|
| atgctgcccc ccgtgcccgt gagcaaggtg gtgagcaccg acgagtacgt gagcaggacc | 60 |
| agcatctact actacgccgg cagcagcagg ctgctgaccg tgggccaccc ctacttcagc | 120 |
| atcaagaaca ccagcagcgg caacggcaag aaggtgctgg tgcccaaggt gagcggcctg | 180 |
| cagtacaggg tgttcaggat caagctgccc gaccccaaca gttcggctt ccccgacacc | 240 |
| agcttctaca accccgagac cagaggctg gtgtgggcct gcaccggcct ggagatcggc | 300 |
| aggggccagc ccctgggcgt gggcatcagc ggccacccc tgctgaacaa gttcgacgac | 360 |
| accgagacca gcaacaagta cgccggcaag cccggcatcg acaacaggga gtgcctgagc | 420 |
| atggactaca gcagaccca gctgtgcatc ctgggctgca gcccccccat cggcgagcac | 480 |
| tggggcaagg gcacccctg caacaacaac agcggcaacc ccggcgactg ccccccctg | 540 |

| | |
|---|---|
| cagctgatca acagcgtgat ccaggacggc gacatggtgg acaccggctt cggctgcatg | 600 |
| gacttcaaca ccctgcaggc cagcaagagc gacgtgccca tcgacatctg cagcagcgtg | 660 |
| tgcaagtacc ccgactacct gcagatggcc agcgagccct acggcgacag cctgttcttc | 720 |
| ttcctgagga gggagcagat gttcgtgagg cacttcttca cagggccgg caccctgggc | 780 |
| gaccccgtgc ccggcgacct gtacatccag ggcagcaaca gcggcaacac cgccaccgtg | 840 |
| cagagcagcg ccttcttccc cacccccagc ggcagcatgg tgaccagcga gagccagctg | 900 |
| ttcaacaagc cctactggct gcagagggcc cagggccaca caacggcat ctgctggggc | 960 |
| aaccagctgt tcgtgaccgt ggtggacacc accaggagca ccaacatgac cctgtgcgcc | 1020 |
| gaggtgaaga aggagagcac ctacaagaac gagaacttca aggagtacct gaggcacggc | 1080 |
| gaggagttcg acctgcagtt catcttccag ctgtgcaaga tcaccctgac cgccgacgtg | 1140 |
| atgacctaca tccacaagat ggacgccacc atcctggagg actggcagtt cggcctgacc | 1200 |
| ccccccccca gcgccagcct ggaggacacc tacaggttcg tgaccagcac cgccatcacc | 1260 |
| tgccagaaga acaccccccc caagggcaag gaggacccc tgaaggacta catgttctgg | 1320 |
| gaggtggacc tgaaggagaa gttcagcgcc gacctggacc agttcccct gggcaggaag | 1380 |
| ttcctgctgc aggccggcct gcaggccagg cccaagctga gaggcccgc cagcagcgcc | 1440 |
| cccaggacca gcaccaagaa gaagaaggtg aagaggtga | 1479 |

<210> SEQ ID NO 24
<211> LENGTH: 1476
<212> TYPE: DNA
<213> ORGANISM: Artificial sequence
<220> FEATURE:
<223> OTHER INFORMATION: Truncated HPV52 L1 gene

<400> SEQUENCE: 24

| | |
|---|---|
| atgccccccg tgcccgtgag caaggtggtg agcaccgacg agtacgtgag caggaccagc | 60 |
| atctactact acgccggcag cagcaggctg ctgaccgtgg gccaccccta cttcagcatc | 120 |
| aagaacacca gcagcggcaa cggcaagaag gtgctggtgc caaggtgag cggcctgcag | 180 |
| tacagggtgt tcaggatcaa gctgcccgac cccaacaagt tcggcttccc cgacaccagc | 240 |
| ttctacaacc ccgagaccca gaggctggtg tgggcctgca ccggcctgga gatcggcagg | 300 |
| ggccagcccc tgggcgtggg catcagcggc caccccctgc tgaacaagtt cgacgacacc | 360 |
| gagaccagca acaagtacgc cggcaagccc ggcatcgaca cagggagtg cctgagcatg | 420 |
| gactacaagc agacccagct gtgcatcctg ggctgcaagc cccccatcgg cgagcactgg | 480 |
| ggcaagggca cccctgcaa caacaacagc ggcaaccccg gcgactgccc cccctgcag | 540 |
| ctgatcaaca gcgtgatcca ggacggcgac atggtggaca ccggcttcgg ctgcatggac | 600 |
| ttcaacaccc tgcaggccag caagagcgac gtgcccatcg acatctgcag cagcgtgtgc | 660 |
| aagtacccg actacctgca gatggccagc gagccctacg gcgacagcct gttcttcttc | 720 |
| ctgaggaggg agcagatgtt cgtgaggcac ttcttcaaca gggccggcac cctgggcgac | 780 |
| cccgtgcccg gcgacctgta catccagggc agcaacagcg gcaacaccgc caccgtgcag | 840 |
| agcagcgcct tcttccccac ccccagcggc agcatggtga ccagcgagag ccagctgttc | 900 |
| aacaagccct actggctgca gagggcccag gccacaaca cggcatctg ctggggcaac | 960 |
| cagctgttcg tgaccgtggt ggacaccacc aggagcacca acatgaccct gtgcgccgag | 1020 |
| gtgaagaagg agagcaccta caagaacgag aacttcaagg agtacctgag gcacggcgag | 1080 |
| gagttcgacc tgcagttcat cttccagctg tgcaagatca ccctgaccgc cgacgtgatg | 1140 |

```
acctacatcc acaagatgga cgccaccatc ctggaggact ggcagttcgg cctgacccc      1200 cccccccagcg ccagcctgga ggacacctac aggttcgtga ccagcaccgc catcacctgc     1260
cagaagaaca cccccccaa gggcaaggag accccctga aggactacat gttctgggag        1320
gtggacctga aggagaagtt cagcgccgac ctggaccagt tccccctggg caggaagttc       1380
ctgctgcagg ccggcctgca ggccaggccc aagctgaaga ggcccgccag cagcgccccc      1440
aggaccagca ccaagaagaa gaaggtgaag aggtga                                1476
```

<210> SEQ ID NO 25
<211> LENGTH: 1473
<212> TYPE: DNA
<213> ORGANISM: Artificial sequence
<220> FEATURE:
<223> OTHER INFORMATION: Truncated HPV52 L1 gene

<400> SEQUENCE: 25

```
atgcccgtgc ccgtgagcaa ggtggtgagc accgacgagt acgtgagcag gaccagcatc       60
tactactacg ccggcagcag caggctgctg accgtgggcc acccctactt cagcatcaag      120
aacaccagca gcggcaacgg caagaaggtg ctggtgccca aggtgagcgg cctgcagtac      180
agggtgttca ggatcaagct gcccgacccc aacaagttcg gcttccccga caccagcttc     240
tacaaccccg agacccagag gctggtgtgg ggcctgcaccg gcctggagat cggcaggggc     300 cagccctgg gcgtgggcat cagcggccac ccctgctga acaagttcga cgacaccgag        360
accagcaaca gtacgccgg caagcccggc atcgacaaca gggagtgcct gagcatggac       420
tacaagcaga cccagctgtg catcctgggc tgcaagcccc catcggcga gcactggggc       480 aagggcaccc cctgcaacaa caacagcggc aaccccggcg actgccccc cctgcagctg       540 atcaacagcg tgatccagga cggcgacatg gtggacaccg gcttcggctg catggactc      600 aacaccctgc aggccagcaa gagcgacgtg cccatcgaca tctgcagcag cgtgtgcaag     660 tacccgact acctgcagat ggccagcgag ccctacggcg acagcctgtt cttcttcctg      720
aggagggagc agatgttcgt gaggcacttc ttcaacaggg ccggcacccg ggcgaccc       780 gtgcccggcg acctgtacat ccagggcagc aacagcggca caccgccac cgtgcagagc     840 agcgccttct ccccaccccc cagcggcagc atggtgacca gcgagagcca gctgttcaac     900
aagccctact ggctgcagag ggcccagggc cacaacaacg gcatctgctg gggcaaccag     960
ctgttcgtga ccgtggtgga caccaccagg agcaccaaca tgaccctgtg cgccgaggtg    1020
aagaaggaga gcacctacaa gaacgagaac ttcaaggagt acctgaggca cggcgaggag    1080
ttcgacctgc agttcatctt ccagctgtgc aagatcaccc tgaccgccga cgtgatgacc    1140
tacatccaca gatggacgc caccatcctg gaggactggc agttcggcct gacccccc       1200 cccagcgcca gcctggagga cacctacagg ttcgtgacca gcaccgccat cacctgccag    1260
aagaacaccc cccccaaggg caaggaggac cccctgaagg actacatgtt ctgggaggtg    1320
gacctgaagg agaagttcag cgccgacctg gaccagttcc ccctgggcag gaagttcctg    1380
ctgcaggccg gcctgcaggc caggccccag ctgaagaggc cgccagcag cgcccccagg    1440 accagcacca gaagaagaa ggtgaagagg tga                                  1473
```

<210> SEQ ID NO 26
<211> LENGTH: 1467
<212> TYPE: DNA
<213> ORGANISM: Artificial sequence
<220> FEATURE:

<223> OTHER INFORMATION: Truncated HPV52 L1 gene

<400> SEQUENCE: 26

```
atgcccgtga gcaaggtggt gagcaccgac gagtacgtga gcaggaccag catctactac      60
tacgccggca gcagcaggct gctgaccgtg ggccacccct acttcagcat caagaacacc     120
agcagcggca acggcaagaa ggtgctggtg cccaaggtga gcggcctgca gtacagggtg     180
ttcaggatca agctgcccga ccccaacaag ttcggcttcc ccgacaccag cttctacaac     240
cccgagaccc agaggctggt gtgggcctgc accggcctgg agatcggcag gggccagccc     300
ctgggcgtgg gcatcagcgg ccaccccctg ctgaacaagt cgacgacac cgagaccagc      360
aacaagtacg ccggcaagcc cggcatcgac aacagggagt gcctgagcat ggactacaag     420
cagacccagc tgtgcatcct gggctgcaag ccccccatcg cgagcactg gggcaagggc      480
accccctgca caacaacag cggcaacccc ggcgactgcc ccccctgca gctgatcaac       540
agcgtgatcc aggacggcga catggtggac accggcttcg gctgcatgga cttcaacacc     600
ctgcaggcca gcagagcga cgtgcccatc gacatctgca gcagcgtgtg caagtacccc      660
gactacctgc agatggccag cgagccctac ggcgacagcc tgttcttctt cctgaggagg     720
gagcagatgt tcgtgaggca cttcttcaac agggccggca ccctgggcga ccccgtgccc     780
ggcgacctgt acatccaggg cagcaacagc ggcaacaccg ccaccgtgca gagcagcgcc     840
ttcttcccca cccccagcgg cagcatggtg accagcgaga ccagctgtt caacaagccc       900
tactggctgc agagggccca gggccacaac aacggcatct gctgggcaa ccagctgttc       960
gtgaccgtgg tggacaccac caggagcacc aacatgaccc tgtgcgccga ggtgaagaag    1020
gagagcacct acaagaacga gaacttcaag gagtacctga ggcacggcga ggagttcgac    1080
ctgcagttca tcttccagct gtgcaagatc accctgaccg ccgacgtgat gacctacatc    1140
cacaagatgg acgccaccat cctggaggac tggcagttcg gcctgacccc ccccccagc     1200
gccagcctgg aggacaccta caggttcgtg accagcaccg ccatcacctg ccagaagaac    1260
acccccccca gggcaagga ggacccctg aaggactaca tgttctggga ggtggacctg      1320
aaggagaagt tcagcgccga cctggaccag ttcccctgg caggaagtt cctgctgcag       1380
gccggcctgc aggccaggcc caagctgaag aggcccgcca gcagcgcccc caggaccagc    1440
accaagaaga agaaggtgaa gaggtga                                        1467
```

<210> SEQ ID NO 27
<211> LENGTH: 529
<212> TYPE: PRT
<213> ORGANISM: Human papillomavirus type 52

<400> SEQUENCE: 27

```
Met Val Gln Ile Leu Phe Tyr Ile Leu Val Ile Phe Tyr Tyr Val Ala
1               5                   10                  15

Gly Val Asn Val Phe His Ile Phe Leu Gln Met Ser Val Trp Arg Pro
            20                  25                  30

Ser Glu Ala Thr Val Tyr Leu Pro Pro Val Pro Val Ser Lys Val Val
        35                  40                  45

Ser Thr Asp Glu Tyr Val Ser Arg Thr Ser Ile Tyr Tyr Ala Gly
    50                  55                  60

Ser Ser Arg Leu Leu Thr Val Gly His Pro Tyr Phe Ser Ile Lys Asn
65                  70                  75                  80

Thr Ser Ser Gly Asn Gly Lys Lys Val Leu Val Pro Lys Val Ser Gly
                85                  90                  95
```

-continued

```
Leu Gln Tyr Arg Val Phe Arg Ile Lys Leu Pro Asp Pro Asn Lys Phe
                100                 105                 110

Gly Phe Pro Asp Thr Ser Phe Tyr Asn Pro Glu Thr Gln Arg Leu Val
            115                 120                 125

Trp Ala Cys Thr Gly Leu Glu Ile Gly Arg Gly Gln Pro Leu Gly Val
        130                 135                 140

Gly Ile Ser Gly His Pro Leu Leu Asn Lys Phe Asp Asp Thr Glu Thr
145                 150                 155                 160

Ser Asn Lys Tyr Ala Gly Lys Pro Gly Ile Asp Asn Arg Glu Cys Leu
                165                 170                 175

Ser Met Asp Tyr Lys Gln Thr Gln Leu Cys Ile Leu Gly Cys Lys Pro
            180                 185                 190

Pro Ile Gly Glu His Trp Gly Lys Gly Thr Pro Cys Asn Asn Asn Ser
        195                 200                 205

Gly Asn Pro Gly Asp Cys Pro Pro Leu Gln Leu Ile Asn Ser Val Ile
        210                 215                 220

Gln Asp Gly Asp Met Val Asp Thr Gly Phe Gly Cys Met Asp Phe Asn
225                 230                 235                 240

Thr Ser Gln Ala Ser Lys Ser Asp Val Pro Ile Asp Ile Cys Ser Ser
                245                 250                 255

Val Cys Lys Tyr Pro Asp Tyr Leu Gln Met Ala Ser Glu Pro Tyr Gly
            260                 265                 270

Asp Ser Leu Phe Phe Phe Leu Arg Arg Glu Gln Met Phe Val Arg His
        275                 280                 285

Phe Phe Asn Arg Ala Gly Thr Leu Gly Asp Pro Val Pro Gly Asp Leu
        290                 295                 300

Tyr Ile Gln Gly Ser Asn Ser Gly Asn Thr Ala Thr Val Gln Ser Ser
305                 310                 315                 320

Ala Phe Phe Pro Thr Pro Ser Gly Ser Met Val Thr Ser Glu Ser Gln
                325                 330                 335

Leu Phe Asn Lys Pro Tyr Trp Leu Gln Arg Ala Gln Gly His Asn Asn
            340                 345                 350

Gly Ile Cys Trp Gly Asn Gln Leu Phe Val Thr Val Val Asp Thr Thr
        355                 360                 365

Arg Ser Thr Asn Met Thr Leu Cys Ala Glu Val Lys Lys Glu Ser Thr
        370                 375                 380

Tyr Lys Asn Glu Asn Phe Lys Glu Tyr Leu Arg His Gly Glu Glu Phe
385                 390                 395                 400

Asp Leu Gln Phe Ile Phe Gln Leu Cys Lys Ile Thr Leu Thr Ala Asp
                405                 410                 415

Val Met Thr Tyr Ile His Lys Met Asp Ala Thr Ile Leu Glu Asp Trp
            420                 425                 430

Gln Phe Gly Leu Thr Pro Pro Ser Ala Ser Leu Glu Asp Thr Tyr
        435                 440                 445

Arg Phe Val Thr Ser Thr Ala Ile Thr Cys Gln Lys Asn Thr Pro Pro
        450                 455                 460

Lys Gly Lys Glu Asp Pro Leu Lys Asp Tyr Met Phe Trp Glu Val Asp
465                 470                 475                 480

Leu Lys Glu Lys Phe Ser Ala Asp Leu Asp Gln Phe Pro Leu Gly Arg
                485                 490                 495

Lys Phe Leu Leu Gln Ala Gly Leu Gln Ala Arg Pro Lys Leu Lys Arg
            500                 505                 510
```

```
Pro Ala Ser Ser Ala Pro Arg Thr Ser Thr Lys Lys Lys Val Lys
            515                 520                 525

Arg

<210> SEQ ID NO 28
<211> LENGTH: 529
<212> TYPE: PRT
<213> ORGANISM: Human papillomavirus type 52

<400> SEQUENCE: 28

Met Val Gln Ile Leu Phe Tyr Ile Leu Val Ile Phe Tyr Tyr Val Ala
1               5                   10                  15

Gly Val Asn Val Phe His Ile Phe Leu Gln Met Ser Val Trp Arg Pro
            20                  25                  30

Ser Glu Ala Thr Val Tyr Leu Pro Pro Val Pro Val Ser Lys Val Val
        35                  40                  45

Ser Thr Asp Glu Tyr Val Ser Arg Thr Ser Ile Tyr Tyr Ala Gly
    50                  55                  60

Ser Ser Arg Leu Leu Thr Val Gly His Pro Tyr Phe Ser Ile Lys Asn
65                  70                  75                  80

Thr Ser Ser Gly Asn Gly Lys Lys Val Leu Val Pro Lys Val Ser Gly
                85                  90                  95

Leu Gln Tyr Arg Val Phe Arg Ile Lys Leu Pro Asp Pro Asn Lys Phe
            100                 105                 110

Gly Phe Pro Asp Thr Ser Phe Tyr Asn Pro Glu Thr Gln Arg Leu Val
        115                 120                 125

Trp Ala Cys Thr Gly Leu Glu Ile Gly Arg Gly Gln Pro Leu Gly Val
    130                 135                 140

Gly Ile Ser Gly His Pro Leu Leu Asn Lys Phe Asp Asp Thr Glu Thr
145                 150                 155                 160

Ser Asn Lys Tyr Ala Gly Lys Pro Gly Ile Asp Asn Arg Glu Cys Leu
                165                 170                 175

Ser Met Asp Tyr Lys Gln Thr Gln Leu Cys Ile Leu Gly Cys Lys Pro
            180                 185                 190

Pro Ile Gly Glu His Trp Gly Lys Gly Thr Pro Cys Asn Asn Asn Ser
        195                 200                 205

Gly Asn Pro Gly Asp Cys Pro Pro Leu Gln Leu Ile Asn Ser Val Ile
    210                 215                 220

Gln Asp Gly Asp Met Val Asp Thr Gly Phe Gly Cys Met Asp Phe Asn
225                 230                 235                 240

Thr Leu Gln Ala Ser Lys Ser Asp Val Pro Ile Asp Ile Cys Ser Ser
                245                 250                 255

Val Cys Lys Tyr Pro Asp Tyr Leu Gln Met Ala Ser Glu Pro Tyr Gly
            260                 265                 270

Asp Ser Leu Phe Phe Phe Leu Arg Arg Glu Gln Met Phe Val Arg His
        275                 280                 285

Phe Phe Asn Arg Ala Gly Thr Leu Gly Asp Pro Val Pro Gly Asp Leu
    290                 295                 300

Tyr Ile Gln Gly Ser Asn Ser Gly Asn Thr Ala Thr Val Gln Ser Ser
305                 310                 315                 320

Ala Phe Phe Pro Thr Pro Ser Gly Ser Met Val Thr Ser Glu Ser Gln
                325                 330                 335

Leu Phe Asn Lys Pro Tyr Trp Leu Gln Arg Ala Gln Gly His Asn Asn
            340                 345                 350
```

```
Gly Ile Cys Trp Gly Asn Gln Leu Phe Val Thr Val Asp Thr Thr
            355                 360                 365

Arg Ser Thr Asn Met Thr Leu Cys Ala Glu Val Lys Lys Ser Thr
        370                 375                 380

Tyr Lys Asn Glu Asn Phe Lys Glu Tyr Leu Arg His Gly Glu Phe
385                 390                 395                 400

Asp Leu Gln Phe Ile Phe Gln Leu Cys Lys Ile Thr Leu Thr Ala Asp
                405                 410                 415

Val Met Thr Tyr Ile His Lys Met Asp Ala Thr Ile Leu Glu Asp Trp
            420                 425                 430

Gln Phe Gly Leu Thr Pro Pro Ser Ala Ser Leu Gly Asp Thr Tyr
            435                 440                 445

Arg Phe Val Thr Ser Thr Ala Ile Thr Cys Gln Lys Asn Thr Pro Pro
    450                 455                 460

Lys Gly Lys Glu Asp Pro Leu Lys Asp Tyr Met Phe Trp Glu Val Asp
465                 470                 475                 480

Leu Lys Glu Lys Phe Ser Ala Asp Leu Asp Gln Phe Pro Leu Gly Arg
                485                 490                 495

Lys Phe Leu Leu Gln Ala Gly Leu Gln Ala Arg Pro Lys Leu Lys Arg
                500                 505                 510

Pro Ala Ser Ser Ala Pro Arg Thr Ser Thr Lys Lys Lys Val Lys
            515                 520                 525

Arg

<210> SEQ ID NO 29
<211> LENGTH: 529
<212> TYPE: PRT
<213> ORGANISM: Human papillomavirus type 52

<400> SEQUENCE: 29

Met Val Gln Ile Leu Phe Tyr Ile Leu Val Ile Phe Tyr Val Ala
1                   5                   10                  15

Gly Val Asn Val Phe His Ile Phe Leu Gln Met Ser Val Trp Arg Pro
                20                  25                  30

Ser Glu Ala Thr Val Tyr Leu Pro Pro Val Pro Val Ser Lys Val Val
            35                  40                  45

Ser Thr Asp Glu Tyr Val Ser Arg Thr Ser Ile Tyr Tyr Tyr Ala Gly
    50                  55                  60

Ser Ser Arg Leu Leu Thr Val Gly His Pro Tyr Phe Ser Ile Lys Asn
65                  70                  75                  80

Thr Ser Ser Gly Asn Gly Lys Lys Val Leu Val Pro Lys Val Ser Gly
                85                  90                  95

Leu Gln Tyr Arg Val Phe Arg Ile Lys Leu Pro Asp Pro Asn Lys Phe
            100                 105                 110

Gly Phe Pro Asp Thr Ser Phe Tyr Asn Pro Glu Thr Gln Arg Leu Val
        115                 120                 125

Trp Ala Cys Thr Gly Leu Glu Ile Gly Arg Gly Gln Pro Leu Gly Val
130                 135                 140

Gly Ile Ser Gly His Pro Leu Leu Asn Lys Phe Asp Asp Thr Glu Thr
145                 150                 155                 160

Ser Asn Lys Tyr Ala Gly Lys Pro Gly Ile Asp Asn Arg Glu Cys Leu
                165                 170                 175

Ser Met Asp Tyr Lys Gln Thr Gln Leu Cys Ile Leu Gly Cys Lys Pro
            180                 185                 190
```

```
Pro Ile Gly Glu His Trp Gly Lys Gly Thr Pro Cys Asn Asn Ser
            195                 200                 205
Gly Asn Pro Gly Asp Cys Pro Pro Leu Gln Leu Ile Asn Ser Val Ile
    210                 215                 220
Gln Asp Gly Asp Met Val Asp Thr Gly Phe Gly Cys Met Asp Phe Asn
225                 230                 235                 240
Thr Leu Gln Ala Ser Lys Ser Asp Val Pro Ile Asp Ile Cys Ser Ser
                245                 250                 255
Val Cys Lys Tyr Pro Asp Tyr Leu Gln Met Ala Ser Glu Pro Tyr Gly
            260                 265                 270
Asp Ser Leu Phe Phe Phe Leu Arg Arg Glu Gln Met Phe Val Arg His
    275                 280                 285
Phe Phe Asn Arg Ala Gly Thr Leu Gly Asp Pro Val Pro Gly Asp Leu
290                 295                 300
Tyr Ile Gln Gly Ser Asn Ser Gly Asn Thr Ala Thr Val Gln Ser Ser
305                 310                 315                 320
Ala Phe Phe Pro Thr Pro Ser Gly Ser Met Val Thr Ser Glu Ser Gln
                325                 330                 335
Leu Phe Asn Lys Pro Tyr Trp Leu Gln Arg Ala Gln Gly His Asn Asn
            340                 345                 350
Gly Ile Cys Trp Gly Asn Gln Leu Phe Val Thr Val Val Asp Thr Thr
    355                 360                 365
Arg Ser Thr Asn Met Thr Leu Cys Ala Glu Val Lys Lys Glu Ser Thr
370                 375                 380
Tyr Lys Asn Glu Asn Phe Lys Glu Tyr Leu Arg His Gly Glu Glu Phe
385                 390                 395                 400
Asp Leu Gln Phe Ile Phe Gln Leu Cys Lys Ile Thr Leu Ala Ala Asp
                405                 410                 415
Val Met Thr Tyr Ile His Lys Met Asp Ala Thr Ile Leu Glu Asp Trp
            420                 425                 430
Gln Phe Gly Leu Thr Pro Pro Ser Ala Ser Leu Glu Asp Thr Tyr
    435                 440                 445
Arg Phe Val Thr Ser Thr Ala Ile Thr Cys Gln Lys Asn Thr Pro Pro
450                 455                 460
Lys Gly Lys Glu Asp Pro Leu Lys Asp Tyr Met Phe Trp Glu Val Asp
465                 470                 475                 480
Leu Lys Glu Lys Phe Ser Ala Asp Leu Asp Gln Phe Pro Leu Gly Arg
                485                 490                 495
Lys Phe Leu Leu Gln Ala Gly Leu Gln Ala Arg Pro Lys Leu Lys Arg
            500                 505                 510
Pro Ala Ser Ser Ala Pro Arg Thr Ser Thr Lys Lys Lys Val Lys
            515                 520                 525
Arg

<210> SEQ ID NO 30
<211> LENGTH: 1590
<212> TYPE: DNA
<213> ORGANISM: Human papillomavirus type 52

<400> SEQUENCE: 30
atggtgcaga tcctgttcta catcctggtg atcttctact acgtggccgg cgtgaacgtg    60
ttccacatct tcctgcagat gagcgtgtgg aggcccagcg aggccaccgt gtacctgccc   120
cccgtgcccg tgagcaaggt ggtgagcacc gacgagtacg tgagcaggac cagcatctac   180
```

-continued

```
tactacgccg gcagcagcag gctgctgacc gtgggccacc cctacttcag catcaagaac    240
accagcagcg gcaacggcaa gaaggtgctg gtgcccaagg tgagcggcct gcagtacagg    300
gtgttcagga tcaagctgcc cgaccccaac aagttcggct tccccgacac cagcttctac    360
aaccccgaga cccagaggct ggtgtgggcc tgcaccggcc tggagatcgg caggggccag    420
cccctgggcg tgggcatcag cggccacccc ctgctgaaca agttcgacga caccgagacc    480
agcaacaagt acgccggcaa gcccggcatc gacaacaggg agtgcctgag catggactac    540
aagcagaccc agctgtgcat cctgggctgc aagccccca tcggcgagca ctggggcaag    600 ggcacccct gcaacaacaa cagcggcaac cccggcgact gccccccct gcagctgatc    660 aacagcgtga tccaggacgg cgacatggtg gacaccggct cggctgcat ggacttcaac    720 accctgcagg ccagcaagag cgacgtgccc atcgacatct gcagcagcgt gtgcaagtac    780
cccgactacc tgcagatggc cagcgagccc tacgcgaca gcctgttctt cttcctgagg    840
agggagcaga tgttcgtgag gcacttcttc aacagggccg gcaccctggg cgaccccgtg    900 cccgcgacc tgtacatcca gggcagcaac agcggcaaca ccgccaccgt gcagagcagc    960
gccttcttcc ccaccccag cggcagcatg gtgaccagcg agagccagct gttcaacaag   1020
ccctactggc tgcagagggc ccagggccac aacaacggca tctgctgggg caaccagctg   1080
ttcgtgaccg tggtggacac caccaggagc accaacatga ccctgtgcgc cgaggtgaag   1140
aaggagagca cctacaagaa cgagaacttc aaggagtacc tgaggcacgg cgaggagttc   1200
gacctgcagt tcatcttcca gctgtgcaag atcaccctga ccgccgacgt gatgacctac   1260
atccacaaga tggacgccac catcctggag gactggcagt tcggcctgac cccccccccc   1320
agcgccagcc tggaggacac ctacaggttc gtgaccagca ccgccatcac ctgccagaag   1380
aacacccccc ccaagggcaa ggaggacccc ctgaaggact acatgttctg ggaggtggac   1440
ctgaaggaga agttcagcgc cgacctggac cagttccccc tgggcaggaa gttcctgctg   1500
caggccggcc tgcaggccag gcccaagctg aagaggcccg ccagcagcgc ccccaggacc   1560
agcaccaaga agaagaaggt gaagaggtga                                    1590
```

```
<210> SEQ ID NO 31
<211> LENGTH: 24
<212> TYPE: DNA
<213> ORGANISM: Artificial sequence
<220> FEATURE:
<223> OTHER INFORMATION: primer

<400> SEQUENCE: 31
catatgcccg tgcccgtgag caag                                            24

<210> SEQ ID NO 32
<211> LENGTH: 25
<212> TYPE: DNA
<213> ORGANISM: Artificial sequence
<220> FEATURE:
<223> OTHER INFORMATION: primer

<400> SEQUENCE: 32
gtcgactcac ctcttcacct tcttc                                           25
```

TRUNCATED L1 PROTEIN OF HUMAN PAPILLOMAVIRUS TYPE 52

CROSS-REFERENCE TO RELATED APPLICATIONS

This is the U.S. National Stage of PCT/CN2011/076763, filed Jul. 1, 2011, which in turn claims priority to Chinese Patent Application No. 201010216189.X, filed Jul. 2, 2010, the entire contents of all applications are incorporated herein by reference in their entireties.

FIELD OF THE INVENTION

The invention relates to the field of molecular virology and immunology. In particular, the invention relates to a truncated L1 protein of Human Papillomavirus Type 52, its coding sequence and preparation method, and a virus-like particle comprising the protein, wherein the protein and the virus-like particle are useful for preventing HPV (particularly HPV52) infection, and a disease caused by HPV (particularly HPV52) infection, such as cervical cancer. The invention also relates to the use of the protein and the virus-like particle in the preparation of a pharmaceutical composition or a vaccine for preventing HPV (particularly HPV52) infection, and a disease caused by HPV (particularly HPV52) infection, such as cervical cancer.

BACKGROUND OF THE INVENTION

Human Papillomavirus (HPV), a non-enveloped, deoxyribonucleic acid (DNA) virus, belongs to the family Papillomaviridae. The viral genome is a double-stranded, closed circular DNA, which is approximately 7.2-8 kb in length and contains 8 open reading frames (ORFs). The genome can be divided into three parts in terms of function: (1) the early region (E), approximately 4.5 Kb in length, coding for 6 non-structural proteins E1, E2, E4-E7 associated with virus replication, transcription and transformation; (2) the late region (L), approximately 2.5 Kb in length, coding for the major capsid protein L1 and the minor capsid protein L2; (3) the long control region (LCR), located between the end of the L region and the initiating terminal of the E region, approximately 800-900 bp in length, and comprising regulator elements for DNA replication and expression instead of coding for proteins. HPV viral particles have a diameter of 45-55 nm, wherein the nucleocapsid, consisting of L1 and L2, exhibits icosahedral symmetry and comprises 72 capsomers.

Currently, there are over 100 different types of HPV, mainly causing papillary disease in the skin and mucosa of human. HPV types are divided into three groups depending on their relation with tumorigenesis: (1) group of low or no cancerogenic risk, containing HPV 6, 11, 39, 41, 42, and 43; (2) group of medium cancerogenic risk, containing HPV 31, 33, 35 and 51; and (3) group of high cancerogenic risk, containing HPV 16, 18, 58, 45 and 52.

HPV molecular epidemiological investigation demonstrates that infection by high-risk HPV types is an important factor responsible for the development of cervical cancer. Among all the cervical cancer specimens, HPV DNA is detected in over 80% of them. Cervical cancer is a common malignant tumor among women, the incidence of which is only next to breast cancer, and seriously threatens the health of women. There are about 490,000 newly reported cases worldwide every year, and nearly 270,000 people die of this disease annually (Boyle, P., and J. Ferlay. Ann Oncol 2005, 16:481-8). Cases in developing countries account for approximately 83% of the total cervical cancer cases. In these developing countries, the cervical cancer cases account for about 15% of female malignant tumors, in contrast to 1.5% in developed countries. Cervical cancer is most prevalent in sub-Saharan Africa, central and Southern Asia, Latin America, and Eastern Asia. Cervical cancer is also prevalent in China. The incidence of cervical cancer among married women is as high as 1026/100000 in Lueyang County of Shanxi Province.

The distribution of HPV types exhibits some characteristics of geographical distribution and populations. HPV 16 and 18 subtypes are the most common types in cervical cancer worldwide, and HPV52 subtype is the sixth most common high-risk HPV type. Among some areas of China, for example, provinces such as Guangdong province, HPV52 is a high-risk cancerogenic HPV type only next to HPV 16, 33 and 18.

Currently, the commercially available HPV vaccines are Gardasil® from Merck and Cervarix® from GSK, which comprise HPV6/11/16/18 and HPV16/18 VLP, respectively, but do not comprise HPV type 52 VLP.

Therefore, vaccines directed to HPV type 52 shall be involved in the development of vaccines for high-risk types, which cover a wider scope and are more suitable for Chinese population.

HPV L1 protein, with a molecular weight of 55-60 kDa, is the major capsid protein of the human papillomavirus and the main target protein of the HPV vaccine. HPV L1 protein expressed in many expression systems can form Virus-Like Particles (VLPs) which resemble native HPV particles morphologically, without the assistance of the L2 protein. The VLPs, consisting of 72 pentamers of the L1 proteins, exhibit icosahedral symmetry. Since the VLPs retain the native epitopes of the viral particles, they are highly immunogenic and can induce the generation of neutralization antibodies against homologous HPV (Kirnbauer, R., F. Booy, et al. 1992 Proc Natl Acad Sci USA 89(24): 12180-4). Furthermore, the VLPs are safe and have no potential cancergenic risk as they contain no viral nucleic acids. Therefore, VLP vaccines have become the primary candidate for HPV vaccines.

The key for development of HPV VLP vaccines lies in efficient production of VLP samples in large-scale. Currently, the most common expression systems used for VLP are divided into eukaryotic expression systems and prokaryotic expression systems.

The commonly used eukaryotic expression systems comprise poxvirus, insect baculovirus and yeast expression systems. HPV L1 protein expressed in eukaryotic expression systems shows little conformational difference from that of the native virus, and can self-assemble into VLPs. Thus, purified VLPs can be easily obtained after simple gradient density centrifugation. It brings a lot of convenience to the purification work. However, due to the high culture costs and low expression level of eukaryotic expression systems, it is quite difficult to product industrially on a large-scale. The HPV vaccine Gardasil®, which came into the market recently, is more expensive than others due to low expression level and high production cost of the *Saccharomyces cerevisiae* expression system employed in its manufacture, and therefore, its general application is limited.

The expression of HPV L1 protein in a prokaryotic expression system such as *E. coli* expression system has been previously reported. The expression of HPV 16 L1 protein by employing *E. coli* has been reported (Banks, L., G. Matlashewski, et al. (1987). J Gen Virol 68 (Pt 12):

3081-9). However, most HPV L1 proteins expressed in *E. coli* lose their native conformation and cannot induce protective antibodies against HPV. Alternatively, although HPV VLPs can be obtained from the proteins by steps such as purification from inclusion bodies and renaturation (Kelsall, S. R. and J. K. Kulski (1995). J Virol Methods 53(1): 75-90), it is difficult to apply this method to large-scale production, as the proteins are largely lost during the renaturation process and the yield is low. Although HPV L1 protein may be expressed in a soluble form with a correct conformation in *E. coli* and be dissolved in the supernatants of *E. coli* lysate, the expression level is low. Moreover, since there are large number and amounts of impure proteins, it is difficult to isolate the proteins of interest from them. Although it is also reported that the expression level of L1 protein can be increased in the supernatants by means of GST fusion expression and the purification of the protein of interest is facilitated (Li, M., T. P. Cripe, et al. (1997), J Virol 71(4): 2988-95), it still cannot be applied to larger-scale production because expensive enzymes are required to cleave the fusion protein.

Therefore, the obtainment of a HPV L1 protein capable of inducing the generation of protective antibodies against HPV, and a virus-like particle consisting of the same, at low cost, are still urgent in the art, in order to make the large-scale industrial production of vaccines for cervical cancer possible.

DESCRIPTION OF THE INVENTION

The invention is at least partially based on the inventors' surprised discovery: a truncated HPV52 L1 protein capable of inducing the generation of neutralization antibodies against HPV52 can be expressed in an *E. coli* expression system on a large scale, wherein the truncated HPV52 L1 protein can be produced with a high yield, and the purity of the purified protein reaches at least 50% or higher (such as 60%, 70%, 80%, 90%, 95%, 96%, 97%, 98%, and 99%). Moreover, further treatment of the purified protein results in the obtainment of VLPs capable of inducing the generation of protective antibodies against HPV52.

Therefore, in one aspect, the invention relates to a truncated HPV52 L1 protein or variants thereof, wherein said protein has 27-42 amino acids, for example, 27, 28, 29, 30, 31, 32, 33, 34, 35, 36, 37, 38, 39, 40, 41, or 42 amino acids, truncated at its N-terminal.

In one aspect, the invention relates to a truncated HPV52 L1 protein or variants thereof, wherein said protein has 27-42 amino acids, for example, 27, 28, 29, 30, 31, 32, 33, 34, 35, 36, 37, 38, 39, 40, 41, or 42 amino acids, truncated at its N-terminal, as compared with wild type HPV52 L1 protein.

In a preferred embodiment, the truncated HPV52 L1 protein has 27-42 amino acids (such as, 35-42 amino acids), for example, 27, 35, 38, 40, or 42 amino acids, truncated at its N-terminal, as compared with wild type HPV52 L1 protein. In another preferred embodiment, the truncated HPV52 L1 protein has 40 amino acids truncated at its N-terminal, as compared with wild type HPV52 L1 protein.

In another preferred embodiment, the truncated HPV52 L1 protein (cited hereafter as the truncated protein) has an amino acid sequence as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13; such as, an amino acid sequence as set forth in SEQ ID NO: 1, SEQ ID NO: 7, SEQ ID NO: 10, SEQ ID NO: 12, or SEQ ID NO: 13. In another preferred embodiment, the truncated protein has an amino acid sequence as set forth in SEQ ID NO: 12.

In another aspect, the invention relates to a polynucleotide encoding the truncated protein or variants thereof according to the invention, and a vector containing the polynucleotide.

Vectors for inserting a polynucleotide of interest are well known in the art, including, but not limited to clone vectors and expression vectors. In one embodiment, the vectors are, for example, plasmids, phages, cosmids, etc.

In another aspect, the invention also relates to a host cell comprising the polynucleotide or vector as described above. The host cell includes, but is not limited to prokaryotic cells such as *E. coli* cells, and eukaryotic cells such as yeast cells, insect cells, plant cells and animal cells (such as mammalian cells, for example, mouse cells, human cells, etc.). The host cell according to the invention may also be a cell line, such as 293T cell.

In another aspect, the invention relates to a HPV52 virus-like particle, comprising or consisting of or formed from the truncated protein or variants thereof according to the invention.

In one preferred embodiment, the HPV52 virus-like particle according to invention comprises or is consisted of or formed from the truncated HPV52 L1 protein having 27-42 amino acids, for example, 27, 35, 38, 40, or 42 amino acids, truncated at its N-terminal, as compared with wild type HPV52 L1 protein. In a particularly preferred embodiment, the HPV52 virus-like particle according to invention comprises or is consisted of or formed from the truncated HPV52 L1 protein having a sequence as set forth in SEQ ID NO: 1, 7, 10, 12, or 13.

In another aspect, the invention also relates to a composition comprising said truncated protein or variants thereof, or said polynucleotide or vector or host cell or HPV52 virus-like particle. In one preferred embodiment, the composition comprises the truncated protein or variants thereof according to the invention. In another preferred embodiment, the composition comprises the HPV52 virus-like particle according to the invention.

In another aspect, the invention also relates to a pharmaceutical composition or vaccine comprising the HPV52 virus-like particle according to invention, and optionally pharmaceutically acceptable carriers and/or excipients. The pharmaceutical composition or vaccine according to the invention is useful for preventing HPV (particularly HPV52) infection, and a disease caused by HPV (particularly HPV52) infection, such as cervical cancer.

In one preferred embodiment, the HPV52 virus-like particle is present at an amount effective for preventing HPV infection or cervical cancer. In another preferred embodiment, the pharmaceutical composition or vaccine according to the invention further comprises at least one virus-like particle selected from the group consisting of HPV6 L1 protein virus-like particle, HPV11 L1 protein virus-like particle, HPV16 L1 protein virus-like particle, HPV18 L1 protein virus-like particle, HPV31 L1 protein virus-like particle, HPV33 L1 protein virus-like particle, HPV45 L1 protein virus-like particle, and HPV58 L1 protein virus-like particle; preferably these virus-like particles are independently present at an amount effective for preventing cervical cancer or infection by the corresponding HPV subtype.

The pharmaceutical composition or vaccine according to the invention may be administrated by methods well known in the art, for example, but not limited to, orally or by injection. In the invention, the particularly preferred administration route is injection.

In one preferred embodiment, the pharmaceutical composition or vaccine according to the invention is administrated in a form of a unit dosage. For example, but not for limiting the invention, each unit dosage contains 5 μg-80 μg, preferably 20 μg-40 μg HPV52 virus-like particle.

In another aspect, the invention relates to a method for obtaining the truncated protein according to the invention, comprising expressing the truncated protein according to the invention with an *E. coli* expression system, and carrying out a purification process on the lysis supernatant containing the truncated protein, In a preferred embodiment, the method for obtaining the truncated protein according to the invention comprises
 a) expressing the truncated protein in *E. coli*;
 b) disrupting the *E. coli*, which has expressed the truncated protein, in a solution at a salt concentration of 100 mM to 600 mM, and isolating the supernatant;
 c) decreasing the salt concentration of the supernatant of b) to 100 mM or less, by using water or a solution at a low salt concentration, lowest to 0, and collecting a precipitate;
 d) re-dissolving the precipitate of c) in a solution at a salt concentration of 150 mM to 250 mM and adding a reductant to the solution, and then isolating the resultant solution, wherein the resultant solution contains the truncated HPV52 L1 protein with a purity of at least 50%.

In one embodiment of the invention, the salt concentration in b) is from 200 mM to 500 mM.

The invention also relates to a method for obtaining the HPV52 virus-like particle according to invention, on the basis of the obtainment of the truncated protein of the invention, comprising the steps of:
 e) further purifying the truncated HPV52 L1 protein according to the invention with a purity of at least 50% by a chromatography; and
 f) removing the reductant from the truncated protein obtained in e).

The invention also relates to a method for preparing a vaccine, comprising blending the HPV52 virus-like particle according to the invention, and optionally, one or more virus-like particles selected from the group consisting of virus-like particles of HPV types 6, 11, 16, 18, 31, 33, 45 and 58, with pharmaceutically acceptable carriers and/or excipients. As described above, the vaccine obtained is useful for preventing HPV (particularly HPV52) infection, and a disease caused by HPV (particularly HPV52) infection, such as cervical cancer.

In another aspect, the invention relates to a method for preventing HPV infection or a disease caused by HPV infection, comprising administrating a prophylactically effective amount of the HPV52 virus-like particle or pharmaceutical composition or vaccine according to the invention. In one preferred embodiment, the HPV infection is HPV52 infection. In another preferred embodiment, the disease caused by HPV infection includes, but is not limited to cervical cancer. In another preferred embodiment, the subject is mammalian, such as human.

In another aspect, the invention also relates to the use of the truncated protein or variants thereof or the HPV52 virus-like particle according to invention in the preparation of a pharmaceutical composition or vaccine for preventing HPV infection or a disease caused by HPV infection. In one preferred embodiment, the HPV infection is HPV52 infection. In another preferred embodiment, the disease caused by HPV infection includes, but is not limited to cervical cancer.

In another aspect, the invention also relates to the truncated protein or variants thereof or the HPV52 virus-like particle according to invention, for use in the prevention of HPV infection or a disease caused by HPV infection. In one preferred embodiment, the HPV infection is HPV52 infection. In another preferred embodiment, the disease caused by HPV infection includes, but is not limited to cervical cancer.

DEFINITIONS OF THE TERM IN PRESENT INVENTION

In the invention, unless otherwise specified, the scientific and technical terms used herein have the meanings as generally understood by a person skilled in the art. Moreover, the laboratory operations of cell culture, molecular genetics, nucleic acid chemistry, and immunology used herein are the routine operations widely used in the corresponding fields. Meanwhile, in order to better understand the invention, the definitions and explanations of the relevant terms are provided as follows.

According to the invention, the term "a protein having X amino acids truncated at its N-terminal" refers to a protein resulted from substituting the amino acid residues from positions 1 to X at the N-terminal of the protein with methionine residue encoded by an initiator codon (for initiating protein translation). For example, a HPV52 L1 protein having 27 amino acids truncated at its N-terminal refers to a protein resulted from substituting the amino acid residues from positions 1 to 27 at the N-terminal of wild type HPV52 L1 protein with methionine residue encoded by an initiator codon.

According to the invention, the term "variant" refers to a protein, whose amino acid sequence is different from the truncated HPV52 L1 protein according to the invention (for example, the protein as set forth in SEQ ID NO: 1, 7, 10, 12, or 13) by one or more (for example, 1-10, or 1-5 or 1-3) amino acids (such as conservative amino acid substitutions), or which has an identity of at least 60%, 80%, 85%, 90%, 95%, 96%, 97%, 98%, or 99% to the truncated HPV52 L1 protein according to the invention (for example, the protein as set forth in SEQ ID NO: 1, 7, 10, 12, or 13), and which retains the essential characteristics of the truncated protein. The term "essential characteristics" may be one or more of the following characteristics: capable of inducing the generation of neutralization antibodies against HPV52; capable of being expressed in *E. coli* in a soluble manner; capable of obtaining purified protein with a high yield by the expression and purification methods as involved in the invention.

According to the invention, the term "identity" refers to the match degree between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used in the invention, the term "conservative substitution" refers to amino acid substitutions which would not negatively affect or change the biological activity of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue similar to the corresponding amino acid residue physically or functionally (such as, having similar size, shape, charges, chemical properties including the capability of forming covalent bond or hydrogen bond, etc.). The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl Acad. Set USA 94: 412-417 (1997), which are incorporated herein by reference).

According to the invention, the term "E. coli expression system" refers to an expression system consisting of E. coli (strain) and a vector, wherein the E. coli (strain) includes, but are not limited to: GI698, ER2566, BL21 (DE3), B834 (DE3), BLR (DE3), etc., which are available on the market.

According to the invention, the term "vector" refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, and transfection into the host cell. Vectors are well known by a person skilled in the art, including, but not limited to plasmids, phages, cosmids and the like.

According to the invention, the term "a truncated HPV52 L1 protein" refers to the protein with one or more amino acids deleted at the N- and/or C-terminal of wild-type HPV52 L1 protein, wherein the example of the wild-type HPV52 L1 protein includes, but is not limited to, the full-length L1 proteins such as ACX32362.1, Q05138.2 or ABU55790.1 in NCBI database. For example, the amino acid sequence of wild-type HPV52 L1 protein may be as set forth in SEQ ID NO: 27, SEQ ID NO: 28 or SEQ ID NO: 29.

According to the invention, the term "a gene fragment of a truncated HPV52 L1 protein" refers to the gene fragments with the nucleotide(s) encoding one or more amino acids deleted at 5' or 3' terminal of the wild-type HPV52 L1 gene, wherein the full-length gene sequence of the wild-type HPV52 L1 gene includes, but is not limited to, the following sequences: EU077195.1, EU077194.1, FJ615303.1 in NCBI database.

According to the invention, the term "pharmaceutically acceptable carriers and/or excipients" refers to carriers and/or excipients that are pharmacologically and/or physiologically compatible with subjects and active ingredients, and are well known in the art (see, for example, Remington's Pharmaceutical Sciences. Edited by Gennaro A R, 19th ed. Pennsylvania: Mack Publishing Company, 1995), including, but not limited to pH adjusting agents, surfactants, adjuvants, and ionic strength enhancers. For example, pH adjusting agents include, but are not limited to, phosphate buffers; surfactants include, but are not limited to: anion surfactants, cation surfactants, or non-ionic surfactants (for example, Tween-80); adjuvants include, but are not limited to, aluminum adjuvants (for example, aluminum hydroxide) and Freund's adjuvants (for example, Freund's complete adjuvant); and ionic strength enhancers include, but are not limited to, NaCl.

According to the invention, the term "an effective amount" refers to an amount that can effectively achieve the intended purpose. For example, an amount effective for preventing a disease (such as HPV infection) refers to an amount effective for preventing, suppressing, or delaying the occurrence of a disease (such as HPV infection). The determination of such an effective amount is within the ability of a person skilled in the art.

According to the invention, the term "chromatography" includes, but is not limited to: ion exchange chromatography (e.g. cation-exchange chromatography), hydrophobic interaction chromatography, absorbent chromatography (e.g. hydroxyapatite chromatography), gel filtration chromatography (gel exclusion chromatography), and affinity chromatography.

According to the invention, the truncated HPV52 L1 proteins according to the invention may be obtained preferably by the following steps:

disrupting E. coli, which expresses a truncated HPV52 L1 protein, in a buffer at a salt concentration of 100-600 mM, preferably 200-500 mM, and centrifuging the disrupted solution to obtain a supernatant;

precipitating the truncated HPV52 L1 protein from the supernatant by decreasing the salt concentration of the resultant supernatant to 100 mM-0 mM with water or a low-salt solution (generally, with a salt concentration lower than the one of the buffer for disrupting);

re-dissolving the precipitate in a solution containing a reductant and having a salt concentration of 150-200 mM, preferably greater than 200 mM, resulting in a solution comprising the truncated HPV52 L1 proteins with a purity of at least 50%, preferably at least 70%, more preferably at least 80%.

The buffers used in the methods of the invention are well known in the art, including, but not limited to Tris buffers, phosphate buffers, HEPES buffers, MOPS buffers, etc.

According to the invention, the disrupting of the host cell can be accomplished by methods well known by a person skilled in the art, including, but not limited to homogenizer disrupting, ultrasonic treatment, grinding, high pressure extrusion, lysozyme treatment, etc.

The salts used in the methods of the invention include, but are not limited to: one or more of acidic salts, basic salts, neutral salts, for example, alkali metal salts, alkaline-earth metal salts, ammonium salts, hydrochlorides, sulfates, bicarbonates, phosphate salts or biphosphates, especially NaCl, KCl, NH$_4$Cl, (NH$_4$)$_2$SO$_4$. NaCl is particularly preferred. The reductant used in the methods of the invention includes, but is not limited to, DTT and 2-mercaptoethanol, at an amount including, but not limited to, 10-100 mM.

According to the invention, the HPV52 VLPs according to the invention may be produced by the following steps: further purifying the truncated HPV52 L1 protein with a purity of at least 50% as described above by e.g. a chromatography, and thereby obtaining a purified truncated protein solution; and removing the reductant from the solution to obtain the HPV52 VLPs. Methods for removing the reductant are known in the art, including, but not limited to, dialysis, ultrafiltration, and chromatography.

BENEFICIAL EFFECT

Presently, the expression systems useful for preparing HPV VLPs include eukaryotic and prokaryotic expression systems.

HPV L1 proteins expressed in eukaryotic expression systems show little conformational difference from that of the native virus, and can self-assemble into VLPs. In most cases, VLPs with a correct conformation can be obtained by simple purification. Nevertheless, eukaryotic expression systems, such as the baculovirus and yeast expression systems, are difficult to be applied to large-scale industrial production due to shortcomings such as low expression levels and high culturing costs.

Prokaryotic expression systems, such as E. coli systems, have the advantages of high expression levels and low culturing costs. However, when expressed in E. coli system, HPV L1 proteins usually lose their native conformations and are expressed in a form of inclusion bodies in the precipitant. Currently, renaturation of the protein from inclusion bodies is still a challenge worldwide. Due to the difficulty and inefficiency of renaturation, this method is limited to small-scale lab research and cannot be applied to the large-scale obtainment of VLPs with a correct conformation from the inclusive bodies. Although HPV L1 protein may be expressed in a soluble form with a correct conformation in E. coli, their expression levels are low. Moreover, it is quite difficult to purify the HPV L1 proteins from the numerous soluble proteins in the E. coli lysate supernatant. Generally, the purification is carried out by means such as fusion expression and affinity chromatography which are not feasible for industrial-scale processes due to expensive enzymes employed therein.

The N-truncated HPV52 L1 protein and the method for preparing the same, as provided in the invention, effectively solve the problem. Firstly, E. coli expression systems are used in the invention to express the N-truncated HPV52 L1 protein, which ensures a high expression level. Secondly, the truncated protein is selectively precipitated from the E. coli lysate supernatant under mild conditions. The truncated protein is then redissolved in a salt buffer to significantly improve its purity while still retaining its correct conformation. The truncated protein solution thus obtained can be further purified directly by chromatography such as ion-exchange and hydrophobic exchange chromatography so as to obtain the protein of interest with a high purity (such as a purity up to 80%). Further, the purified, truncated protein obtained from these steps, can self-assemble into VLP with good immunogenicity and the ability to induce neutralization antibodies of a high titer against HPV52, which is a good vaccine for preventing HPV52 infection in human.

Therefore, the invention has the following advantages. The truncated protein of the invention can be expressed in E. coli expression systems on a large scale whilst retaining the antigenicity, immunogenicity, and particle self-assembly ability of the full-length HPV52 L1 protein. Expensive enzymes are not required in the preparation methods used in the invention, i.e. the cost is low. Furthermore, since the truncated protein is not subjected to the intensive procedures of denaturation and renaturation during purification, the loss of the protein is low and the yield is high. The VLPs formed from the truncated protein can induce the generation of protective antibodies against HPV at a high titer and can be applied to the preparation of vaccines. Thus, the truncated protein of the invention and the preparation method thereof can be applied to large-scale industrial production, and makes the large-scale industrial production of vaccines for cervical cancer possible.

The embodiments of the invention are further described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

DESCRIPTION OF DRAWINGS

FIG. 4 shows cryo-electron microscopy photograph of HPV52N40C-L1 VLPs obtained in Example 5 and its reconstructed three-dimensional structure, as described in Example 6.

FIG. 8 shows the transmission electron microscopy (TEM) photographs of HPV52N27C-L1, HPV52N35C-L1, HPV52N38C-L1, and HPV52N42C-L1 VLPs obtained in Example 8 (taken at 50,000× magnification, Bar=100 nm).

FIG. 9 shows the dynamic light-scattering measurement results of HPV52N27C-L1, HPV52N35C-L1, HPV52N38C-L1, and HPV52N42C-L1 VLPs obtained in Example 8.

SEQUENCE INFORMATION

Figure 1:
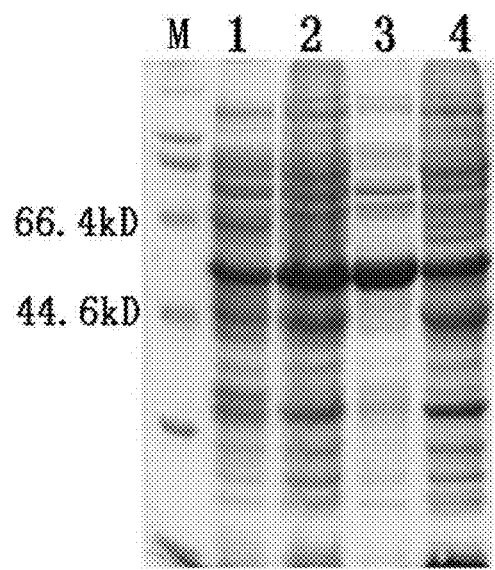
FIG. 1 shows the SDS-PAGE result of the HPV52N40C-L1 protein obtained during different steps of Example 3 of the invention. Lane M: protein molecular weight marker; Lane 1: supernatant of disrupted bacteria (i.e. the supernatant obtained by centrifuging the disrupted bacteria); Lane 2: precipitate product free of salts (i.e. the precipitate obtained by centrifugation after dialysis); Lane 3: re-dissolved supernatant (i.e. the supernatant obtained by centrifuging the solution resulted from re-dissolving the precipitate product free of salts); Lane 4: precipitant obtained after re-dissolution (i.e. the precipitate obtained by centrifuging the solution resulted from re-dissolving the precipitate product free of salts). The result showed that the purity of HPV52N40C-L1 protein was increased from about 10% (see Lane 1) to about 70% (see Lane 3) after the steps of precipitation and re-dissolution.

The information on the sequences involved in the invention is provided in the following Table 1.

TABLE 1

| SEQ ID NO: | Depiction of sequences |
|---|---|
| 1 | a HPV52 L1 protein having 27 amino acids truncated at its N-terminal, HPV52N27C-L1 |
| 2 | a HPV52 L1 protein having 30 amino acids truncated at its N-terminal, HPV52N30C-L1 |
| 3 | a HPV52 L1 protein having 31 amino acids truncated at its N-terminal, HPV52N31C-L1 |
| 4 | a HPV52 L1 protein having 32 amino acids truncated at its N-terminal, HPV52N32C-L1 |
| 5 | a HPV52 L1 protein having 33 amino acids truncated at its N-terminal, HPV52N33C-L1 |
| 6 | a HPV52 L1 protein having 34 amino acids truncated at its N-terminal, HPV52N34C-L1 |
| 7 | a HPV52 L1 protein having 35 amino acids truncated at its N-terminal, HPV52N35C-L1 |
| 8 | a HPV52 L1 protein having 36 amino acids truncated at its N-terminal, HPV52N36C-L1 |
| 9 | a HPV52 L1 protein having 37 amino acids truncated at its N-terminal, HPV52N37C-L1 |
| 10 | a HPV52 L1 protein having 38 amino acids truncated at its N-terminal, HPV52N38C-L1 |
| 11 | a HPV52 L1 protein having 39 amino acids truncated at its N-terminal, HPV52N39C-L1 |
| 12 | a HPV52 L1 protein having 40 amino acids truncated at its N-terminal, HPV52N40C-L1 |
| 13 | a HPV52 L1 protein having 42 amino acids truncated at its N-terminal, HPV52N42C-L1 |
| 14 | a DNA sequence encoding SEQ ID NO: 1 |
| 15 | a DNA sequence encoding SEQ ID NO: 2 |
| 16 | a DNA sequence encoding SEQ ID NO: 3 |
| 17 | a DNA sequence encoding SEQ ID NO: 4 |
| 18 | a DNA sequence encoding SEQ ID NO: 5 |
| 19 | a DNA sequence encoding SEQ ID NO: 6 |
| 20 | a DNA sequence encoding SEQ ID NO: 7 |
| 21 | a DNA sequence encoding SEQ ID NO: 8 |
| 22 | a DNA sequence encoding SEQ ID NO: 9 |
| 23 | a DNA sequence encoding SEQ ID NO: 10 |
| 24 | a DNA sequence encoding SEQ ID NO: 11 |
| 25 | a DNA sequence encoding SEQ ID NO: 12 |
| 26 | a DNA sequence encoding SEQ ID NO: 13 |
| 27 | the amino acid sequence of ACX32362.1 |
| 28 | the amino acid sequence of Q05138.2 |
| 29 | the amino acid sequence of ABU55790.1 |
| 30 | HPV-52 L1 gene sequence |
| 31 | primer |
| 32 | primer |

Sequence 1 (SEQ ID NO: 1):

```
  1 MSVWRPSEAT VYLPPVPVSK VVSTDEYVSR TSIYYYAGSS RLLTVGHPYF SIKNTSSGNG

61 KKVLVPKVSG LQYRVFRIKL PDPNKFGFPD TSFYNPETQR LVWACTGLEI GRGQPLGVGI

121 SGHPLLNKFD DTETSNKYAG KPGIDNRECL SMDYKQTQLC ILGCKPPIGE HWGKGTPCNN
```

-continued

```
181 NSGNPGDCPP LQLINSVIQD GDMVDTGFGC MDFNTLQASK SDVPIDICSS VCKYPDYLQM

241 ASEPYGDSLF FFLRREQMFV RHFFNRAGTL GDPVPGDLYI QGSNSGNTAT VQSSAFFPTP

301 SGSMVTSESQ LFNKPYWLQR AQGHNNGICW GNQLFVTVVD TTRSTNMTLC AEVKKESTYK

361 NENFKEYLRH GEEFDLQFIF QLCKITLTAD VMTYIHKMDA TILEDWQFGL TPPPSASLED

421 TYRFVTSTAI TCQKNTPPKG KEDPLKDYMF WEVDLKEKFS ADLDQFPLGR KFLLQAGLQA

481 RPKLKRPASS APRTSTKKKK VKR

Sequence 2 (SEQ ID NO: 2):
  1 MRPSEATVYL PPVPVSKVVS TDEYVSRTSI YYYAGSSRLL TVGHPYFSIK NTSSGNGKKV

61 LVPKVSGLQY RVFRIKLPDP NKFGFPDTSF YNPETQRLVW ACTGLEIGRG QPLGVGISGH

121 PLLNKFDDTE TSNKYAGKPG IDNRECLSMD YKQTQLCILG CKPPIGEHWG KGTPCNNNSG

181 NPGDCPPLQL INSVIQDGDM VDTGFGCMDF NTLQASKSDV PIDICSSVCK YPDYLQMASE

241 PYGDSLFFFL RREQMFVRHF FNRAGTLGDP VPGDLYIQGS NSGNTATVQS SAFFPTPSGS

301 MVTSESQLFN KPYWLQRAQG HNNGICWGNQ LFVTVVDTTR STNMTLCAEV KKESTYKNEN

361 FKEYLRHGEE FDLQFIFQLC KITLTADVMT YIHKMDATIL EDWQFGLTPP PSASLEDTYR

421 FVTSTAITCQ KNTPPKGKED PLKDYMFWEV DLKEKFSADL DQFPLGRKFL LQAGLQARPK

481 LKRPASSAPR TSTKKKKVKR

Sequence 3 (SEQ ID NO: 3):
  1 MPSEATVYLP PVPVSKVVST DEYVSRTSIY YYAGSSRLLT VGHPYFSIKN TSSGNGKKVL

61 VPKVSGLQYR VFRIKLPDPN KFGFPDTSFY NPETQRLVWA CTGLEIGRGQ PLGVGISGHP

121 LLNKFDDTET SNKYAGKPGI DNRECLSMDY KQTQLCILGC KPPIGEHWGK GTPCNNNSGN

181 PGDCPPLQLI NSVIQDGDMV DTGFGCMDFN TLQASKSDVP IDICSSVCKY PDYLQMASEP

241 YGDSLFFFLR REQMFVRHFF NRAGTLGDPV PGDLYIQGSN SGNTATVQSS AFFPTPSGSM

301 VTSESQLFNK PYWLQRAQGH NNGICWGNQL FVTVVDTTRS TNMTLCAEVK KESTYKNENF

361 KEYLRHGEEF DLQFIFQLCK ITLTADVMTY IHKMDATILE DWQFGLTPPP SASLEDTYRF

421 VTSTAITCQK NTPPKGKEDP LKDYMFWEVD LKEKFSADLD QFPLGRKFLL QAGLQARPKL

481 KRPASSAPRT STKKKKVKR

Sequence 4 (SEQ ID NO: 4):
  1 MSEATVYLPP VPVSKVVSTD EYVSRTSIYY YAGSSRLLTV GHPYFSIKNT SSGNGKKVLV

61 PKVSGLQYRV FRIKLPDPNK FGFPDTSFYN PETQRLVWAC TGLEIGRGQP LGVGISGHPL

121 LNKFDDTETS NKYAGKPGID NRECLSMDYK QTQLCILGCK PPIGEHWGKG TPCNNNSGNP

181 GDCPPLQLIN SVIQDGDMVD TGFGCMDFNT LQASKSDVPI DICSSVCKYP DYLQMASEPY

241 GDSLFFFLRR EQMFVRHFFN RAGTLGDPVP GDLYIQGSNS GNTATVQSSA FFPTPSGSMV

301 TSESQLFNKP YWLQRAQGHN NGICWGNQLF VTVVDTTRST NMTLCAEVKK ESTYKNENFK

361 EYLRHGEEFD LQFIFQLCKI TLTADVMTYI HKMDATILED WQFGLTPPPS ASLEDTYRFV

421 TSTAITCQKN TPPKGKEDPL KDYMFWEVDL KEKFSADLDQ FPLGRKFLLQ AGLQARPKLK

481 RPASSAPRTS TKKKKVKR

Sequence 5 (SEQ ID NO: 5):
  1 MEATVYLPPV PVSKVVSTDE YVSRTSIYYY AGSSRLLTVG HPYFSIKNTS SGNGKKVLVP

61 KVSGLQYRVF RIKLPDPNKF GFPDTSFYNP ETQRLVWACT GLEIGRGQPL GVGISGHPLL

121 NKFDDTETSN KYAGKPGIDN RECLSMDYKQ TQLCILGCKP PIGEHWGKGT PCNNNSGNPG

181 DCPPLQLINS VIQDGDMVDT GFGCMDFNTL QASKSDVPID ICSSVCKYPD YLQMASEPYG

241 DSLFFFLRRE QMFVRHFFNR AGTLGDPVPG DLYIQGSNSG NTATVQSSAF FPTPSGSMVT
```

```
301 SESQLFNKPY WLQRAQGHNN GICWGNQLFV TVVDTTRSTN MTLCAEVKKE STYKNENFKE

361 YLRHGEEFDL QFIFQLCKIT LTADVMTYIH KMDATILEDW QFGLTPPPSA SLEDTYRFVT

421 STAITCQKNT PPKGKEDPLK DYMFWEVDLK EKFSADLDQF PLGRKFLLQA GLQARPKLKR

481 PASSAPRTST KKKKVKR

Sequence 6 (SEQ ID NO: 6):
  1 MATVYLPPVP VSKVVSTDEY VSRTSIYYYA GSSRLLTVGH PYFSIKNTSS GNGKKVLVPK

61 VSGLQYRVFR IKLPDPNKFG FPDTSFYNPE TQRLVWACTG LEIGRGQPLG VGISGHPLLN

121 KFDDTETSNK YAGKPGIDNR ECLSMDYKQT QLCILGCKPP IGEHWGKGTP CNNNSGNPGD

181 CPPLQLINSV IQDGDMVDTG FGCMDFNTLQ ASKSDVPIDI CSSVCKYPDY LQMASEPYGD

241 SLFFFLRREQ MFVRHFFNRA GTLGDPVPGD LYIQGSNSGN TATVQSSAFF PTPSGSMVTS

301 ESQLFNKPYW LQRAQGHNNG ICWGNQLFVT VVDTTRSTNM TLCAEVKKES TYKNENFKEY

361 LRHGEEFDLQ FIFQLCKITL TADVMTYIHK MDATILEDWQ FGLTPPPSAS LEDTYRFVTS

421 TAITCQKNTP PKGKEDPLKD YMFWEVDLKE KFSADLDQFP LGRKFLLQAG LQARPKLKRP

481 ASSAPRTSTK KKKVKR

Sequence 7 (SEQ ID NO: 7):
  1 MTVYLPPVPV SKVVSTDEYV SRTSIYYYAG SSRLLTVGHP YFSIKNTSSG NGKKVLVPKV

61 SGLQYRVFRI KLPDPNKFGF PDTSFYNPET QRLVWACTGL EIGRGQPLGV GISGHPLLNK

121 FDDTETSNKY AGKPGIDNRE CLSMDYKQTQ LCILGCKPPI GEHWGKGTPC NNNSGNPGDC

181 PPLQLINSVI QDGDMVDTGF GCMDFNTLQA SKSDVPIDIC SSVCKYPDYL QMASEPYGDS

241 LFFFLRREQM FVRHFFNRAG TLGDPVPGDL YIQGSNSGNT ATVQSSAFFP TPSGSMVTSE

301 SQLFNKPYWL QRAQGHNNGI CWGNQLFVTV VDTTRSTNMT LCAEVKKEST YKNENFKEYL

361 RHGEEFDLQF IFQLCKITLT ADVMTYIHKM DATILEDWQF GLTPPPSASL EDTYRFVTST

421 AITCQKNTPP KGKEDPLKDY MFWEVDLKEK FSADLDQFPL GRKFLLQAGL QARPKLKRPA

481 SSAPRTSTKK KKVKR

Sequence 8 (SEQ ID NO: 8):
  1 MVYLPPVPVS KVVSTDEYVS RTSIYYYAGS SRLLTVGHPY FSIKNTSSGN GKKVLVPKVS

61 GLQYRVFRIK LPDPNKFGFP DTSFYNPETQ RLVWACTGLE IGRGQPLGVG ISGHPLLNKF

121 DDTETSNKYA GKPGIDNREC LSMDYKQTQL CILGCKPPIG EHWGKGTPCN NNSGNPGDCP

181 PLQLINSVIQ DGDMVDTGFG CMDFNTLQAS KSDVPIDICS SVCKYPDYLQ MASEPYGDSL

241 FFFLRREQMF VRHFFNRAGT LGDPVPGDLY IQGSNSGNTA TVQSSAFFPT PSGSMVTSES

301 QLFNKPYWLQ RAQGHNNGIC WGNQLFVTVV DTTRSTNMTL CAEVKKESTY KNENFKEYLR

361 HGEEFDLQFI FQLCKITLTA DVMTYIHKMD ATILEDWQFG LTPPPSASLE DTYRFVTSTA

421 ITCQKNTPPK GKEDPLKDYM FWEVDLKEKF SADLDQFPLG RKFLLQAGLQ ARPKLKRPAS

481 SAPRTSTKKK KVKR

Sequence 9 (SEQ ID NO: 9):
  1 MYLPPVPVSK VVSTDEYVSR TSIYYYAGSS RLLTVGHPYF SIKNTSSGNG KKVLVPKVSG

61 LQYRVFRIKL PDPNKFGFPD TSFYNPETQR LVWACTGLEI GRGQPLGVGI SGHPLLNKFD

121 DTETSNKYAG KPGIDNRECL SMDYKQTQLC ILGCKPPIGE HWGKGTPCNN NSGNPGDCPP

181 LQLINSVIQD GDMVDTGFGC MDFNTLQASK SDVPIDICSS VCKYPDYLQM ASEPYGDSLF

241 FFLRREQMFV RHFFNRAGTL GDPVPGDLYI QGSNSGNTAT VQSSAFFPTP SGSMVTSESQ

301 LFNKPYWLQR AQGHNNGICW GNQLFVTVVD TTRSTNMTLC AEVKKESTYK NENFKEYLRH

361 GEEFDLQFIF QLCKITLTAD VMTYIHKMDA TILEDWQFGL TPPPSASLED TYRFVTSTAI
```

```
421 TCQKNTPPKG KEDPLKDYMF WEVDLKEKFS ADLDQFPLGR KFLLQAGLQA RPKLKRPASS

481 APRTSTKKKK VKR

Sequence 10 (SEQ ID NO: 10):
  1 MLPPVPVSKV VSTDEYVSRT SIYYYAGSSR LLTVGHPYFS IKNTSSGNGK KVLVPKVSGL

61 QYRVFRIKLP DPNKFGFPDT SFYNPETQRL VWACTGLEIG RGQPLGVGIS GHPLLNKFDD

121 TETSNKYAGK PGIDNRECLS MDYKQTQLCI LGCKPPIGEH WGKGTPCNNN SGNPGDCPPL

181 QLINSVIQDG DMVDTGFGCM DFNTLQASKS DVPIDICSSV CKYPDYLQMA SEPYGDSLFF

241 FLRREQMFVR HFFNRAGTLG DPVPGDLYIQ GSNSGNTATV QSSAFFPTPS GSMVTSESQL

301 FNKPYWLQRA QGHNNGICWG NQLFVTVVDT TRSTNMTLCA EVKKESTYKN ENFKEYLRHG

361 EEFDLQFIFQ LCKITLTADV MTYIHKMDAT ILEDWQFGLT PPPSASLEDT YRFVTSTAIT

421 CQKNTPPKGK EDPLKDYMFW EVDLKEKFSA DLDQFPLGRK FLLQAGLQAR PKLKRPASSA

481 PRTSTKKKKV KR

Sequence 11 (SEQ ID NO: 11):
  1 MPPVPVSKVV STDEYVSRTS IYYYAGSSRL LTVGHPYFSI KNTSSGNGKK VLVPKVSGLQ

61 YRVFRIKLPD PNKFGFPDTS FYNPETQRLV WACTGLEIGR GQPLGVGISG HPLLNKFDDT

121 ETSNKYAGKP GIDNRECLSM DYKQTQLCIL GCKPPIGEHW GKGTPCNNNS GNPGDCPPLQ

181 LINSVIQDGD MVDTGFGCMD FNTLQASKSD VPIDICSSVC KYPDYLQMAS EPYGDSLFFF

241 LRREQMFVRH FFNRAGTLGD PVPGDLYIQG SNSGNTATVQ SSAFFPTPSG SMVTSESQLF

301 NKPYWLQRAQ GHNNGICWGN QLFVTVVDTT RSTNMTLCAE VKKESTYKNE NFKEYLRHGE

361 EFDLQFIFQL CKITLTADVM TYIHKMDATI LEDWQFGLTP PPSASLEDTY RFVTSTAITC

421 QKNTPPKGKE DPLKDYMFWE VDLKEKFSAD LDQFPLGRKF LLQAGLQARP KLKRPASSAP

481 RTSTKKKKVK R

Sequence 12 (SEQ ID NO: 12):
  1 MPVPVSKVVS TDEYVSRTSI YYYAGSSRLL TVGHPYFSIK NTSSGNGKKV LVPKVSGLQY

61 RVFRIKLPDP NKFGFPDTSF YNPETQRLVW ACTGLEIGRG QPLGVGISGH PLLNKFDDTE

121 TSNKYAGKPG IDNRECLSMD YKQTQLCILG CKPPIGEHWG KGTPCNNNSG NPGDCPPLQL

181 INSVIQDGDM VDTGFGCMDF NTLQASKSDV PIDICSSVCK YPDYLQMASE PYGDSLFFFL

241 RREQMFVRHF FNRAGTLGDP VPGDLYIQGS NSGNTATVQS SAFFPTPSGS MVTSESQLFN

301 KPYWLQRAQG HNNGICWGNQ LFVTVVDTTR STNMTLCAEV KKESTYKNEN FKEYLRHGEE

361 FDLQFIFQLC KITLTADVMT YIHKMDATIL EDWQFGLTPP PSASLEDTYR FVTSTAITCQ

421 KNTPPKGKED PLKDYMFWEV DLKEKFSADL DQFPLGRKFL QAGLQARPK LKRPASSAPR

481 TSTKKKKVKR

Sequence 13 (SEQ ID NO: 13):
  1 MPVSKVVSTD EYVSRTSIYY YAGSSRLLTV GHPYFSIKNT SSGNGKKVLV PKVSGLQYRV

61 FRIKLPDPNK FGFPDTSFYN PETQRLVWAC TGLEIGRGQP LGVGISGHPL LNKFDDTETS

121 NKYAGKPGID NRECLSMDYK QTQLCILGCK PPIGEHWGKG TPCNNNSGNP GDCPPLQLIN

181 SVIQDGDMVD TGFGCMDFNT LQASKSDVPI DICSSVCKYP DYLQMASEPY GDSLFFFLRR

241 EQMFVRHFFN RAGTLGDPVP GDLYIQGSNS GNTATVQSSA FFPTPSGSMV TSESQLFNKP

301 YWLQRAQGHN NGICWGNQLF VTVVDTTRST NMTLCAEVKK ESTYKNENFK EYLRHGEEFD

361 LQFIFQLCKI TLTADVMTYI HKMDATILED WQFGLTPPPS ASLEDTYRFV TSTAITCQKN

421 TPPKGKEDPL KDYMFWEVDL KEKFSADLDQ FPLGRKFLLQ AGLQARPKLK RPASSAPRTS

481 TKKKKVKR
```

Sequence 14 (SEQ ID NO: 14):
```
   1 ATGAGCGTGT GGAGGCCCAG CGAGGCCACC GTGTACCTGC CCCCCGTGCC CGTGAGCAAG

61 GTGGTGAGCA CCGACGAGTA CGTGAGCAGG ACCAGCATCT ACTACTACGC CGGCAGCAGC

121 AGGCTGCTGA CCGTGGGCCA CCCCTACTTC AGCATCAAGA CACCAGCAG CGGCAACGGC

181 AAGAAGGTGC TGGTGCCCAA GGTGAGCGGC CTGCAGTACA GGGTGTTCAG GATCAAGCTG

241 CCCGACCCCA ACAAGTTCGG CTTCCCCGAC ACCAGCTTCT ACAACCCCGA GACCCAGAGG

301 CTGGTGTGGG CCTGCACCGG CCTGGAGATC GGCAGGGGCC AGCCCCTGGG CGTGGGCATC

361 AGCGGCCACC CCCTGCTGAA CAAGTTCGAC GACACCGAGA CCAGCAACAA GTACGCCGGC

421 AAGCCCGGCA TCGACAACAG GGAGTGCCTG AGCATGGACT ACAAGCAGAC CCAGCTGTGC

481 ATCCTGGGCT GCAAGCCCCC CATCGGCGAG CACTGGGGCA AGGGCACCCC CTGCAACAAC

541 AACAGCGGCA CCCCGGCGA CTGCCCCCC CTGCAGCTGA TCAACAGCGT GATCCAGGAC

601 GGCGACATGG TGGACACCGG CTTCGGCTGC ATGGACTTCA ACACCCTGCA GGCCAGCAAG

661 AGCGACGTGC CCATCGACAT CTGCAGCAGC GTGTGCAAGT ACCCCGACTA CCTGCAGATG

721 GCCAGCGAGC CCTACGGCGA CAGCCTGTTC TTCTTCCTGA GGAGGGAGCA GATGTTCGTG

781 AGGCACTTCT TCAACAGGGC CGGCACCCTG GGCGACCCCG TGCCCGGCGA CCTGTACATC

841 CAGGGCAGCA ACAGCGGCAA CACCGCCACC GTGCAGAGCA GCGCCTTCTT CCCCACCCCC

901 AGCGGCAGCA TGGTGACCAG CGAGAGCCAG CTGTTCAACA AGCCCTACTG GCTGCAGAGG

961 GCCCAGGGCC ACAACAACGG CATCTGCTGG GGCAACCAGC TGTTCGTGAC CGTGGTGGAC

1021 ACCACCAGGA GCACCAACAT GACCCTGTGC GCCGAGGTGA AGAAGGAGAG CACCTACAAG

1081 AACGAGAACT TCAAGGAGTA CCTGAGGCAC GGCGAGGAGT TCGACCTGCA GTTCATCTTC

1141 CAGCTGTGCA AGATCACCCT GACCGCCGAC GTGATGACCT ACATCCACAA GATGGACGCC

1201 ACCATCCTGG AGGACTGGCA GTTCGGCCTG ACCCCCCCCC CCAGCGCCAG CCTGGAGGAC

1261 ACCTACAGGT TCGTGACCAG CACCGCCATC ACCTGCCAGA GAACACCCC CCCCAAGGGC

1321 AAGGAGGACC CCCTGAAGGA CTACATGTTC TGGGAGGTGG ACCTGAAGGA GAAGTTCAGC

1381 GCCGACCTGG ACCAGTTCCC CCTGGGCAGG AAGTTCCTGC TGCAGGCCGG CCTGCAGGCC

1441 AGGCCCAAGC TGAAGAGGCC CGCCAGCAGC GCCCCCAGGA CCAGCACCAA GAAGAAGAAG

1501 GTGAAGAGGT GA
```

Sequence 15 (SEQ ID NO: 15):
```
   1 ATGAGGCCCA GCGAGGCCAC CGTGTACCTG CCCCCCGTGC CCGTGAGCAA GGTGGTGAGC

61 ACCGACGAGT ACGTGAGCAG GACCAGCATC TACTACTACG CCGGCAGCAG CAGGCTGCTG

121 ACCGTGGGCC ACCCCTACTT CAGCATCAAG AACACCAGCA GCGGCAACGG CAAGAAGGTG

181 CTGGTGCCCA AGGTGAGCGG CCTGCAGTAC AGGGTGTTCA GGATCAAGCT GCCCGACCCC

241 AACAAGTTCG GCTTCCCCGA CACCAGCTTC TACAACCCCG AGACCCAGAG GCTGGTGTGG

301 GCCTGCACCG GCCTGGAGAT CGGCAGGGGC CAGCCCCTGG GCGTGGGCAT CAGCGGCCAC

361 CCCCTGCTGA ACAAGTTCGA CGACACCGAG ACCAGCAACA AGTACGCCGG CAAGCCCGGC

421 ATCGACAACA GGGAGTGCCT GAGCATGGAC TACAAGCAGA CCCAGCTGTG CATCCTGGGC

481 TGCAAGCCCC CCATCGGCGA GCACTGGGGC AAGGGCACCC CTGCAACAA CAACAGCGGC

541 AACCCCGGCG ACTGCCCCCC CCTGCAGCTG ATCAACAGCG TGATCCAGGA CGGCGACATG

601 GTGGACACCG GCTTCGGCTG CATGGACTTC AACACCCTGC AGGCCAGCAA GAGCGACGTG

661 CCCATCGACA TCTGCAGCAG CGTGTGCAAG TACCCCGACT ACCTGCAGAT GGCCAGCGAG

721 CCCTACGGCG ACAGCCTGTT CTTCTTCCTG AGGAGGGAGC AGATGTTCGT GAGGCACTTC

781 TTCAACAGGG CCGGCACCCT GGGCGACCCC GTGCCCGGCG ACCTGTACAT CCAGGGCAGC
```

-continued

```
 841 AACAGCGGCA ACACCGCCAC CGTGCAGAGC AGCGCCTTCT TCCCCACCCC CAGCGGCAGC
 901 ATGGTGACCA GCGAGAGCCA GCTGTTCAAC AAGCCCTACT GGCTGCAGAG GGCCCAGGGC
 961 CACAACAACG GCATCTGCTG GGGCAACCAG CTGTTCGTGA CCGTGGTGGA CACCACCAGG
1021 AGCACCAACA TGACCCTGTG CGCCGAGGTG AAGAAGGAGA GCACCTACAA GAACGAGAAC
1081 TTCAAGGAGT ACCTGAGGCA CGGCGAGGAG TTCGACCTGC AGTTCATCTT CCAGCTGTGC
1141 AAGATCACCC TGACCGCCGA CGTGATGACC TACATCCACA GATGGACGC CACCATCCTG
1201 GAGGACTGGC AGTTCGGCCT GACCCCCCCC CCCAGCGCCA GCCTGGAGGA CACCTACAGG
1261 TTCGTGACCA GCACCGCCAT CACCTGCCAG AAGAACACCC CCCCCAAGGG CAAGGAGGAC
1321 CCCCTGAAGG ACTACATGTT CTGGGAGGTG GACCTGAAGG AGAAGTTCAG CGCCGACCTG
1381 GACCAGTTCC CCCTGGGCAG GAAGTTCCTG CTGCAGGCCG GCCTGCAGGC CAGGCCCAAG
1441 CTGAAGAGGC CCGCCAGCAG CGCCCCCAGG ACCAGCACCA AGAAGAAGAA GGTGAAGAGG
1501 TGA
Sequence 16 (SEQ ID NO: 16):
   1 ATGCCCAGCG AGGCCACCGT GTACCTGCCC CCCGTGCCCG TGAGCAAGGT GGTGAGCACC
  61 GACGAGTACG TGAGCAGGAC CAGCATCTAC TACTACGCCG GCAGCAGCAG GCTGCTGACC
 121 GTGGGCCACC CCTACTTCAG CATCAAGAAC ACCAGCAGCG GCAACGGCAA GAAGGTGCTG
 181 GTGCCCAAGG TGAGCGGCCT GCAGTACAGG GTGTTCAGGA TCAAGCTGCC CGACCCCAAC
 241 AAGTTCGGCT TCCCCGACAC CAGCTTCTAC AACCCCGAGA CCCAGAGGCT GGTGTGGGCC
 301 TGCACCGGCC TGGAGATCGG CAGGGGCCAG CCCCTGGGCG TGGGCATCAG CGGCCACCCC
 361 CTGCTGAACA AGTTCGACGA CACCGAGACC AGCAACAAGT ACGCCGGCAA GCCCGGCATC
 421 GACAACAGGG AGTGCCTGAG CATGGACTAC AAGCAGACCC AGCTGTGCAT CCTGGGCTGC
 481 AAGCCCCCCA TCGGCGAGCA CTGGGGCAAG GCACCCCCT GCAACAACAA CAGCGGCAAC
 541 CCCGGCGACT GCCCCCCCCT GCAGCTGATC AACAGCGTGA TCCAGGACGG CGACATGGTG
 601 GACACCGGCT TCGGCTGCAT GGACTTCAAC ACCCTGCAGG CCAGCAAGAG CGACGTGCCC
 661 ATCGACATCT GCAGCAGCGT GTGCAAGTAC CCCGACTACC TGCAGATGGC CAGCGAGCCC
 721 TACGCGACA GCCTGTTCTT CTTCCTGAGG AGGGAGCAGA TGTTCGTGAG GCACTTCTTC
 781 AACAGGGCCG GCACCCTGGG CGACCCCGTG CCCGGCGACC TGTACATCCA GGGCAGCAAC
 841 AGCGGCAACA CCGCCACCGT GCAGAGCAGC GCCTTCTTCC CCACCCCCAG CGGCAGCATG
 901 GTGACCAGCG AGAGCCAGCT GTTCAACAAG CCCTACTGGC TGCAGAGGGC CAGGGCCAC
 961 AACAACGGCA TCTGCTGGGG CAACCAGCTG TTCGTGACCG TGGTGGACAC CACCAGGAGC
1021 ACCAACATGA CCCTGTGCGC CGAGGTGAAG AAGGAGAGCA CCTACAAGAA CGAGAACTTC
1081 AAGGAGTACC TGAGGCACGG CGAGGAGTTC GACCTGCAGT TCATCTTCCA GCTGTGCAAG
1141 ATCACCCTGA CCGCCGACGT GATGACCTAC ATCCACAAGA TGGACGCCAC CATCCTGGAG
1201 GACTGGCAGT TCGGCCTGAC CCCCCCCCCC AGCGCCAGCC TGGAGGACAC CTACAGGTTC
1261 GTGACCAGCA CCGCCATCAC CTGCCAGAAG AACACCCCCC CCAAGGGCAA GGAGGACCCC
1321 CTGAAGGACT ACATGTTCTG GGAGGTGGAC CTGAAGGAGA AGTTCAGCGC CGACCTGGAC
1381 CAGTTCCCCC TGGGCAGGAA GTTCCTGCTG CAGGCCGGCC TGCAGGCCAG CCCCAAGCTG
1441 AAGAGGCCCG CCAGCAGCGC CCCCAGGACC AGCACCAAGA AGAAGAAGGT GAAGAGGTGA
Sequence 17 (SEQ ID NO: 17):
   1 ATGAGCGAGG CCACCGTGTA CCTGCCCCCC GTGCCCGTGA GCAAGGTGGT GAGCACCGAC
  61 GAGTACGTGA GCAGGACCAG CATCTACTAC TACGCCGGCA GCAGCAGGCT GCTGACCGTG
```

-continued

```
 121 GGCCACCCCT ACTTCAGCAT CAAGAACACC AGCAGCGGCA ACGGCAAGAA GGTGCTGGTG
 181 CCCAAGGTGA GCGGCCTGCA GTACAGGGTG TTCAGGATCA AGCTGCCCGA CCCCAACAAG
 241 TTCGGCTTCC CCGACACCAG CTTCTACAAC CCCGAGACCC AGAGGCTGGT GTGGGCCTGC
 301 ACCGGCCTGG AGATCGGCAG GGGCCAGCCC TGGGCGTGG GCATCAGCGG CCACCCCCTG
 361 CTGAACAAGT TCGACGACAC CGAGACCAGC AACAAGTACG CCGGCAAGCC CGGCATCGAC
 421 AACAGGGAGT GCCTGAGCAT GGACTACAAG CAGACCCAGC TGTGCATCCT GGGCTGCAAG
 481 CCCCCCATCG GCGAGCACTG GGGCAAGGGC ACCCCCTGCA ACAACAACAG CGGCAACCCC
 541 GGCGACTGCC CCCCCCTGCA GCTGATCAAC AGCGTGATCC AGGACGGCGA CATGGTGGAC
 601 ACCGGCTTCG GCTGCATGGA CTTCAACACC CTGCAGGCCA GCAAGAGCGA CGTGCCCATC
 661 GACATCTGCA GCAGCGTGTG CAAGTACCCC GACTACCTGC AGATGGCCAG CGAGCCCTAC
 721 GGCGACAGCC TGTTCTTCTT CCTGAGGAGG GAGCAGATGT TCGTGAGGCA CTTCTTCAAC
 781 AGGGCCGGCA CCCTGGGCGA CCCCGTGCCC GGCGACCTGT ACATCCAGGG CAGCAACAGC
 841 GGCAACACCG CCACCGTGCA GAGCAGCGCC TTCTTCCCCA CCCCCAGCGG CAGCATGGTG
 901 ACCAGCGAGA GCCAGCTGTT CAACAAGCCC TACTGGCTGC AGAGGGCCCA GGGCCACAAC
 961 AACGGCATCT GCTGGGGCAA CCAGCTGTTC GTGACCGTGG TGGACACCAC CAGGAGCACC
1021 AACATGACCC TGTGCGCCGA GGTGAAGAAG GAGAGCACCT ACAAGAACGA GAACTTCAAG
1081 GAGTACCTGA GGCACGGCGA GGAGTTCGAC CTGCAGTTCA TCTTCCAGCT GTGCAAGATC
1141 ACCCTGACCG CCGACGTGAT GACCTACATC CACAAGATGG ACGCCACCAT CCTGGAGGAC
1201 TGGCAGTTCG GCCTGACCCC CCCCCCCAGC GCCAGCCTGG AGGACACCTA CAGGTTCGTG
1261 ACCAGCACCG CCATCACCTG CCAGAAGAAC ACCCCCCCCA AGGGCAAGGA GGACCCCCTG
1321 AAGGACTACA TGTTCTGGGA GGTGGACCTG AAGGAGAAGT TCAGCGCCGA CCTGGACCAG
1381 TTCCCCCTGG GCAGGAAGTT CCTGCTGCAG GCCGGCCTGC AGGCCAGGCC CAAGCTGAAG
1441 AGGCCCGCCA GCAGCGCCCC CAGGACCAGC ACCAAGAAGA GAAGGTGAA GAGGTGA
```

Sequence 18 (SEQ ID NO: 18):
```
   1 ATGGAGGCCA CCGTGTACCT GCCCCCCGTG CCCGTGAGCA AGGTGGTGAG CACCGACGAG
  61 TACGTGAGCA GGACCAGCAT CTACTACTAC GCCGGCAGCA GCAGGCTGCT GACCGTGGGC
 121 CACCCCTACT TCAGCATCAA GAACACCAGC AGCGGCAACG GCAAGAAGGT GCTGGTGCCC
 181 AAGGTGAGCG GCCTGCAGTA CAGGGTGTTC AGGATCAAGC TGCCCGACCC CAACAAGTTC
 241 GGCTTCCCCG ACACCAGCTT CTACAACCCC GAGACCCAGA GGCTGGTGTG GGCCTGCACC
 301 GGCCTGGAGA TCGGCAGGGG CCAGCCCCTG GGCGTGGGCA TCAGCGGCCA CCCCCTGCTG
 361 AACAAGTTCG ACGACACCGA GACCAGCAAC AAGTACGCCG GCAAGCCCGG CATCGACAAC
 421 AGGGAGTGCC TGAGCATGGA CTACAAGCAG ACCCAGCTGT GCATCCTGGG CTGCAAGCCC
 481 CCCATCGGCG AGCACTGGGG CAAGGGCACC CCTGCAACA ACAACAGCGG CAACCCCGGC
 541 GACTGCCCCC CCTGCAGCT GATCAACAGC GTGATCCAGG ACGGCGACAT GGTGGACACC
 601 GGCTTCGGCT GCATGGACTT CAACACCCTG CAGGCCAGCA AGAGCGACGT GCCCATCGAC
 661 ATCTGCAGCA GCGTGTGCAA GTACCCCGAC TACCTGCAGA TGGCCAGCGA GCCCTACGGC
 721 GACAGCCTGT TCTTCTTCCT GAGGAGGGAG CAGATGTTCG TGAGGCACTT CTTCAACAGG
 781 GCCGGCACCC TGGGCGACCC CGTGCCCGGC GACCTGTACA TCCAGGGCAG CAACAGCGGC
 841 AACACCGCCA CCGTGCAGAG CAGCGCCTTC TTCCCCACCC CCAGCGGCAG CATGGTGACC
 901 AGCGAGAGCC AGCTGTTCAA CAAGCCCTAC TGGCTGCAGA GGGCCCAGGG CCACAACAAC
 961 GGCATCTGCT GGGGCAACCA GCTGTTCGTG ACCGTGGTGG ACACCACCAG GAGCACCAAC
```

```
1021 ATGACCCTGT GCGCCGAGGT GAAGAAGGAG AGCACCTACA AGAACGAGAA CTTCAAGGAG

1081 TACCTGAGGC ACGGCGAGGA GTTCGACCTG CAGTTCATCT TCCAGCTGTG CAAGATCACC

1141 CTGACCGCCG ACGTGATGAC CTACATCCAC AAGATGGACG CCACCATCCT GGAGGACTGG

1201 CAGTTCGGCC TGACCCCCCC CCCCAGCGCC AGCCTGGAGG ACACCTACAG GTTCGTGACC

1261 AGCACCGCCA TCACCTGCCA GAAGAACACC CCCCCAAGG GCAAGGAGGA CCCCCTGAAG

1321 GACTACATGT TCTGGGAGGT GGACCTGAAG GAGAAGTTCA GCGCCGACCT GGACCAGTTC

1381 CCCCTGGGCA GGAAGTTCCT GCTGCAGGCC GGCCTGCAGG CCAGGCCCAA GCTGAAGAGG

1441 CCCGCCAGCA GCGCCCCCAG GACCAGCACC AAGAAGAAGA AGGTGAAGAG GTGA
```

Sequence 19 (SEQ ID NO: 19):
```
   1 ATGGCCACCG TGTACCTGCC CCCCGTGCCC GTGAGCAAGG TGGTGAGCAC CGACGAGTAC

61 GTGAGCAGGA CCAGCATCTA CTACTACGCC GGCAGCAGCA GGCTGCTGAC CGTGGGCCAC

121 CCCTACTTCA GCATCAAGAA CACCAGCAGC GGCAACGGCA AGAAGGTGCT GGTGCCCAAG

181 GTGAGCGGCC TGCAGTACAG GGTGTTCAGG ATCAAGCTGC CCGACCCCAA CAAGTTCGGC

241 TTCCCCGACA CCAGCTTCTA CAACCCCGAG ACCCAGAGGC TGGTGTGGGC CTGCACCGGC

301 CTGGAGATCG CAGGGGCCA GCCCCTGGGC GTGGGCATCA GCGGCCACCC CCTGCTGAAC

361 AAGTTCGACG ACACCGAGAC CAGCAACAAG TACGCCGGCA AGCCCGGCAT CGACAACAGG

421 GAGTGCCTGA GCATGGACTA CAAGCAGACC CAGCTGTGCA TCCTGGGCTG CAAGCCCCCC

481 ATCGGCGAGC ACTGGGGCAA GGGCACCCCC TGCAACAACA ACAGCGGCAA CCCCGGCGAC

541 TGCCCCCCCC TGCAGCTGAT CAACAGCGTG ATCCAGGACG GCGACATGGT GGACACCGGC

601 TTCGGCTGCA TGGACTTCAA CACCCTGCAG GCCAGCAAGA GCGACGTGCC CATCGACATC

661 TGCAGCAGCG TGTGCAAGTA CCCCGACTAC CTGCAGATGG CCAGCGAGCC CTACGGCGAC

721 AGCCTGTTCT TCTTCCTGAG GAGGGAGCAG ATGTTCGTGA GGCACTTCTT CAACAGGGCC

781 GGCACCCTGG CGACCCCGT GCCCGGCGAC CTGTACATCC AGGGCAGCAA CAGCGGCAAC

841 ACCGCCACCG TGCAGAGCAG CGCCTTCTTC CCCACCCCCA GCGGCAGCAT GGTGACCAGC

901 GAGAGCCAGC TGTTCAACAA GCCCTACTGG CTGCAGAGGG CCCAGGGCCA CAACAACGGC

961 ATCTGCTGGG GCAACCAGCT GTTCGTGACC GTGGTGGACA CCACCAGGAG CACCAACATG

1021 ACCCTGTGCG CCGAGGTGAA GAAGGAGAGC ACCTACAAGA ACGAGAACTT CAAGGAGTAC

1081 CTGAGGCACG GCGAGGAGTT CGACCTGCAG TTCATCTTCC AGCTGTGCAA GATCACCCTG

1141 ACCGCCGACG TGATGACCTA CATCCACAAG ATGGACGCCA CCATCCTGGA GGACTGGCAG

1201 TTCGGCCTGA CCCCCCCCCC CAGCGCCAGC CTGGAGGACA CCTACAGGTT CGTGACCAGC

1261 ACCGCCATCA CCTGCCAGAA GAACACCCCC CCCAAGGGCA AGGAGGACCC CCTGAAGGAC

1321 TACATGTTCT GGGAGGTGGA CCTGAAGGAG AAGTTCAGCG CCGACCTGGA CCAGTTCCCC

1381 CTGGGCAGGA AGTTCCTGCT GCAGGCCGGC CTGCAGGCCA GGCCCAAGCT GAAGAGGCCC

1441 GCCAGCAGCG CCCCCAGGAC CAGCACCAAG AAGAAGAAGG TGAAGAGGTG A
```

Sequence 20 (SEQ ID NO: 20):
```
   1 ATGACCGTGT ACCTGCCCCC CGTGCCCGTG AGCAAGGTGG TGAGCACCGA CGAGTACGTG

61 AGCAGGACCA GCATCTACTA CTACGCCGGC AGCAGCAGGC TGCTGACCGT GGGCCACCCC

121 TACTTCAGCA TCAAGAACAC CAGCAGCGGC AACGGCAAGA AGGTGCTGGT GCCCAAGGTG

181 AGCGGCCTGC AGTACAGGGT GTTCAGGATC AAGCTGCCCG ACCCCAACAA GTTCGGCTTC

241 CCCGACACCA GCTTCTACAA CCCCGAGACC CAGAGGCTGG TGTGGGCCTG CACCGGCCTG

301 GAGATCGCGG GGGCCAGCC CCTGGGCGTG GGCATCAGCG GCCACCCCCT GCTGAACAAG

361 TTCGACGACA CCGAGACCAG CAACAAGTAC GCCGGCAAGC CCGGCATCGA CAACAGGGAG
```

-continued

```
 421 TGCCTGAGCA TGGACTACAA GCAGACCCAG CTGTGCATCC TGGGCTGCAA GCCCCCCATC
 481 GGCGAGCACT GGGGCAAGGG CACCCCCTGC AACAACAACA GCGGCAACCC CGGCGACTGC
 541 CCCCCCCTGC AGCTGATCAA CAGCGTGATC CAGGACGGCG ACATGGTGGA CACCGGCTTC
 601 GGCTGCATGG ACTTCAACAC CCTGCAGGCC AGCAAGAGCG ACGTGCCCAT CGACATCTGC
 661 AGCAGCGTGT GCAAGTACCC CGACTACCTG CAGATGGCCA GCGAGCCCTA CGGCGACAGC
 721 CTGTTCTTCT TCCTGAGGAG GGAGCAGATG TTCGTGAGGC ACTTCTTCAA CAGGGCCGGC
 781 ACCCTGGGCG ACCCCGTGCC CGGCGACCTG TACATCCAGG GCAGCAACAG CGGCAACACC
 841 GCCACCGTGC AGAGCAGCGC CTTCTTCCCC ACCCCCAGCG GCAGCATGGT GACCAGCGAG
 901 AGCCAGCTGT TCAACAAGCC CTACTGGCTG CAGAGGGCCC AGGGCCACAA CAACGGCATC
 961 TGCTGGGGCA ACCAGCTGTT CGTGACCGTG GTGGACACCA CCAGGAGCAC CAACATGACC
1021 CTGTGCGCCG AGGTGAAGAA GGAGAGCACC TACAAGAACG AGAACTTCAA GGAGTACCTG
1081 AGGCACGGCG AGGAGTTCGA CCTGCAGTTC ATCTTCCAGC TGTGCAAGAT CACCCTGACC
1141 GCCGACGTGA TGACCTACAT CCACAAGATG GACGCCACCA TCCTGGAGGA CTGGCAGTTC
1201 GGCCTGACCC CCCCCCCCAG CGCCAGCCTG GAGGACACCT ACAGGTTCGT GACCAGCACC
1261 GCCATCACCT GCCAGAAGAA CACCCCCCCC AAGGGCAAGG AGGACCCCCT GAAGGACTAC
1321 ATGTTCTGGG AGGTGGACCT GAAGGAGAAG TTCAGCGCCG ACCTGGACCA GTTCCCCCTG
1381 GGCAGGAAGT TCCTGCTGCA GGCCGGCCTG CAGGCCAGGC CCAAGCTGAA GAGGCCCGCC
1441 AGCAGCGCCC CCAGGACCAG CACCAAGAAG AAGAAGGTGA GAGGTGA
```

Sequence 21 (SEQ ID NO: 21):
```
   1 ATGGTGTACC TGCCCCCCGT GCCCGTGAGC AAGGTGGTGA GCACCGACGA GTACGTGAGC
  61 AGGACCAGCA TCTACTACTA CGCCGGCAGC AGCAGGCTGC TGACCGTGGG CCACCCCTAC
 121 TTCAGCATCA AGAACACCAG CAGCGGCAAC GGCAAGAAGG TGCTGGTGCC CAAGGTGAGC
 181 GGCCTGCAGT ACAGGGTGTT CAGGATCAAG CTGCCCGACC CCAACAAGTT CGGCTTCCCC
 241 GACACCAGCT TCTACAACCC CGAGACCCAG AGGCTGGTGT GGGCCTGCAC CGGCCTGGAG
 301 ATCGGCAGGG GCCAGCCCCT GGGCGTGGGC ATCAGCGGCC ACCCCCTGCT GAACAAGTTC
 361 GACGACACCG AGACCAGCAA CAAGTACGCC GGCAAGCCCG GCATCGACAA CAGGGAGTGC
 421 CTGAGCATGG ACTACAAGCA GACCCAGCTG TGCATCCTGG GCTGCAAGCC CCCCATCGGC
 481 GAGCACTGGG GCAAGGGCAC CCCCTGCAAC AACAACAGCG GCAACCCCGG CGACTGCCCC
 541 CCCCTGCAGC TGATCAACAG CGTGATCCAG GACGGCGACA TGGTGGACAC CGGCTTCGGC
 601 TGCATGGACT TCAACACCCT GCAGGCCAGC AAGAGCGACG TGCCCATCGA CATCTGCAGC
 661 AGCGTGTGCA AGTACCCCGA CTACCTGCAG ATGGCCAGCG AGCCCTACGG CGACAGCCTG
 721 TTCTTCTTCC TGAGGAGGGA GCAGATGTTC GTGAGGCACT TCTTCAACAG GGCCGGCACC
 781 CTGGGCGACC CCGTGCCCGG CGACCTGTAC ATCCAGGGCA GCAACAGCGG CAACACCGCC
 841 ACCGTGCAGA GCAGCGCCTT CTTCCCCACC CCCAGCGGCA GCATGGTGAC CAGCGAGAGC
 901 CAGCTGTTCA ACAAGCCCTA CTGGCTGCAG AGGGCCCAGG GCCACAACAA CGGCATCTGC
 961 TGGGCAACC AGCTGTTCGT GACCGTGGTG GACACCACCA GGAGCACCAA CATGACCCTG
1021 TGCGCCGAGG TGAAGAAGGA GAGCACCTAC AAGAACGAGA ACTTCAAGGA GTACCTGAGG
1081 CACGGCGAGG AGTTCGACCT GCAGTTCATC TTCCAGCTGT GCAAGATCAC CCTGACCGCC
1141 GACGTGATGA CCTACATCCA CAAGATGGAC GCCACCATCC TGGAGGACTG GCAGTTCGGC
1201 CTGACCCCCC CCCCAGCGC CAGCCTGGAG GACACCTACA GGTTCGTGAC CAGCACCGCC
1261 ATCACCTGCC AGAAGAACAC CCCCCCCAAG GGCAAGGAGG ACCCCCTGAA GGACTACATG
```

```
1321 TTCTGGGAGG TGGACCTGAA GGAGAAGTTC AGCGCCGACC TGGACCAGTT CCCCCTGGGC

1381 AGGAAGTTCC TGCTGCAGGC CGGCCTGCAG GCCAGGCCCA AGCTGAAGAG GCCCGCCAGC

1441 AGCGCCCCCA GGACCAGCAC CAAGAAGAAG AAGGTGAAGA GGTGA
```
Sequence 22 (SEQ ID NO: 22):
```
   1 ATGTACCTGC CCCCCGTGCC CGTGAGCAAG GTGGTGAGCA CCGACGAGTA CGTGAGCAGG

61 ACCAGCATCT ACTACTACGC CGGCAGCAGC AGGCTGCTGA CCGTGGGCCA CCCCTACTTC

121 AGCATCAAGA ACACCAGCAG CGGCAACGGC AAGAAGGTGC TGGTGCCCAA GGTGAGCGGC

181 CTGCAGTACA GGGTGTTCAG GATCAAGCTG CCCGACCCCA CAAGTTCGG CTTCCCCGAC

241 ACCAGCTTCT ACAACCCCGA GACCCAGAGG CTGGTGTGGG CCTGCACCGG CCTGGAGATC

301 GGCAGGGGCC AGCCCCTGGG CGTGGGCATC AGCGGCCACC CCCTGCTGAA CAAGTTCGAC

361 GACACCGAGA CCAGCAACAA GTACGCCGGC AAGCCCGGCA TCGACAACAG GGAGTGCCTG

421 AGCATGGACT ACAAGCAGAC CCAGCTGTGC ATCCTGGGCT GCAAGCCCCC CATCGGCGAG

481 CACTGGGGCA AGGGCACCCC CTGCAACAAC AACAGCGGCA ACCCCGGCGA CTGCCCCCCC

541 CTGCAGCTGA TCAACAGCGT GATCCAGGAC GGCGACATGG TGGACACCGG CTTCGGCTGC

601 ATGGACTTCA ACACCCTGCA GGCCAGCAAG AGCGACGTGC CCATCGACAT CTGCAGCAGC

661 GTGTGCAAGT ACCCCGACTA CCTGCAGATG GCCAGCGAGC CCTACGGCGA CAGCCTGTTC

721 TTCTTCCTGA GGAGGGAGCA GATGTTCGTG AGGCACTTCT TCAACAGGGC CGGCACCCTG

781 GGCGACCCCG TGCCCGGCGA CCTGTACATC CAGGGCAGCA ACAGCGGCAA CACCGCCACC

841 GTGCAGAGCA GCGCCTTCTT CCCCACCCCC AGCGGCAGCA TGGTGACCAG CGAGAGCCAG

901 CTGTTCAACA AGCCCTACTG GCTGCAGAGG GCCCAGGGCC ACAACAACGG CATCTGCTGG

961 GGCAACCAGC TGTTCGTGAC CGTGGTGGAC ACCACCAGGA GCACCAACAT GACCCTGTGC

1021 GCCGAGGTGA AGAAGGAGAG CACCTACAAG AACGAGAACT TCAAGGAGTA CCTGAGGCAC

1081 GGCGAGGAGT TCGACCTGCA GTTCATCTTC CAGCTGTGCA AGATCACCCT GACCGCCGAC

1141 GTGATGACCT ACATCCACAA GATGGACGCC ACCATCCTGG AGGACTGGCA GTTCGGCCTG

1201 ACCCCCCCCC CCAGCGCCAG CCTGGAGGAC ACCTACAGGT TCGTGACCAG CACCGCCATC

1261 ACCTGCCAGA GAACACCCCC CCCCAAGGGC AAGGAGGACC CCTGAAGGA CTACATGTTC

1321 TGGGAGGTGG ACCTGAAGGA GAAGTTCAGC GCCGACCTGG ACCAGTTCCC CCTGGGCAGG

1381 AAGTTCCTGC TGCAGGCCGG CCTGCAGGCC AGGCCCAAGC TGAAGAGGCC CGCCAGCAGC

1441 GCCCCCAGGA CCAGCACCAA GAAGAAGAAG GTGAAGAGGT GA
```
Sequence 23 (SEQ ID NO: 23):
```
   1 ATGCTGCCCC CCGTGCCCGT GAGCAAGGTG GTGAGCACCG ACGAGTACGT GAGCAGGACC

61 AGCATCTACT ACTACGCCGG CAGCAGCAGG CTGCTGACCG TGGGCCACCC CTACTTCAGC

121 ATCAAGAACA CCAGCAGCGG CAACGGCAAG AAGGTGCTGG TGCCCAAGGT GAGCGGCCTG

181 CAGTACAGGG TGTTCAGGAT CAAGCTGCCC GACCCCAACA AGTTCGGCTT CCCCGACACC

241 AGCTTCTACA ACCCCGAGAC CCAGAGGCTG GTGTGGGCCT GCACCGGCCT GGAGATCGGC

301 AGGGGCCAGC CCCTGGGCGT GGGCATCAGC GGCCACCCCC TGCTGAACAA GTTCGACGAC

361 ACCGAGACCA GCAACAAGTA CGCCGGCAAG CCCGGCATCG ACAACAGGGA GTGCCTGAGC

421 ATGGACTACA AGCAGACCCA GCTGTGCATC CTGGGCTGCA AGCCCCCCAT CGGCGAGCAC

481 TGGGGCAAGG GCACCCCCTG CAACAACAAC AGCGGCAACC CCGGCGACTG CCCCCCCCTG

541 CAGCTGATCA ACAGCGTGAT CCAGGACGGC GACATGGTGG ACACCGGCTT CGGCTGCATG

601 GACTTCAACA CCCTGCAGGC CAGCAAGAGC GACGTGCCCA TCGACATCTG CAGCAGCGTG
```

-continued

```
 661 TGCAAGTACC CCGACTACCT GCAGATGGCC AGCGAGCCCT ACGGCGACAG CCTGTTCTTC
 721 TTCCTGAGGA GGGAGCAGAT GTTCGTGAGG CACTTCTTCA ACAGGGCCGG CACCCTGGGC
 781 GACCCCGTGC CCGGCGACCT GTACATCCAG GGCAGCAACA GCGGCAACAC CGCCACCGTG
 841 CAGAGCAGCG CCTTCTTCCC CACCCCCAGC GGCAGCATGG TGACCAGCGA GAGCCAGCTG
 901 TTCAACAAGC CCTACTGGCT GCAGAGGGCC CAGGGCCACA ACAACGGCAT CTGCTGGGGC
 961 AACCAGCTGT TCGTGACCGT GGTGGACACC ACCAGGAGCA CCAACATGAC CCTGTGCGCC
1021 GAGGTGAAGA AGGAGAGCAC CTACAAGAAC GAGAACTTCA AGGAGTACCT GAGGCACGGC
1081 GAGGAGTTCG ACCTGCAGTT CATCTTCCAG CTGTGCAAGA TCACCCTGAC CGCCGACGTG
1141 ATGACCTACA TCCACAAGAT GGACGCCACC ATCCTGGAGG ACTGGCAGTT CGGCCTGACC
1201 CCCCCCCCCA GCGCCAGCCT GGAGGACACC TACAGGTTCG TGACCAGCAC CGCCATCACC
1261 TGCCAGAAGA ACACCCCCCC CAAGGGCAAG GAGGACCCCC TGAAGGACTA CATGTTCTGG
1321 GAGGTGGACC TGAAGGAGAA GTTCAGCGCC GACCTGGACC AGTTCCCCCT GGGCAGGAAG
1381 TTCCTGCTGC AGGCCGGCCT GCAGGCCAGG CCCAAGCTGA GAGGCCCGC CAGCAGCGCC
1441 CCCAGGACCA GCACCAAGAA GAAGAAGGTG AAGAGGTGA
```

Sequence 24 (SEQ ID NO: 24):
```
   1 ATGCCCCCCG TGCCCGTGAG CAAGGTGGTG AGCACCGACG AGTACGTGAG CAGGACCAGC
  61 ATCTACTACT ACGCCGGCAG CAGCAGGCTG CTGACCGTGG CCACCCCCTA CTTCAGCATC
 121 AAGAACACCA GCAGCGGCAA CGGCAAGAAG GTGCTGGTGC CAAGGTGAG CGGCCTGCAG
 181 TACAGGGTGT TCAGGATCAA GCTGCCCGAC CCCAACAAGT TCGGCTTCCC CGACACCAGC
 241 TTCTACAACC CCGAGACCCA GAGGCTGGTG TGGGCCTGCA CCGGCCTGGA GATCGGCAGG
 301 GGCCAGCCCC TGGGCGTGGG CATCAGCGGC CACCCCCTGC TGAACAAGTT CGACGACACC
 361 GAGACCAGCA ACAAGTACGC CGGCAAGCCC GGCATCGACA CAGGGAGTG CCTGAGCATG
 421 GACTACAAGC AGACCCAGCT GTGCATCCTG GGCTGCAAGC CCCCCATCGG CGAGCACTGG
 481 GGCAAGGGCA CCCCCTGCAA CAACAACAGC GGCAACCCCG CGACTGCCC CCCCCTGCAG
 541 CTGATCAACA GCGTGATCCA GGACGGCGAC ATGGTGGACA CCGGCTTCGG CTGCATGGAC
 601 TTCAACACCC TGCAGGCCAG CAAGAGCGAC GTGCCCATCG ACATCTGCAG CAGCGTGTGC
 661 AAGTACCCCG ACTACCTGCA GATGGCCAGC GAGCCCTACG CGACAGCCT GTTCTTCTTC
 721 CTGAGGAGGG AGCAGATGTT CGTGAGGCAC TTCTTCAACA GGGCCGGCAC CCTGGGCGAC
 781 CCCGTGCCCG GCGACCTGTA CATCCAGGGC AGCAACAGCG GCAACACCGC CACCGTGCAG
 841 AGCAGCGCCT TCTTCCCCAC CCCCAGCGGC AGCATGGTGA CCAGCGAGAG CCAGCTGTTC
 901 AACAAGCCCT ACTGGCTGCA GAGGGCCCAG GCCACAACA ACGGCATCTG CTGGGGCAAC
 961 CAGCTGTTCG TGACCGTGGT GGACACCACC AGGAGCACCA ACATGACCCT GTGCGCCGAG
1021 GTGAAGAAGG AGAGCACCTA CAAGAACGAG AACTTCAAGG AGTACCTGAG GCACGGCGAG
1081 GAGTTCGACC TGCAGTTCAT CTTCCAGCTG TGCAAGATCA CCCTGACCGC CGACGTGATG
1141 ACCTACATCC ACAAGATGGA CGCCACCATC CTGGAGGACT GGCAGTTCGG CCTGACCCCC
1201 CCCCCCAGCG CCAGCCTGGA GGACACCTAC AGGTTCGTGA CCAGCACCGC CATCACCTGC
1261 CAGAAGAACA CCCCCCCCAA GGGCAAGGAG GACCCCCTGA AGGACTACAT GTTCTGGGAG
1321 GTGGACCTGA AGGAGAAGTT CAGCGCCGAC CTGGACCAGT TCCCCCTGGG CAGGAAGTTC
1381 CTGCTGCAGG CCGGCCTGCA GGCCAGGCCC AAGCTGAAGA GGCCCGCCAG CAGCGCCCCC
1441 AGGACCAGCA CCAAGAAGAA GAAGGTGAAG AGGTGA
```

Sequence 25 (SEQ ID NO: 25):
```
   1 ATGCCCGTGC CCGTGAGCAA GGTGGTGAGC ACCGACGAGT ACGTGAGCAG GACCAGCATC
  61 TACTACTACG CCGGCAGCAG CAGGCTGCTG ACCGTGGGCC ACCCCTACTT CAGCATCAAG
 121 AACACCAGCA GCGGCAACGG CAAGAAGGTG CTGGTGCCCA AGGTGAGCGG CCTGCAGTAC
 181 AGGGTGTTCA GGATCAAGCT GCCCGACCCC AACAAGTTCG GCTTCCCCGA CACCAGCTTC
 241 TACAACCCCG AGACCCAGAG GCTGGTGTGG GCCTGCACCG GCCTGGAGAT CGGCAGGGGC
 301 CAGCCCCTGG GCGTGGGCAT CAGCGGCCAC CCCCTGCTGA ACAAGTTCGA CGACACCGAG
 361 ACCAGCAACA AGTACGCCGG CAAGCCCGGC ATCGACAACA GGGAGTGCCT GAGCATGGAC
 421 TACAAGCAGA CCCAGCTGTG CATCCTGGGC TGCAAGCCCC CCATCGGCGA GCACTGGGGC
 481 AAGGGCACCC CCTGCAACAA CAACAGCGGC AACCCCGGCG ACTGCCCCCC CCTGCAGCTG
 541 ATCAACAGCG TGATCCAGGA CGGCGACATG GTGGACACCG GCTTCGGCTG CATGGACTTC
 601 AACACCCTGC AGGCCAGCAA GAGCGACGTG CCCATCGACA TCTGCAGCAG CGTGTGCAAG
 661 TACCCCGACT ACCTGCAGAT GGCCAGCGAG CCCTACGGCG ACAGCCTGTT CTTCTTCCTG
 721 AGGAGGGAGC AGATGTTCGT GAGGCACTTC TTCAACAGGG CCGGCACCCT GGGCGACCCC
 781 GTGCCCGGCG ACCTGTACAT CCAGGGCAGC AACAGCGGCA ACACCGCCAC CGTGCAGAGC
 841 AGCGCCTTCT TCCCCACCCC CAGCGGCAGC ATGGTGACCA GCGAGAGCCA GCTGTTCAAC
 901 AAGCCCTACT GGCTGCAGAG GGCCCAGGGC ACAACAACG GCATCTGCTG GGGCAACCAG
 961 CTGTTCGTGA CCGTGGTGGA CACCACCAGG AGCACCAACA TGACCCTGTG CGCCGAGGTG
1021 AAGAAGGAGA GCACCTACAA GAACGAGAAC TTCAAGGAGT ACCTGAGGCA CGGCGAGGAG
1081 TTCGACCTGC AGTTCATCTT CCAGCTGTGC AAGATCACCC TGACCGCCGA CGTGATGACC
1141 TACATCCACA AGATGGACGC CACCATCCTG GAGGACTGGC AGTTCGGCCT GACCCCCCCC
1201 CCCAGCGCCA GCCTGGAGGA CACCTACAGG TTCGTGACCA GCACCGCCAT CACCTGCCAG
1261 AAGAACACCC CCCCCAAGGG CAAGGAGGAC CCCCTGAAGG ACTACATGTT CTGGGAGGTG
1321 GACCTGAAGG AGAAGTTCAG CGCCGACCTG GACCAGTTCC CCTGGGCAG GAAGTTCCTG
1381 CTGCAGGCCG GCCTGCAGGC CAGGCCCAAG CTGAAGAGGC CGCCAGCAG CGCCCCCAGG
1441 ACCAGCACCA AGAAGAAGAA GGTGAAGAGG TGA
```
Sequence 26 (SEQ ID NO: 26):
```
   1 ATGCCCGTGA GCAAGGTGGT GAGCACCGAC GAGTACGTGA GCAGGACCAG CATCTACTAC
  61 TACGCCGGCA GCAGCAGGCT GCTGACCGTG GGCCACCCCT ACTTCAGCAT CAAGAACACC
 121 AGCAGCGGCA ACGGCAAGAA GGTGCTGGTG CCCAAGGTGA GCGGCCTGCA GTACAGGGTG
 181 TTCAGGATCA AGCTGCCCGA CCCCAACAAG TTCGGCTTCC CCGACACCAG CTTCTACAAC
 241 CCCGAGACCC AGAGGCTGGT GTGGGCCTGC ACCGGCCTGG AGATCGGCAG GGGCCAGCCC
 301 CTGGGCGTGG GCATCAGCGG CCACCCCCTG CTGAACAAGT TCGACGACAC CGAGACCAGC
 361 AACAAGTACG CCGGCAAGCC CGGCATCGAC AACAGGGAGT GCCTGAGCAT GGACTACAAG
 421 CAGACCCAGC TGTGCATCCT GGGCTGCAAG CCCCCCATCG GCGAGCACTG GGGCAAGGGC
 481 ACCCCCTGCA ACAACAACAG CGGCAACCCC GGCGACTGCC CCCCCCTGCA GCTGATCAAC
 541 AGCGTGATCC AGGACGGCGA CATGGTGGAC ACCGGCTTCG GCTGCATGGA CTTCAACACC
 601 CTGCAGGCCA GCAAGAGCGA CGTGCCCATC GACATCTGCA GCAGCGTGTG CAAGTACCCC
 661 GACTACCTGC AGATGGCCAG CGAGCCCTAC GGCGACAGCC TGTTCTTCTT CCTGAGGAGG
 721 GAGCAGATGT TCGTGAGGCA CTTCTTCAAC AGGGCCGGCA CCCTGGGCGA CCCCGTGCCC
 781 GGCGACCTGT ACATCCAGGG CAGCAACAGC GGCAACACCG CCACCGTGCA GAGCAGCGCC
 841 TTCTTCCCCA CCCCCAGCGG CAGCATGGTG ACCAGCGAGA GCCAGCTGTT CAACAAGCCC
```

```
 901 TACTGGCTGC AGAGGGCCCA GGGCCACAAC AACGGCATCT GCTGGGGCAA CCAGCTGTTC

961 GTGACCGTGG TGGACACCAC CAGGAGCACC AACATGACCC TGTGCGCCGA GGTGAAGAAG

1021 GAGAGCACCT ACAAGAACGA GAACTTCAAG GAGTACCTGA GGCACGGCGA GGAGTTCGAC

1081 CTGCAGTTCA TCTTCCAGCT GTGCAAGATC ACCCTGACCG CCGACGTGAT GACCTACATC

1141 CACAAGATGG ACGCCACCAT CCTGGAGGAC TGGCAGTTCG GCCTGACCCC CCCCCCCAGC

1201 GCCAGCCTGG AGGACACCTA CAGGTTCGTG ACCAGCACCG CCATCACCTG CCAGAAGAAC

1261 ACCCCCCCCA AGGGCAAGGA GGACCCCCTG AAGGACTACA TGTTCTGGGA GGTGGACCTG

1321 AAGGAGAAGT TCAGCGCCGA CCTGGACCAG TTCCCCCTGG GCAGGAAGTT CCTGCTGCAG

1381 GCCGGCCTGC AGGCCAGGCC CAAGCTGAAG AGGCCCGCCA GCAGCGCCCC CAGGACCAGC

1441 ACCAAGAAGA AGAAGGTGAA GAGGTGA
```

Sequence 27 (SEQ ID NO: 27):
```
  1 MVQILFYILV IFYYVAGVNV FHIFLQMSVW RPSEATVYLP PVPVSKVVST DEYVSRTSIY

61 YYAGSSRLLT VGHPYFSIKN TSSGNGKKVL VPKVSGLQYR VFRIKLPDPN KFGFPDTSFY

121 NPETQRLVWA CTGLEIGRGQ PLGVGISGHP LLNKFDDTET SNKYAGKPGI DNRECLSMDY

181 KQTQLCILGC KPPIGEHWGK GTPCNNNSGN PGDCPPLQLI NSVIQDGDMV DTGFGCMDFN

241 TSQASKSDVP IDICSSVCKY PDYLQMASEP YGDSLFFFLR REQMFVRHFF NRAGTLGDPV

301 PGDLYIQGSN SGNTATVQSS AFFPTPSGSM VTSESQLFNK PYWLQRAQGH NNGICWGNQL

361 FVTVVDTTRS TNMTLCAEVK KESTYKNENF KEYLRHGEEF DLQFIFQLCK ITLTADVMTY

421 IHKMDATILE DWQFGLTPPP SASLEDTYRF VTSTAITCQK NTPPKGKEDP LKDYMFWEVD

481 LKEKFSADLD QFPLGRKFLL QAGLQARPKL KRPASSAPRT STKKKKVKR
```

Sequence 28 (SEQ ID NO: 28):
```
  1 MVQILFYILV IFYYVAGVNV FHIFLQMSVW RPSEATVYLP PVPVSKVVST DEYVSRTSIY

61 YYAGSSRLLT VGHPYFSIKN TSSGNGKKVL VPKVSGLQYR VFRIKLPDPN KFGFPDTSFY

121 NPETQRLVWA CTGLEIGRGQ PLGVGISGHP LLNKFDDTET SNKYAGKPGI DNRECLSMDY

181 KQTQLCILGC KPPIGEHWGK GTPCNNNSGN PGDCPPLQLI NSVIQDGDMV DTGFGCMDFN

241 TLQASKSDVP IDICSSVCKY PDYLQMASEP YGDSLFFFLR REQMFVRHFF NRAGTLGDPV

301 PGDLYIQGSN SGNTATVQSS AFFPTPSGSM VTSESQLFNK PYWLQRAQGH NNGICWGNQL

361 FVTVVDTTRS TNMTLCAEVK KESTYKNENF KEYLRHGEEF DLQFIFQLCK ITLTADVMTY

421 IHKMDATILE DWQFGLTPPP SASLEDTYRF VTSTAITCQK NTPPKGKEDP LKDYMFWEVD

481 LKEKFSADLD QFPLGRKFLL QAGLQARPKL KRPASSAPRT STKKKKVKR
```

Sequence 29 (SEQ ID NO: 29):
```
  1 MVQILFYILV IFYYVAGVNV FHIFLQMSVW RPSVATVYLP PVPVSKVVST DEYVSRTSIY

61 YYAGSSRLLT VGHPYFSIKN TSSGNGKKVL VPKVSGLQYR VFRIKLPDPN KFGFPDTSFY

121 NPETQRLVWA CTGLEIGRGQ PLGVGISGHP LLNKFDDTET SNKYAGKPGI DNRECLSMDY

181 KQTQLCILGC KPPIGEHWGK GTPCNNNSGN PGDCPPLQLI NSVIQDGDMV DTGFGCMDFN

241 TLQASKSDVP IDICSSVCKY PDYLQMASEP YGDSLFFFLR REQMFVRHFF NRAGTLGDPV

301 PGDLYIQGSN SGNTATVQSS AFFPTPSGSM VTSESQLFNK PYWLQRAQGH NNGICWGNQL

361 FVTVVDTTRS TNMTLCAEVK KESTYKNENF KEYLRHGEEF DLQFIFQLCK ITLAADVMTY

421 IHKMDATILE DWQFGLTPPP SASLEDTYRF VTSTAITCQK NTPPKGKEDP LKDYMFWEVD

481 LKEKFSADLD QFPLGRKFLL QAGLQARPKL KRPASSAPRT STKKKKVKR
```

-continued

Sequence 30 (SEQ ID NO: 30):

```
   1 ATGGTGCAGA TCCTGTTCTA CATCCTGGTG ATCTTCTACT ACGTGGCCGG CGTGAACGTG

61 TTCCACATCT TCCTGCAGAT GAGCGTGTGG AGGCCCAGCG AGGCCACCGT GTACCTGCCC

121 CCCGTGCCCG TGAGCAAGGT GGTGAGCACC GACGAGTACG TGAGCAGGAC CAGCATCTAC

181 TACTACGCCG GCAGCAGCAG GCTGCTGACC GTGGGCCACC CCTACTTCAG CATCAAGAAC

241 ACCAGCAGCG GCAACGGCAA GAAGGTGCTG GTGCCCAAGG TGAGCGGCCT GCAGTACAGG

301 GTGTTCAGGA TCAAGCTGCC CGACCCCAAC AAGTTCGGCT TCCCCGACAC CAGCTTCTAC

361 AACCCCGAGA CCCAGAGGCT GGTGTGGGCC TGCACCGGCC TGGAGATCGG CAGGGGCCAG

421 CCCCTGGGCG TGGGCATCAG CGGCCACCCC CTGCTGAACA AGTTCGACGA CACCGAGACC

481 AGCAACAAGT ACGCCGGCAA GCCCGGCATC GACAACAGGG AGTGCCTGAG CATGGACTAC

541 AAGCAGACCC AGCTGTGCAT CCTGGGCTGC AAGCCCCCCA TCGGCGAGCA CTGGGGCAAG

601 GGCACCCCCT GCAACAACAA CAGCGGCAAC CCCGGCGACT GCCCCCCCCT GCAGCTGATC

661 AACAGCGTGA TCCAGGACGG CGACATGGTG GACACCGGCT TCGGCTGCAT GGACTTCAAC

721 ACCCTGCAGG CCAGCAAGAG CGACGTGCCC ATCGACATCT GCAGCAGCGT GTGCAAGTAC

781 CCCGACTACC TGCAGATGGC CAGCGAGCCC TACGGCGACA GCCTGTTCTT CTTCCTGAGG

841 AGGGAGCAGA TGTTCGTGAG GCACTTCTTC AACAGGGCCG GCACCCTGGG CGACCCCGTG

901 CCCGGCGACC TGTACATCCA GGGCAGCAAC AGCGGCAACA CCGCCACCGT GCAGAGCAGC

961 GCCTTCTTCC CCACCCCCAG CGGCAGCATG GTGACCAGCG AGAGCCAGCT GTTCAACAAG

1021 CCCTACTGGC TGCAGAGGGC CCAGGGCCAC AACAACGGCA TCTGCTGGGG CAACCAGCTG

1081 TTCGTGACCG TGGTGGACAC CACCAGGAGC ACCAACATGA CCCTGTGCGC CGAGGTGAAG

1141 AAGGAGAGCA CCTACAAGAA CGAGAACTTC AAGGAGTACC TGAGGCACGG CGAGGAGTTC

1201 GACCTGCAGT TCATCTTCCA GCTGTGCAAG ATCACCCTGA CCGCCGACGT GATGACCTAC

1261 ATCCACAAGA TGGACGCCAC CATCCTGGAG GACTGGCAGT TCGGCCTGAC CCCCCCCCCC

1321 AGCGCCAGCC TGGAGGACAC CTACAGGTTC GTGACCAGCA CCGCCATCAC CTGCCAGAAG

1381 AACACCCCCC CCAAGGGCAA GGAGGACCCC CTGAAGGACT ACATGTTCTG GGAGGTGGAC

1441 CTGAAGGAGA AGTTCAGCGC CGACCTGGAC CAGTTCCCCC TGGGCAGGAA GTTCCTGCTG

1501 CAGGCCGGCC TGCAGGCCAG GCCCAAGCTG AAGAGGCCCG CCAGCAGCGC CCCCAGGACC

1561 AGCACCAAGA AGAAGAAGGT GAAGAGGTGA
```

SPECIFIC MODES FOR CARRYING OUT THE INVENTION

The present invention is further illustrated in detail by reference to the examples as follows. It is understood by those skilled in the art that the examples are used only for the purpose of illustrating the present invention, rather than limiting the protection scope of the present invention.

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995, or in accordance with the product instructions. The reagents and instruments used in the present invention without marking out their manufacturers are all conventional products commercially available from markets. Those skilled in the art understand that the examples are used for illustrating the present invention, but not intended to limit the protection scope of the present invention.

Example 1

Construction of Non-Fusion Expression Vectors for Expressing the Truncated HPV52 L1 Proteins The full-length HPV52 L1 Gene (SEQ ID NO: 30) as a template was synthesized by Shanghai Boya Bio Co. The synthesized gene fragment has a full length of 1590 bp. On the basis of the synthetic full-length HPV52 L1 gene fragment, the polynucleotides encoding the truncated HPV52 L1 proteins according to the invention were prepared.

The synthesized full-length HPV52 L1 gene was used as the template for the PCR reaction. The forward primer was 52N40F: 5'-CAT ATg CCC GTG CCC GTG AGC AAG-3' (SEQ ID NO: 31), at the 5' terminal of which the restriction endonuclease NdeI site CAT ATG was introduced, wherein ATG was the initiation codon in *E. coli* system. The reverse primer was 52CR: 5'-GTC GAC TCA CCT CTT CAC CTT CTT C-3' (SEQ ID NO: 32), at the 5' terminal of which the restriction endonuclease SalI site was introduced. The PCR reaction was performed in a PCR thermocycler (Biometra T3) under the following conditions:

| | |
|---|---|
| 94 denaturation 10 min | 1 cycle |
| 94 denaturation 50 sec | 15 cycles |
| 56 annealing 50 sec | |
| 72 elongation 1.5 min | |
| 72 elongation 10 min | 1 cycle |

The DNA fragments, about 1.5 kb in length, were obtained after amplification. The PCR products were linked into the commercially available pMD 18-T vector (Takara Biosciences), and were transformed into *E. coli*. Positive bacterial colonies were screened, and plasmids were extracted. After digestion with NdeI/SalI, it was identified that positive clones, designated as pMD 18-T-HPV52N40C-L1, were obtained, wherein the truncated HPV52 L1 gene was inserted.

The nucleotide sequence of the fragment of interest, which was inserted into the plasmid pMD 18-T-HPV52N40C-L1, was determined as SEQ ID NO: 25 by Shanghai Boya Bio Co. using M13 (+)/(−) primers, and the amino acid sequence encoded thereby was set forth in SEQ ID NO: 12. The sequence corresponded to a HPV52 L1 protein having 40 amino acids truncated at its N-terminal and no amino acid truncated at its C-terminal, designated as HPV52N40C-L1.

The HPV52N40C-L1 gene fragment was obtained by NdeI/SalI digestion of plasmid pMD 18-T-HPV52N40C-L1. The fragment was linked into the prokaryotic expression vector pT0-T7 (purchased from Invitrogen) digested with NdeI/SalI, and was transformed into ER2566 bacteria. Positive bacterial colonies were screened, and plasmids were extracted. After digestion with NdeI/SalI, it was identified that positive clones, designated as pT0-T7-HPV52N40C-L1, were obtained, wherein the fragment of interest was inserted.

1 µL plasmid pT0-T7-HPV52N40C-L1 (0.15 mg/ml) was used to transform 40 µL competent *E. coli* ER2566 (purchased from Invitrogen) prepared by the Calcium chloride method, and then the bacteria were plated on solid LB medium (the components of the LB medium: 10 g/L peptone, 5 g/L yeast powder, and 10 g/L NaCl, the same as below) containing kanamycin (at a final concentration of 100 mg/ml, the same as below). The plates were statically incubated at 37° C. for about 10-12 h until single colonies could be observed clearly. Single colonies from the plates were transferred to a tube containing 4 ml liquid LB media containing kanamycin. The cultures were incubated in a shaking incubator at 180 rpm for 10 h at 37° C., and then 1 ml bacterial solution was taken and stored at −70° C.

Example 2

Expression of HPV52N40C-L1 Protein on a Large Scale

The *E. coli* solution carrying the recombinant plasmid pTO-T7-HPV52N40C-L1 at −70° C. as prepared in Example 1 was seeded in 50 mL LB liquid medium containing kanamycin and incubated at 180 rpm and 37° C. for about 12 h. Then, the cultures were transferred to ten flasks (5 ml cultures per flask), each of which contained 500 mL LB medium containing kanamycin, and was incubated in a shaking incubator overnight at 180 rpm and 37° C., as a starter culture.

A 50 L fermenter made by Shanghai Baoxing Biological Ltd was used in large-scale culture. PH electrode of the fermenter was calibrated. 30 L LB medium was loaded into the fermenter, in situ sterilized at 121° C. for 30 minutes. Oxygen-dissolved electrode was calibrated, wherein the value was determined as 0 prior to introduction of air after sterilization and as 100% prior to vaccination after introduction of air while stirring at an initial rate of 100 rpm.

Preparation of the feed: 30 g casein hydrolysates were dissolved in 100 mL deionized water to prepare a solution (30%), and 50 g glucose was dissolved in 100 ml deionized water to prepare a glucose solution (50%). The two solutions were sterilized at 121° C. for 20 min.

On the next day, the starter cultures in the ten flasks (for a total of 5 L) were transferred to the fermenter. A temperature of 37° C. and a pH value of 7.0 were set, the dissolved $O_2$ was maintained at >40% by regulating agitation rate and air supply manually.

Flow Feed: 50% glucose and 30% casein hydrolysates were mixed at a solute mass ratio of 2:1.

Flow rates were as followed (25 ml/min was defined as 100%):

$1^{st}$ h: 5%;
$2^{nd}$ h: 10%;
$3^{rd}$ h: 20%;
$4^{th}$ h: 40%;
$5^{th}$ h to the end: 60%.

When the bacterial concentration reached an $OD_{600}$ of about 10.0, the culturing temperature was lowered to 25° C. and 4 g IPTG was added to initiate an induction culture of 12 h. Fermentation was halted when the final concentration reached an $OD_{600}$ of about 40. The bacteria expressing HPV52N40C-L1 protein were obtained, weighted about 2.5 kg.

Example 3

Preparation of HPV52N40C-L1 Protein with a Purity of about 70%

Bacteria were re-suspended at a proportion of 1 g bacteria corresponding to 10 ml lysis buffer (20 mM Tris buffer pH 7.2, 300 mM NaCl). Bacteria were disrupted by an APV homogenizer (Invensys Group) for five times at a pressure of 600 bar. The homogenate was centrifuged at 13,500 rpm (30,000 g) using JA-14 rotor for 15 min, and the supernatant (i.e. the supernatant of disrupted bacteria) was obtained. The supernatant was subjected to 10% SDS-PAGE. At this stage, the HPV52N40C-L1 protein in the supernatant had a purity of about 10% (see FIG. 1, Lane 1).

The supernatant was dialyzed by a CENTRASETTE 5 Tangential Flow Filter (Pall Co.) running at a pressure of 0.5 psi, a flow rate of 500 ml/min, and a tangential flow rate of 200 mL/min, wherein the membrane retention molecular weight was 30 kDa, the dialysis solution was 10 mM phosphate buffer pH 6.0, and the dialysis volume was three times of the volume of the supernatant.

After thorough dialysis, the mixture was centrifuged at 9500 rpm (12,000 g) using JA-10 rotor (Beckman J25 high speed centrifuge) for 20 min, and the precipitate (i.e. the precipitate product free of salts) was collected. The precipitate was re-suspended in 10 mM phosphate buffer (pH 7.0) containing 10 mM DTT and 300 mM NaCl, wherein the volume of the buffer was ⅒ of the volume of the supernatant. The mixture was stirred for 30 min and centrifuged at 13,500 rpm (30,000 g) using JA-14 rotor (Beckman J25 high speed centrifuge) for 20 min. The supernatant and precipitate (i.e. the precipitate obtained after re-dissolution) were collected. The supernatant passed through a filter membrane with an aperture of 0.22 μm. The sample obtained (i.e. re-dissolved supernatant) was used for the purification with cation exchange chromatography (as described in Example 4). 30 μL of 6× loading buffer (12% (w/v) SDS, 0.6% (w/v) bromophenol blue, 0.3M Tris-HCl pH 6.8, 60% (v/v) glycerin, 5% (v/v) β-mercaptoethanol) was added to 150 μL filtered supernatant, and the resultant solution was mixed homogeneously and was placed in a water bath at 80° C. for 10 min. Then, 10 μl sample was subjected to 10% SDS-PAGE at 120V for 120 min. The electrophoretic bands were stained by Coomassie brilliant blue. The electrophoretic result was shown in FIG. 1. The result showed that HPV52N40C-L1 protein was purified and enriched after the steps of precipitation and re-dissolution, with a purity increased from about 10% to about 70% (see FIG. 1, Lane 1 and Lane 3).

Example 4

Chromatographic Purification of HPV52N40C-L1 Protein

1) Purification of HPV52N40C-L1 by Cation Exchange Chromatography

Equipment: AKTA Explorer 100 preparative liquid chromatography system produced by GE Healthcare (i.e. the original Amershan Pharmacia Co.)

Chromatographic media: SP Sepharose 4 Fast Flow (GE Healthcare Co.)

Column Volume: 5.5 cm×20 cm
Buffer: 20 mM phosphate buffer pH 8.0, 10 mM DTT
20 mM phosphate buffer pH 8.0, 10 mM DTT, 2M NaCl
Flow Rate: 25 mL/min
Detector Wavelength: 280 nm
Sample: 3 L of about 70% pure HPV52N40C-L1 protein solution, as filtered through a filter membrane with an aperture of 0.22 μm in Example 3.

Elution protocol: eluting undesired proteins with 500 mM NaCl, eluting the protein of interest with 1000 mM NaCl, collecting eluate eluted with 1000 mM NaCl, and finally getting about 900 mL purified HPV52N40C-L1 sample.

2) Purification of HPV52N40C-L1 by CHT-II Chromatography (Hydroxyapatite Chromatography)

Equipment: AKTA Explorer 100 preparative liquid chromatography system produced by GE Healthcare (i.e. the original Amershan Pharmacia Co.)

Chromatographic media: CHT-II (purchased from Bio-Rad)

Column Volume: 5.5 cm×20 cm
Buffer: 20 mM phosphate buffer pH8.0, 10 mM DTT,
20 mM phosphate buffer pH 8.0, 10 mM DTT, 2M NaCl
Flow Rate: 20 mL/min
Detector Wavelength: 280 nm
Sample: 1000 mM NaCl elution product obtained in the previous step, diluted to a NaCl concentration of 500 mM with 20 mM phosphate buffer pH 8.0, 10 mM DTT.

Elution protocol: eluting undesired proteins with 500 mM NaCl, eluting the protein of interest with 1000 mM NaCl, collecting eluate eluted with 1000 mM NaCl, and finally getting 800 mL purified HPV52N40C-L1 sample.

Figure 2:
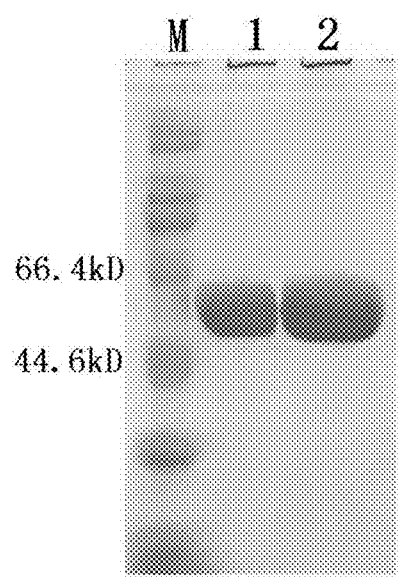
FIG. 2 shows the SDS-PAGE result of HPV52N40C-L1 purified by cation exchange chromatography and CHT-II in Example 4. Lane M: protein molecular weight marker; Lane 1: HPV52N40C-L1 purified by the method of Example 4 (the loading volume was 10 μL); Lane 2: HPV52N40C-L1 purified by the method of Example 4 (the loading volume was 20 μL). The result showed that HPV52N40C-L1 protein purified by the cation exchange chromatography and CHT-II of Example 4 reached a purity of about 98%.

30 μL 6× loading buffer was added to 150 μL HPV52N40C-L1 sample as purified by the method in the present Example, and then the resulted solution was mixed homogeneously. After incubating the solution in a water bath at 80° C. for 10 min, a 10 μL sample was subjected to 10% SDS-PAGE at 120V for 120 min. The electrophoretic bands were stained by Coomassie brilliant blue. The electrophoretic result was shown in FIG. 2. The result showed that after said purification step, the concentration of HPV52N40C-L1 protein was about 0.7 mg/ml, with a purity of greater than 98%.

Example 5

Assembly of HPV52N40C-L1 VLPs

Equipment: CENTRASETTE 5 Tangential Flow Filter (Pall Co.), wherein the membrane retention molecular weight was 30 kDa. Sample: 800 mL HPV52N40C-L1 with a purity of greater than 98% obtained in Example 4.

Sample Concentration: Sample was concentrated to 600 mL by adjusting the tangential flow rate of the tangential flow system to 50 mL/min.

Sample Renaturation: Sample buffer was exchanged with 10 L renaturation buffer (20 mM PB (sodium phosphate buffer) pH 6.0, 2 mM $CaCl_2$, 2 mM $MgCl_2$, 0.5M NaCl, 0.003% Tween-80) thoroughly. The Tangential Flow Filter was run at a pressure of 0.5 psi and a tangential flow rate of 10 mL/min. When the exchange with renaturation buffer was finished, the renaturation buffer was exchanged with storage buffer (20 mM PB (sodium phosphate buffer) pH 6.5, 0.5M NaCl) with an exchange volume of 20 L. The Tangential Flow Filter was run at a pressure of 0.5 psi and a tangential flow rate of 25 mL/min. When the exchange was finished, the sample was aseptically filtrated with a Pall filter (0.22 μm), and thereby obtaining HPV52N40C-L1 VLPs. The HPV52N40C-L1 VLPs were stored at 4° C. for further use.

Example 6

Determination of the Morphology of HPV52N40C-L1 VLPs

1) Transmission Electron Microscopy (TEM) of HPV52N40C-L1 VLPs

Figure 3:
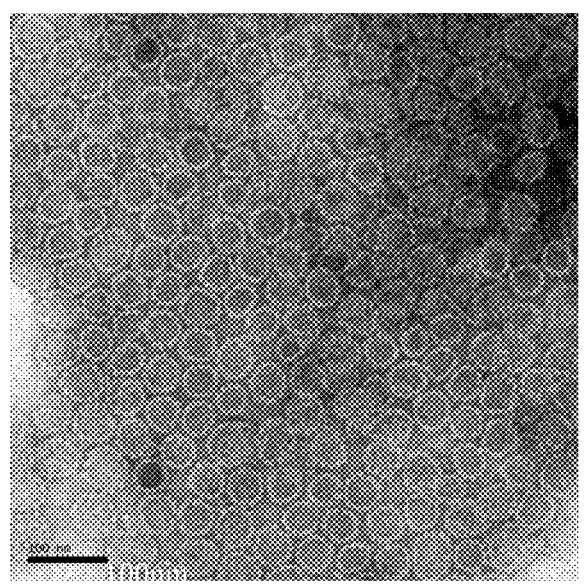
FIG. 3 shows the transmission electron microscopy (TEM) photograph of HPV52N40C-L1 VLPs obtained in Example 5 (taken at 50,000× magnification, Bar=100 nm), as described in Example 6. A large number of VLPs with a radius of about 25 nm were observed in visual field, wherein the particle size was consistent with the theoretic size and the particles were homogenous.

The equipment was a JEOL 100 kV Transmission Electron Microscope (100,000× magnification). HPV52N40C-L1 VLPs obtained in Example 5 were negatively stained with 2% phosphotungstic acid at pH 7.0, and fixed on a copper grid for observation. Results were shown in FIG. 3. A large number of VLPs with a radius of approximately 25 nm, which were homogenous and in a hollow form, were observed.

2) Reconstruction of the Three-Dimensional Structure of HPV52N40C-L1 VLPs

Figure 4A:
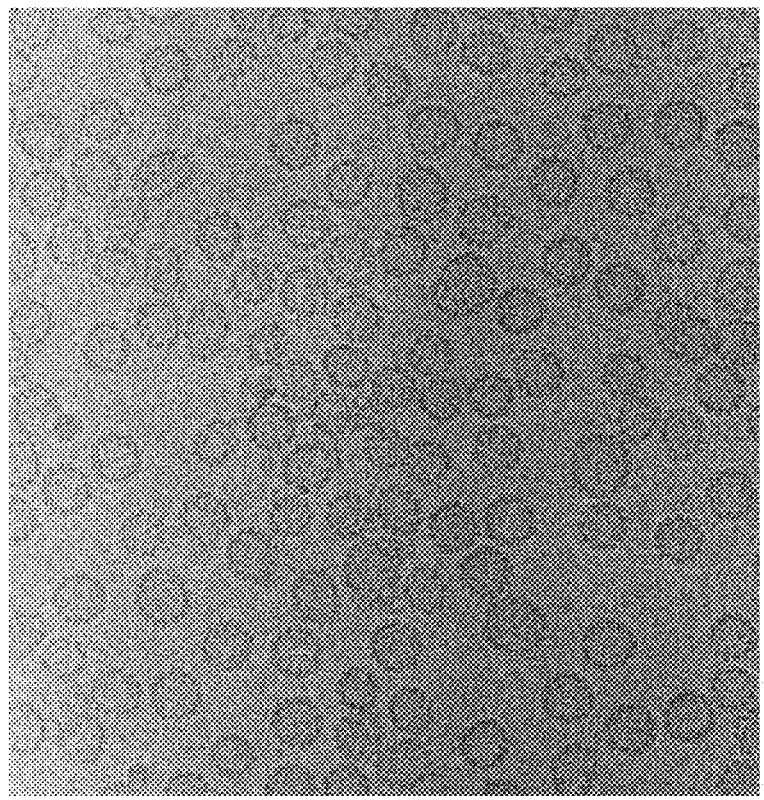
FIG. 4A, HPV52N40C-L1 VLPs.
Figure 4B:
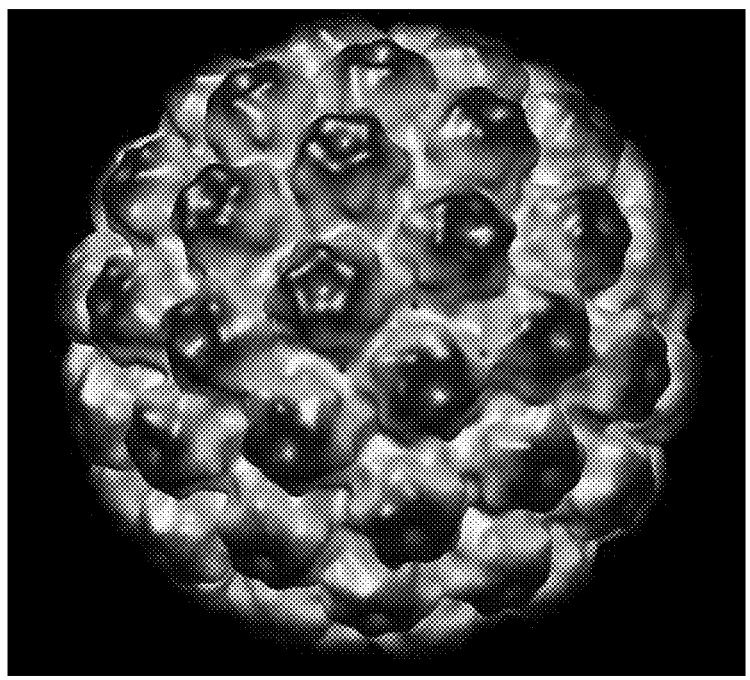
FIG. 4B, the reconstructed three-dimensional structure of HPV52N40C-L1 VLPs. The reconstructed three-dimensional structure showed that HPV52N40C-L1 VLP had an icosahedral structure formed by 72 capsomers (morphologic subunit, pentamer), with T=7 (h=1, k=2). Unlike general icosahedral capsids meeting quasi-equivalent principle, all the subunits in the structure of HPV52N40C-L1 VLP were pentamers, no hexamers were found, and the VLP had a most peripheral diameter of 60 nm. The structure was similar to the three-dimensional structures of the previously reported native HPV viral particles and the HPV VLPs from eukaryotic expression systems (such as, poxvirus expression system) (Baker T S, Newcomb W W, Olson N H. et al. Biophys J. (1991), 60(6): 1445-1456; Hagensee M E, Olson N H, Baker T S, et al. J Virol. (1994), 68(7): 4503-4505; Buck C B, Cheng N, Thompson C D. et al. J Virol. (2008), 82(11): 5190-7).

The three-dimensional structure of HPV52N40C-L1 VLPs was reconstructed by the three-dimensional structure reconstruction experiment using cryo-electron microscopy (Wolf M, Garcea R L, Grigorieff N. et al. Proc Natl Acad Sci USA. (2010), 107(14): 6298-303). In brief, in the cryo-electron microscopy photograph of HPV52N40C-L1 VLPs (FIG. 4A), 400 homogeneous particles with a diameter of above 50 nm were separately selected for computer refolding and structure reconstruction, thereby obtaining the three-dimensional structure of HPV52N40C-L1 VLPs. The three-dimensional structure obtained was shown in FIG. 4B, wherein the resolution of HPV52N40C-L1 VLPs was 22 Å. The result showed that HPV52N40C-L1 VLPs had an icosahedral structure formed by 72 capsomers (morphologic subunit, pentamer), with T=7 (h=1, k=2). Unlike general icosahedral capsids meeting quasi-equivalent principle, all the subunits in the structure of HPV52N40C-L1 VLP were pentamers, no hexamers were found, and the VLPs had a most peripheral diameter of about 60 nm. The structure was similar to the three-dimensional structures of the previously reported native HPV viral particles and the HPV VLPs from eukaryotic expression systems (such as, poxvirus expression system).

3) Dynamic Light-Scattering Measurement of HPV52N40C-L1 VLPs

Figure 5:
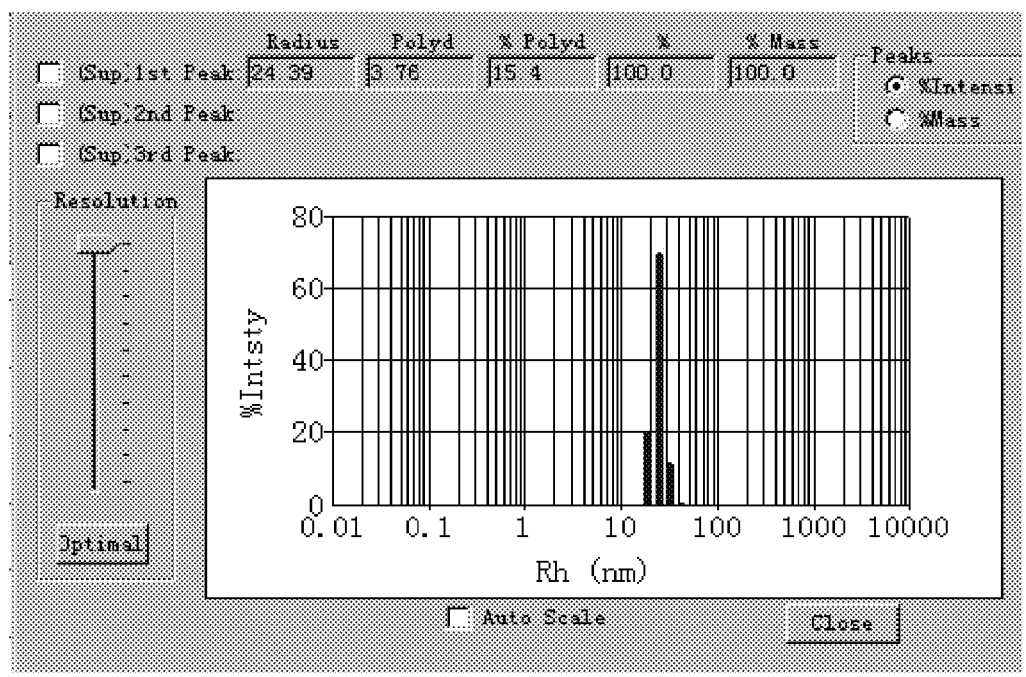
FIG. 5 shows the dynamic light-scattering measurement result of HPV52N40C-L1 VLPs obtained in Example 5, as described in Example 6. The result showed that HPV52N40C-L1 VLPs had a hydrodynamic radius of 24.39 nm and a particle assembly rate of 100%.

DynaPro MS/X dynamic light-scattering instrument (including a temperature controller) (US Protein Solutions Co.) was used for light-scattering measurements. The Regulation algorithm was used in the measurements. The sample was the HPV52N40C-L1 VLPs obtained in Example 5. The sample was passed through a 0.22 μm filter membrane prior to the measurement. The result was shown in FIG. 5. The result showed that HPV52N40C-L1 VLPs had a hydrodynamic radius of 24.39 nm.

Example 7

Determination of Immunogenicity of HPV52N40C-L1 VLP

Establishment of a Cellular Model for HPV52 Pseudovirion Neutralization

HPV can hardly be cultured in vitro, and the HPV host is strongly specific. Thus, HPV can hardly be propagated in hosts other than human. That is, there was not an appropriate animal model for HPV. Therefore, in order to evaluate the immune protection of HPV vaccines quickly, it is urgent to establish an effective model for in vitro neutralization assays.

In Vitro Model of Pseudovirion Infection: by means of the characteristic that HPV VLP can package nucleic acids non-specifically, HPV pseudovirion was formed by expressing HPV L1 and L2 protein in cells, and by packaging episomal viral DNA or reporter plasmids introduced heterologously (Yeager, M. D, Aste-Amezaga, M. et al (2000) Virology (278) 570-7). The concrete methods include methods of recombinant viral expression systems and methods of co-transfection of multi-plasmids. Methods of co-transfection of multi-plasmids were used in the Example exemplarily.

In addition, some improvement directed to HPV systems were made by conventional methods as followed. The calcium phosphate transfection method for 293FT cell line was optimized to obtain a transfection efficiency of up to more than 90%, thereby facilitating large-scale production. The expression plasmid for expressing HPV structural proteins was codon-optimized to express HPV L1 and L2 gene efficiently in mammalian cells, thereby facilitating high efficient assembly of pseudovirion.

Construction of HPV Pseudovirion:

Plasmid p52L1h (the pAAV vector carrying the nucleotide sequence encoding HPV52 L1 protein (NCBI database, Accession Number: Q05138)), plasmid p52L2h (the pAAV vector carrying the nucleotide sequence encoding HPV52 L2 protein (NCBI database, Accession Number: P36763)), and plasmid pN31-EGFP carrying green fluorescent protein gene, were purified by CsCl density gradient centrifugation, wherein said pN31-EGFP and said pAAV vectors were donated by Professor John T. Schiller of NIH. Methods for purifying plasmids using CsCl density gradient centrifugation were well known in the art (see The Molecular Cloning Experiment Guide, 3rd edition).

293FT cells (Invitrogen) cultured on a 10 cm cell culture plate were co-transfected with the purified p52L1h, p52L2h and pN31-EGFP (40 μg for each) by calcium phosphate transfection method. Calcium phosphate transfection method was well known in the art (see The Molecular Cloning Experiment Guide, 3rd edition). In brief, p52L1h, p52L2h and pN31-EGFP (40 μg for each) were added to the mixture of 1 mL HEPES solution (125 μL 1M HEPES pH7.3 per 50 mL deionized water, stored at 4° C.) and 1 mL 0.5M $CaCl_2$ solution. After mixing homogeneously, 2 mL 2× HeBS solution (0.28M NaCl (16.36 g), 0.05M HEPES (11.9 g), and 1.5 mM $Na_2HPO_4$ (0.213 g), dissolved in 1000 mL deionized water, pH 6.96, stored at −70° C.) was added dropwise. After standing at room temperature for 1 min, the mixture was added to the 10 cm cell culture plate where the 293FT cells were cultured. After culturing for 6 hr, the original culture medium was decanted and 10 ml fresh complete medium (Invitrogen Co.) was added. After transfection for 48 hours, the medium was decanted and the cells were washed twice with PBS. Then, the cells were collected and counted. Every $10^8$ cells were re-suspended in 1 mL lysis solution (0.25% Brij58, 9.5 mM $MgCl_2$). After lysing, cell lysate was centrifuged at 5,000 g for 10 min and the supernatant was collected. The Pseudovirion solution was obtained after adding 5M NaCl to a final concentration of 850 mM, and then was stored in small packages at −20° C.

Determination of the Neutralization Titers of Antibodies

293FT cells (Invitrogen) were plated on a 96-well cell culture plate (1.5×$10^4$ cells/well). Neutralization assay was performed five hours later. Serum samples comprising antibodies to be tested were serially diluted with 10% DMEM half-by-half. The diluted samples (50 μL for each) were respectively mixed with 50 μL Pseudovirion solution diluted in 10% DMEM as prepared above (moi=0.1). After incubating at 4° C. for 1 h, the mixture was added to the 96-well cell culture plate with 293FT cells. The mixture was then incubated for 72 h at 37° C. Antibody titers of samples were estimated by observing fluorescence. Infection percentage of cells in each well was then checked by flow cytometry (EPICS XL, American Beckman Coulter Co.). The exact antibody titers of serums were calculated. Infection percentage was the percentage of cells in the positive region of the cell sample to be tested minus that in the positive region of the uninfected control cell sample.

Infection-inhibition percentage=(1−infection percentage of wells with serum/infection percentage of wells without serum)×100%

The positive region was defined as the cell region having a GFP signal determined by flow cytometry at least 10 times higher than the signal of the control cells.

Neutralization titer of antibodies was defined as the highest dilution fold under which the infection-inhibition percentage reached above 50%. Antibodies were considered as having neutralizing capacity if their infection-inhibition percentage was above 50% after 50 times dilutions.

Evaluation of Immune Protection of Vaccination of Animals with HPV52 VLPs

Rabbits were used to evaluate the immune protection of the HPV52 VLPs according to the invention. Animals for vaccination were female rabbits (general grade), 6-8 weeks old, purchased from the Disease Prevention and Control Center of Guangxi province. HPV52N40C-L1 VLPs (at a concentration of 0.1 mg/ml) prepared in Example 5, were mixed with equal volume of complete Freund's Adjuvant for the first vaccination, or with equal volume of incomplete Freund's Adjuvant for the booster. The vaccination procedure was as followed: the first vaccination at Week 0, and the booster at Weeks 4 and 10, respectively. Rabbits were vaccinated via muscle injection, with 100 μg per rabbit for the first vaccination, and with 50 μg per rabbit for the booster.

After the first vaccination, peripheral venous blood was collected every week, and serum was separated and stored for test. The neutralization titers of antibodies against HPV52 pseudovirion in the rabbit serum were determined by the method above.

Figure 6:
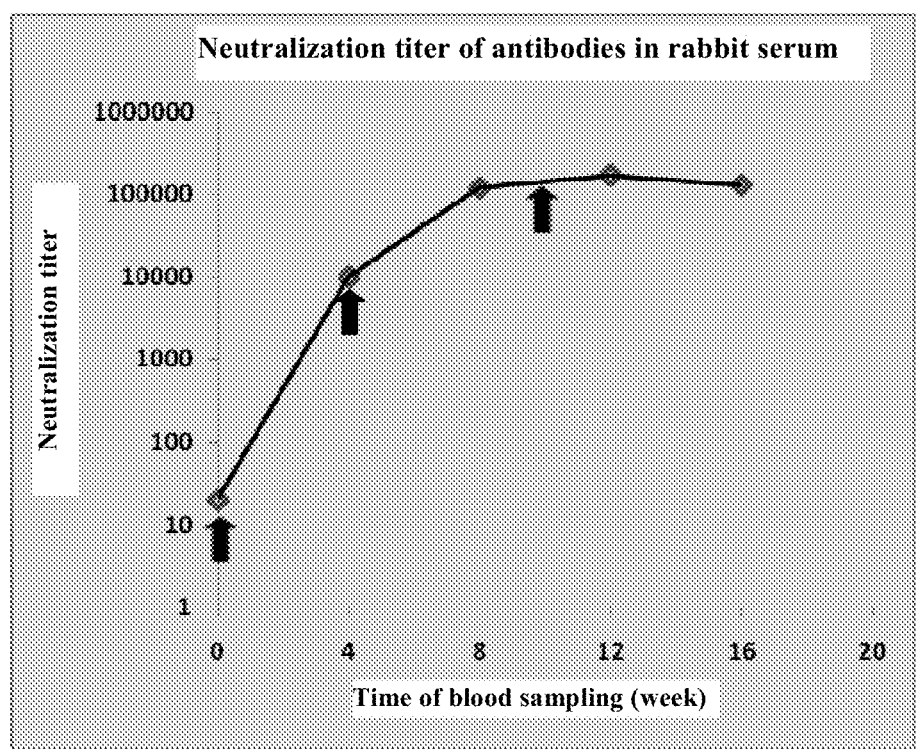
FIG. 6 shows neutralization titers of antibodies in serum at different stages after vaccination of rabbits with HPV52N40C-L1 VLPs as determined in Example 7. Vaccination times are indicated with arrows. The neutralization titers of antibodies increased significantly one month after the first vaccination, and reached a peak level of $10^5$ after a booster.

The result was shown in FIG. 6. FIG. 6 showed that neutralization titers of antibodies in serum at different stages after vaccination of rabbits with HPV52N40C-L1 VLPs. Vaccination times were indicated by arrows. It could be seen that the neutralization titers of antibodies increased significantly one month after the first vaccination, and reached a peak level of $10^5$ after one booster. It showed that HPV52N40C-L1 VLPs obtained by the methods as described in Examples 1-5 had good immunogenicity, could induce the generalization of neutralization antibodies against HPV52 with a high titer in animals, and could be used as an effective vaccine for the prevention of HPV52 infection. In addition to Freund's Adjuvant, other adjuvants well known in the art might also be used in the vaccines, for example, aluminum hydroxide or aluminum phosphate adjuvants.

Example 8

Figure 7:
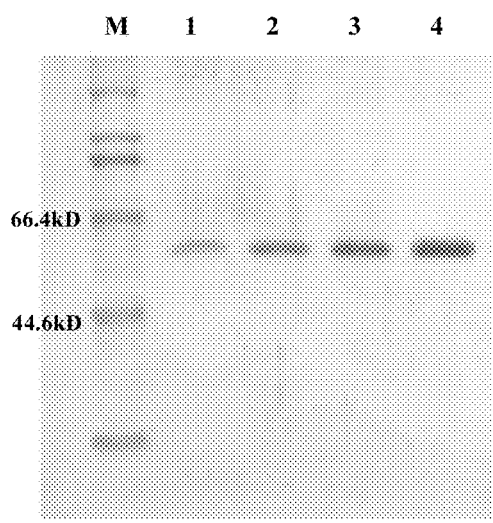
FIG. 7 shows the SDS-PAGE results of the HPV52 L1 proteins having 27, 35, 38 or 42 amino acids truncated at the N-terminal, respectively, i.e. HPV52N27C-L1, HPV52N35C-L1, HPV52N38C-L1, HPV52N42C-L1 (their amino acid sequences were set forth in SEQ ID NOs: 1, 7, 10 and 13, respectively), as obtained in Example 8. Lane M: protein molecular weight marker; Lane 1: HPV52N27C-L1 protein (the loading volume was 10 µL); Lane 2: HPV52N35C-L1 protein (the loading volume was 10 µL); Lane 3: HPV52N38C-L1 protein (the loading volume was 10 µL); Lane 4: HPV52N42C-L1 protein (the loading volume was 10 µL). The results showed that the truncated proteins, i.e. HPV52N27C-L1, HPV52N35C-L1, HPV52N38C-L1, HPV52N42C-L1, as obtained in Example 8, reached a purity of about 98%.
Figure 8A:
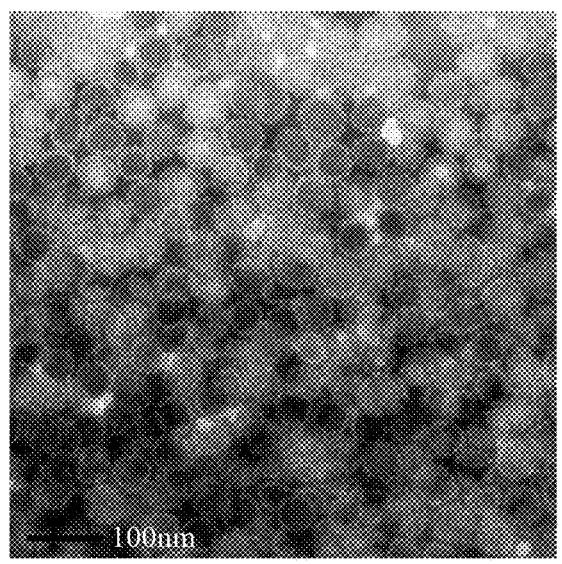
FIG. 8A, HPV52N27C-L1 VLPs.
Figure 8B:
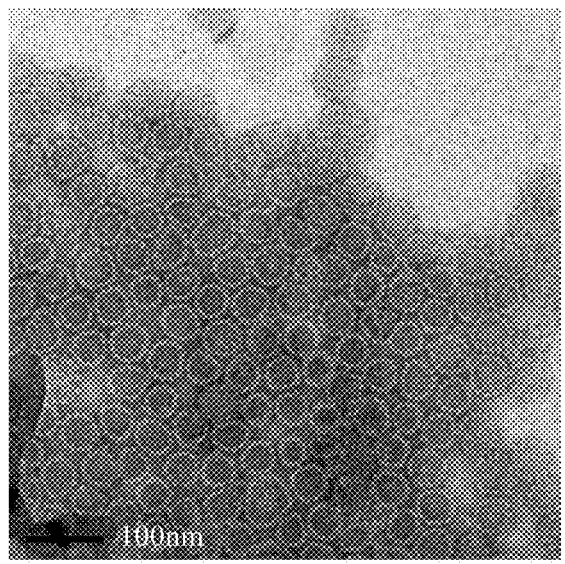
FIG. 8B, HPV52N35C-L1 VLPs.
Figure 8C:
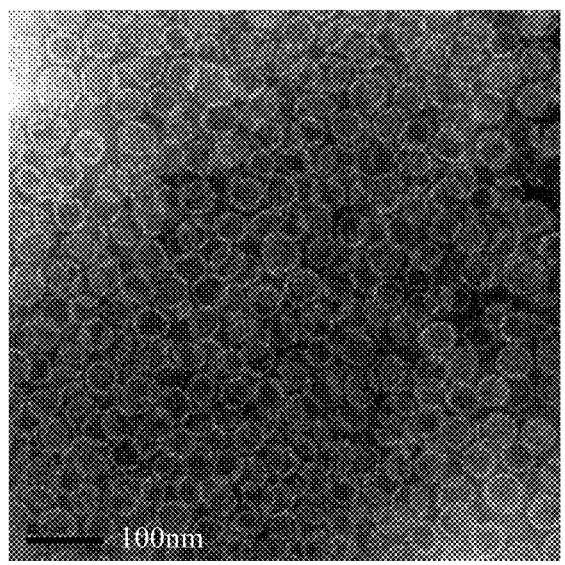
FIG. 8C, HPV52N38C-L1 VLPs.
Figure 8D:
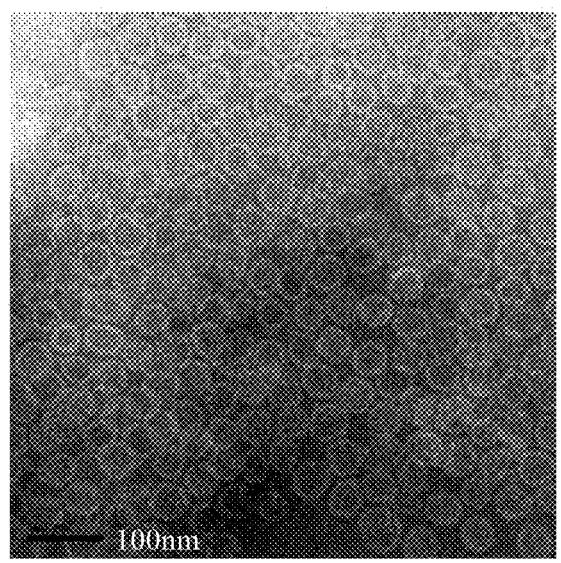
FIG. 8D, HPV52N42C-L1 VLPs. The results showed that a large number of VLPs with a radius of about 25 nm were observed in visual field in the four figures, wherein the particle size was consistent with the theoretic size and the particles were homogenous.
Figure 9A:
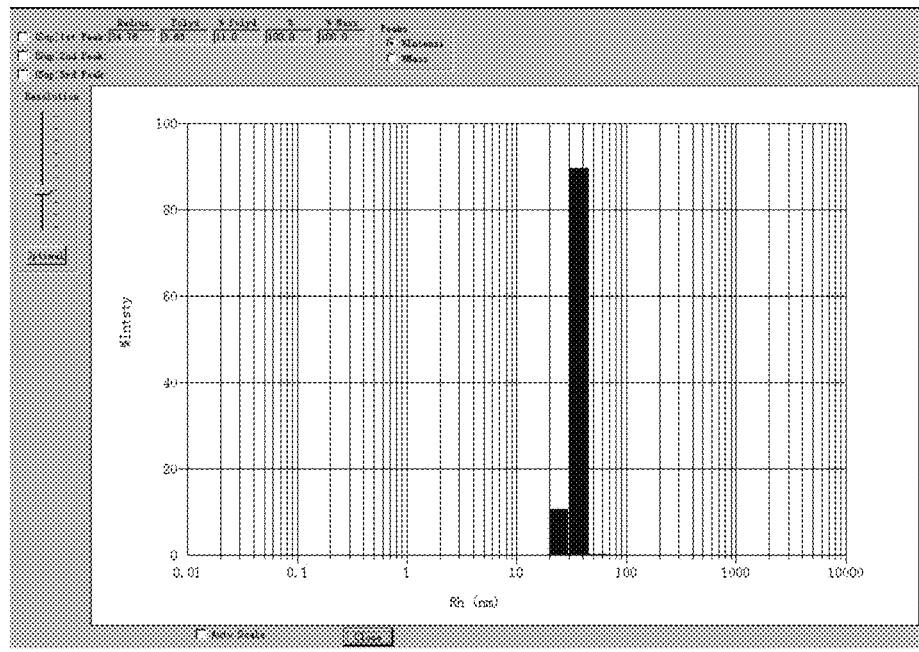
FIG. 9A, HPV52N27C-L1 VLPs.
Figure 9B:
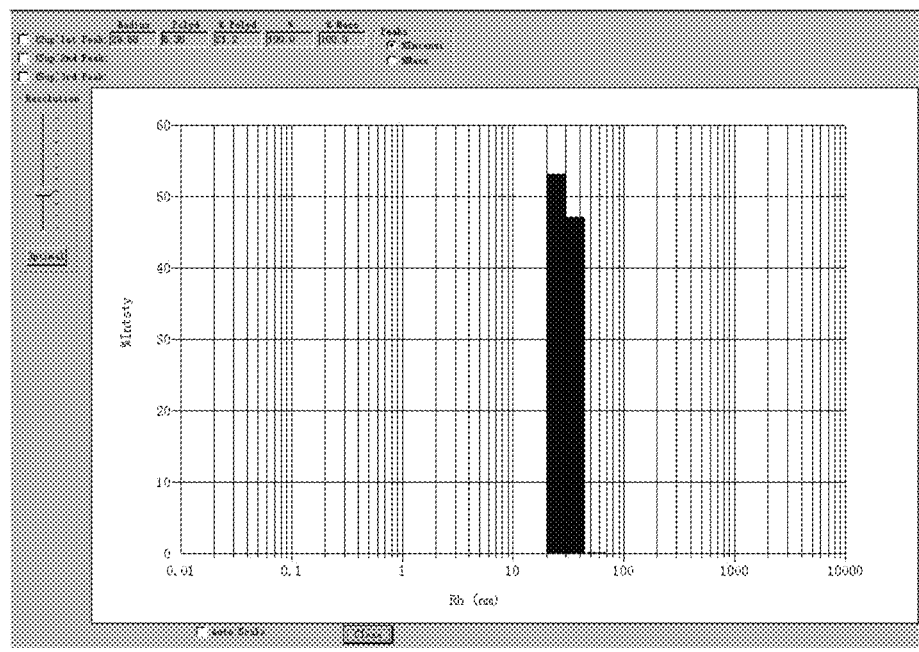
FIG. 9B, HPV52N35C-L1 VLPs.
Figure 9C:
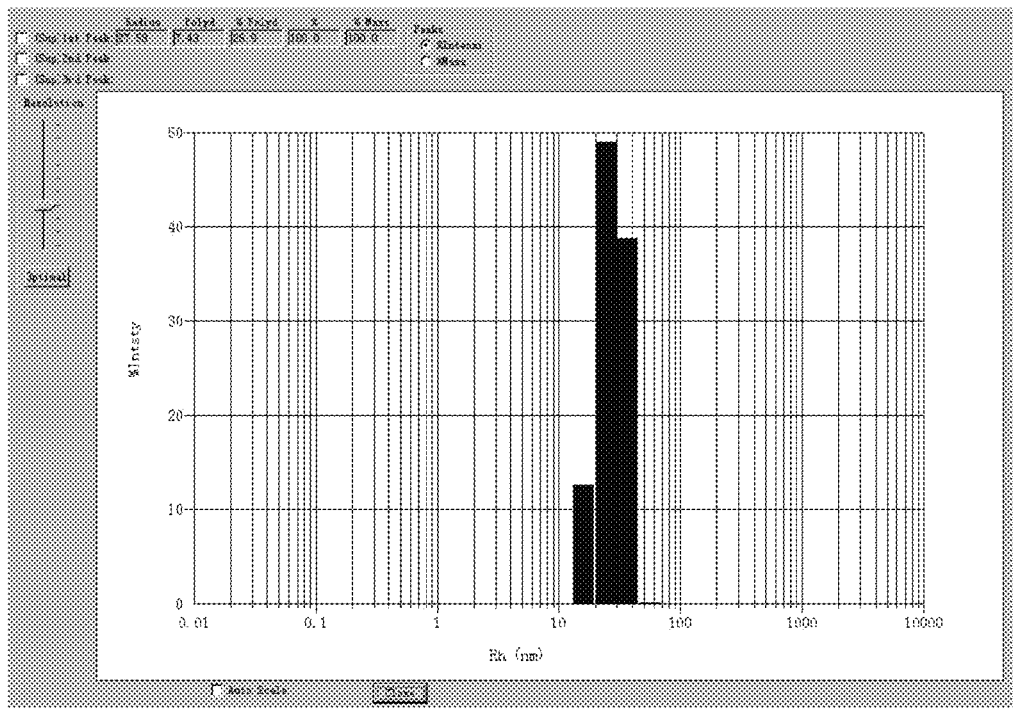
FIG. 9C, HPV52N38C-L1 VLPs.
Figure 9D:
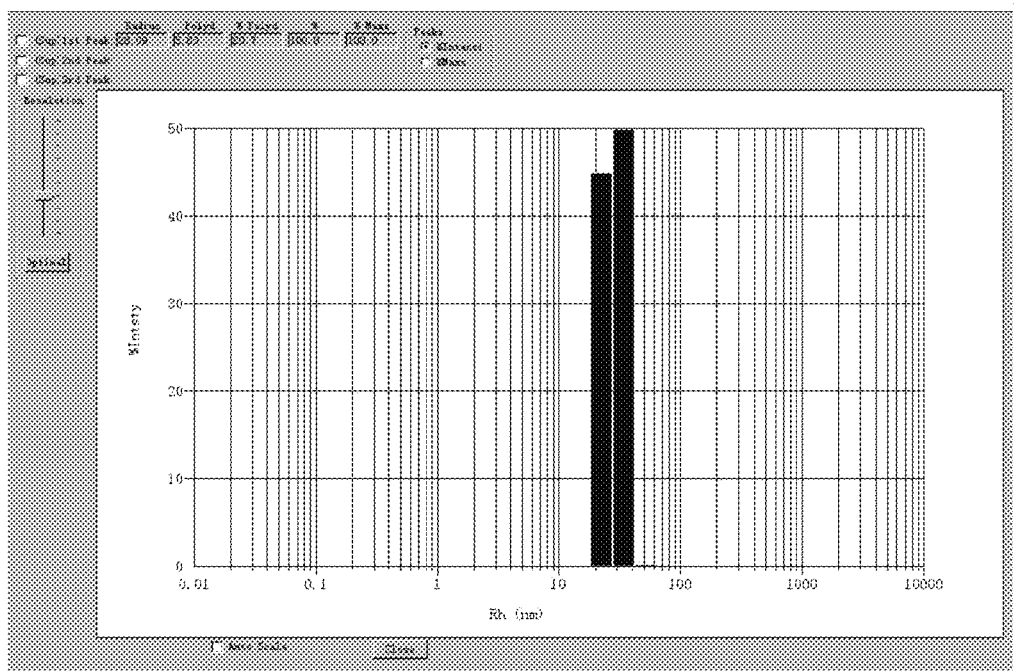
FIG. 9D, HPV52N42C-L1 VLPs. The results showed that HPV52N27C-L1, HPV52N35C-L1, HPV52N38C-L1, and HPV52N42C-L1 VLPs had a hydrodynamic radius of about 25 nm and a particle assembly rate of 100%.

Preparation and Morphologic Observation of HPV52N27C-L1, HPV52N35C-L1, HPV52N38C-L1, HPV52N42C-L1 Proteins and VPLs HPV52N27C-L1, HPV52N35C-L1, HPV52N38C-L1, and HPV52N42C-L1 having 27, 35, 38 or 42 amino acids truncated at the N-terminal (their amino acid sequences were set forth in SEQ ID NOs: 1, 7, 10 and 13, respectively), were prepared and purified basically by the methods as described in Examples 1-4. The four proteins thus obtained had a purity of above 98% (see FIG. 7).

The purified HPV52N27C-L1, HPV52N35C-L1, HPV52N38C-L1 and HPV52N42C-L1 proteins were assembled into VLPs basically by the method as described in Example 5, respectively, designated as HPV52N27C-L1 VLPs, HPV52N35C-L1 VLPs, HPV52N38C-L1 VLPs, and HPV52N42C-L1 VLPs, respectively.

HPV52N27C-L1 VLPs, HPV52N35C-L1 VLPs, HPV52N38C-L1 VLPs, and HPV52N42C-L1 VLPs were subjected to transmission electron microscopy and dynamic light scattering observation basically by the method as described in Example 6, respectively. The results were shown in FIG. 8 and FIG. 9. FIG. 8 showed that the truncated proteins could form a large number of VLPs with a radius of about 25 nm, wherein the particle size was consistent with the theoretic size and the particles were homogenous. FIG. 9 showed that HPV52N27C-L1, HPV52N35C-L1, HPV52N38C-L1, HPV52N42C-L1 VLPs had a hydrodynamic radius of about 25 nm and a particle assembly rate of 100%.

In addition, it was demonstrated by the method as described in Example 7 that the HPV52N27C-L1, HPV52N35C-L1, HPV52N38C-L1, HPV52N42C-L1 VLPs obtained in the invention also had good immunogenicity, could induce the generalization of neutralization antibodies with a high titer in animals, and therefore could be used as an effective vaccine for the prevention of HPV infection.

Although the specific embodiments of the present invention have been described in details, those skilled in the art would understand that, according to the teachings disclosed in the specification, various modifications and changes can be made without departing from the sprit or scope of the present invention as generally described, and that such modifications and changes are within the scope of the present invention. The scope of the present invention is given by the appended claims and any equivalents thereof.

The invention claimed is:

1. A truncated HPV52 L1 protein, wherein the truncated HPV52 L1 protein is different from wild type HPV52 L1 protein by a deletion of amino acid positions 2-35, 2-40, or 2-42 at an N-terminal of the wild type HPV52 L1 protein, wherein said truncated HPV52 L1 protein is expressed by *E. coli*.

2. The truncated HPV52 L1 protein as claimed in claim 1, wherein the protein consists of an amino acid sequence selected from the group consisting of SEQ ID NO: 7, SEQ ID NO: 12, and SEQ ID NO: 13.

3. The HPV52 L1 protein as claimed in claim 2, wherein the protein consists of the amino acid sequence as set forth in SEQ ID NO 12.

4. An isolated nucleic acid, encoding the truncated HPV52 L1 protein according to claim 1.

5. A vector comprising the isolated nucleic acid according to claim 4.

6. An *E. coli* host cell, comprising (1) the isolated nucleic acid according to claim 4 or (2) a vector comprising the isolated nucleic acid.

7. A HPV52 virus-like particle, comprising the truncated protein according to claim 1.

8. A composition comprising the truncated HPV52 L1 protein according to claim 1.

9. A composition comprising (1) the isolated nucleic acid according to claim 4 or (2) a vector comprising the isolated nucleic acid.

10. A composition comprising the host cell according to claim 6.

11. A composition comprising, HPV52 virus-like particle according to claim 7.

12. A pharmaceutical composition or vaccine comprising the HPV52 virus-like particle according to claim 7, and optionally comprising pharmaceutically acceptable carriers and/or excipients, wherein the HPV52 virus-like particle is present in an amount effective for preventing HPV infection or cervical cancer.

13. A method for obtaining a truncated HPV52 L1 protein comprising:
   expressing the truncated HPV52 L1 protein of claim 1 in an *E. coli* expression system, and carrying out a purification process on the lysis supernatant containing said protein.

14. A method for preparing the HPV52 virus-like particle according to claim 7, comprising:
   a) purifying a truncated HPV52 L1 protein which is different from wild type HPV52 L1 protein by a deletion of amino acid positions 2-35, 2-40, or 2-42 at the N-terminal of the wild type HPV52 L1 protein, to have a purity of at least 50% by a chromatography; and
   b) removing the reductant from the truncated protein obtained in a).

15. The method according to claim 13, wherein the method comprises the steps of:
   a) expressing said truncated HPV52 L1 protein in *E. coli*;
   b) disrupting the *E. coli* which has expressed the truncated protein, in a solution at a salt concentration of 100 mM to 600 mM, and isolating the supernatant;
   c) decreasing the salt concentration of the supernatant of b) to 100 mM or less, by using water or a solution at a low salt concentration, and collecting a precipitate;
   d) re-dissolving the precipitate of c) in a solution at a salt concentration of 150 mM to 250 mM and adding a reductant to the solution, and isolating the resultant solution,
   wherein the resultant solution contains the truncated HPV52 L1 protein with a purity of at least 50%.

16. A method for preparing an HPV52 virus-like particle, comprising:
   a) expressing the truncated HPV52 L1 protein of claim 1 in an *E. coli* expression system;
   b) disrupting the *E. coli* which has expressed the truncated HPV52 L1 protein in a solution at a salt concentration of 100 mM to 600 mM, and isolating a supernatant;
   c) decreasing the salt concentration of the supernatant of b) to 100 mM or less by using water or a solution at a low salt concentration, and collecting a precipitate;
   d) re-dissolving the precipitate of c) in a solution at a salt concentration of 150 mM to 250 mM and adding a reductant to the solution, and then isolating the resultant solution, wherein the solution contains the truncated HPV52 L1 protein with a purity of at least 50%; and
   e) removing the reductant from the truncated HPV52 L1 protein obtained in d).

* * * * *